(12) United States Patent
Prassler et al.

(10) Patent No.: US 9,650,432 B2
(45) Date of Patent: May 16, 2017

(54) RODENT COMBINATORIAL ANTIBODY LIBRARIES

(75) Inventors: Josef Prassler, Germering (DE); David Ott, München (DE); Stefanie Thiel, München (DE); Yvonne Stark, München (DE); Ute Keck, Basel (CH); Thomas Pietzonka, Basel (CH); Hilmar Ebersbach, Basel (CH)

(73) Assignee: MORPHOSYS AG, Martinsried/Planegg (DE)

( * ) Notice: Subject to any disclaimer, the term of this patent is extended or adjusted under 35 U.S.C. 154(b) by 0 days.

(21) Appl. No.: 13/574,782

(22) PCT Filed: Jan. 28, 2011

(86) PCT No.: PCT/EP2011/051266
§ 371 (c)(1),
(2), (4) Date: Oct. 10, 2012

(87) PCT Pub. No.: WO2011/092313
PCT Pub. Date: Aug. 4, 2011

(65) Prior Publication Data
US 2013/0030157 A1    Jan. 31, 2013

Related U.S. Application Data

(60) Provisional application No. 61/299,380, filed on Jan. 29, 2010.

(30) Foreign Application Priority Data

Jan. 29, 2010 (EP) .................................. 10152164

(51) Int. Cl.
*C07K 16/00* (2006.01)
*C07K 16/22* (2006.01)

(52) U.S. Cl.
CPC ............ *C07K 16/00* (2013.01); *C07K 16/005* (2013.01); *C07K 16/22* (2013.01); *C07K 2317/20* (2013.01); *C07K 2317/55* (2013.01); *C07K 2317/56* (2013.01); *C07K 2317/565* (2013.01); *C07K 2317/73* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| WO | 0192291 | 12/2001 | |
|----|---------|---------|---|
| WO | 2006030238 | 3/2006 | |
| WO | WO 2006030238 A1 * | 3/2006 | ............ C12N 15/10 |
| WO | 2011000543 | 1/2011 | |

OTHER PUBLICATIONS

O'Brien et al. "Development of a novel monoclonal antibody with reactivity to a wide range of Venezuelan equine encephalitis virus strains" Virol J. 6:206-14; published Nov. 19, 2009.*
Rothe et al. (2007) "The Human Combinatorial Antibody Library HuCAL GOLD Combines Diversification of All Six CDRs According to the Natural Immune System with a Novel Display Method for Efficient Selection of High-Affinity Antibodies" J. Mol. Biol. 376(4):1182-1200.*
Sepulveda et al. (2008) "Design and testing of PCR primers for the construction of scFv libraries representing the immunoglobulin repertoire of rats" Journal of Immunological Methods 332(1-2):92-102.*
TiterMax (www.titermax.com) technical information web page "Can TiterMax(R) be used to make hybridomas?", captured Mar. 28, 1997.*
Gojobori et al. (1986) "Relative Contributions of Germline Gene Variation and Somatic Mutation to Immunoglobulin Diversity in the Mouse" Mol. Biol. Evol. 3(2):156-167.*
De Jaeger Gerrt et al: "Use of phage display for isolation and characterization of single-chain variable fragments against dihydroflavonol 4-reductase from Petunaia hybrida", FEBS Letters, vol. 403, No. 2, 1997, p. 116-122.
Sidhu Sachdev S. et al: "Synthetic Therapeutic anitbodies", Nature Chemical Biology, vol. 2, No. 2, Jan. 12, 2006.
PCT/EP2011/051266 ISR and Written Opinion.
Hoogenboom "Selecting and screening recombinant antibody libraries" Nature Biotechnology, vol. 23, No. 9, Sep. 1, 2005 pp. 1105-1116.
Carter, P. J. (2006) Nat. Rev. Immunol 6, 343-357.
Rothe et al., 2008, J. Mol. Biol. 379, 1182-1200.
Steidl, et al. "In Vitro affinity maturation of human GM-CSF antibodies by targeted CDR-diversification" 2008. Mol. Immunol. 46(1):135-44.
Ward et al., 'Binding activities of a repertoire of single immunoglobulin variable domains secreted from *Escherichia coli*,' Nature, 1989, 341:544-546.
Cobaugh et al, 2008, Journal of Molecular Biology 378, 622-633.
Sommavilla et al., "Design and construction of a naïve mouse antibody phage display library", J. Immunol. Methods (2010) 353, 31-43.
Kaushik, et al. "The primary antibody repertoire of normal, immunodeficient and autoimmune mice is characterized by differences in V gene expression", Res. Immunol. 1996, 147, 9-26.
Okamato et al.: "optimal construction of non-immune scFv phase display libraries form mouse bone marrow and spleen established to selected specific scFvs efficiently binding to antigen", Biochemical and Biophysical Research Communications, Academic Press Inc. Orlando, FL. US. vol. 323, No. 2, Oct. 2004.
Knappik A, Gel L, Honegger A, Pack P, Fischer M, Wellnhofer G, Hoess A, Mlle J, Plueckthun A, VirnekAs B, 'Fully synthetic human combinatorial antibody libraries (HuCAL) based on modular consensus frameworks and CDRs randomized with trinucleotides', J Mol Biol. Feb. 11, 2000; 296(1):57-86.

* cited by examiner

Primary Examiner — Karen S Weiler
(74) Attorney, Agent, or Firm — Licata & Tyrrell P.C.

(57) ABSTRACT

The present invention provides synthetic rodent antibody libraries, such as mouse or rat antibody libraries, as well as polypeptides, nucleic acids, vectors, host cells and methods used in conjunction with these libraries. The present invention also provides antibodies isolated from such libraries and variants of such antibodies.

24 Claims, 63 Drawing Sheets

Figure 1

|    | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 |
|----|----|----|----|----|----|----|----|----|----|----|----|----|----|----|----|----|----|----|----|----|----|----|----|-----|-----|
| mVH1 | | K | T | L | T | V | D | K | P | S | S | T | A | Y | M | Q | L | S | S | L | T | S | E | D | S |
| mVH1_RV | | R | V | T | L | T | V | D | K | P | S | S | T | A | Y | M | Q | L | S | S | L | T | S | E | D | S |

FW3 stabilizing salt-bridge

Figure 2

Mouse JH

| | | | | | | FW4 | | | | | | |
|---|---|---|---|---|---|---|---|---|---|---|---|---|
| JH1 | Y | W | Y | F | D | V | W | G | A | G | T | T | V | T | V | S | S |
| JH2 | Y | F | D | Y | W | G | Q | G | T | T | L | T | V | S | S |
| JH3 | | A | W | F | A | Y | W | G | Q | G | T | L | V | T | V | S | A |
| JH4 | Y | Y | A | M | D | Y | W | G | Q | G | T | S | V | T | V | S | S |

StyI-site ............................. BlpI-site

Figure 4a

| | FWR3 | 95 | 96 | 97 | 98 | 99 | 100 | a | b | m | n | 101 | 102 | FR4 |
|---|---|---|---|---|---|---|---|---|---|---|---|---|---|---|
| 7_aa 446 seq. | | 27%G 11%D 11%S 10%Y 7%E 6%L 5%R | 25%G 15%Y 12%D 7%T 7%S 7%N 6%R | 33%Y 12%G 9%D 9%T 6%S 5%W | 22%G 21%Y 14%A 8%W 6%D 5%R | | | | | | 54%F 17%M | 62%D 26%A | 90%Y | |
| 8_aa 645 seq. | | 18%G 16%Y 10%S 9%D 9%R 6%E 5%H 5%W | 26%G 17%Y 11%D 7%R 7%L 5%T 4%S 4%N | 23%Y 16%G 11%N 9%D 6%R 6%T 6%S 5%L | 25%Y 16%G 10%D 9%W 8%S 5%T | 32%Y 19%A 8%G 6%W 5%S | | | | | 64%F 19%M | 76%D 18%A | 86%Y 9%V | |
| 9_aa 1705 seq. | | 44%Y 22%G 6%S | 42%Y 17%G 6%D 5%R | 56%Y 7%N 7%G 7%L | 52%G 16%Y 6%S | 20%S 19%Y 13%R 11%G | 39%Y 13%H 12%A 10%S | | | | 75%F 13%M 6%L | 87%D 8%A 1%G | 75%Y 16%V 5%F | |

Figure 4b

| 10 aa | | | | | | | | | | | |
|---|---|---|---|---|---|---|---|---|---|---|---|
| 1311 seq. | 36% Y<br>12% G<br>10% R<br>7% D<br>5% N | 34% Y<br>19% G<br>11% D<br>5% N | 46% Y<br>14% G<br>9% L<br>6% S | 40% G<br>16% Y<br>7% D<br>7% S | 30% S<br>18% Y<br>13% G<br>9% R | 30% S<br>23% Y<br>10% G<br>7% W | 38% Y<br>19% A<br>8% W<br>7% H | | 71% F<br>20% M | 82% D<br>14% A | 86% Y<br>10% V |

| 11 aa | | | | | | | | | | | |
|---|---|---|---|---|---|---|---|---|---|---|---|
| 1054 seq. | 33% Y<br>13% G<br>8% S<br>7% D<br>7% R<br>5% N | 31% Y<br>15% D<br>15% G<br>5% E<br>5% R | 46% Y<br>11% G<br>8% S<br>6% L | 32% Y<br>28% G<br>8% S<br>5% D<br>5% R | 21% G<br>20% Y<br>14% S<br>8% R<br>7% P<br>6% N<br>5% T | 30% Y<br>21% S<br>15% G<br>5% D | 34% Y<br>16% S<br>10% W<br>9% F<br>6% G | 38% Y<br>30% A<br>7% G<br>7% W<br>5% S | 61% F<br>31% M | 85% D<br>13% A | 86% Y<br>11% V |

| 12 aa | | | | | | | | | | | |
|---|---|---|---|---|---|---|---|---|---|---|---|
| 1189 seq. | 47% Y<br>8% G<br>7% D<br>7% R<br>7% S | 38% N<br>15% Y<br>14% G<br>5% D | 68% Y<br>6% G | 48% G<br>22% Y<br>5% D<br>5% L | 52% S<br>14% Y<br>11% S<br>7% R | 51% S<br>15% G<br>8% Y<br>5% D<br>5% L | 37% T<br>18% Y<br>16% S<br>6% R<br>6% G | 59% Y<br>10% W<br>6% S<br>5% R | 67% Y<br>16% A | 77% F<br>16% M | 92% D<br>5% A | 85% Y<br>12% V |

(numbering according to Kabat)
Illustration reduced to amino acids with an appearance of >=5%.

Figure 5

| FW3 | | | | | | | | | | | FW4 |
|---|---|---|---|---|---|---|---|---|---|---|---|
| 95 | 96 | 97 | 98 | 99 | 100 | a | b | m | n | 101 | 102 |
| 32% Y | 31% Y | 47% Y | 39% G | 21% S | 24% S | 27% Y | 27% Y | 38% Y | 68% F | 83% D | 82% Y |
| 17% G | 19% G | 11% G | 22% Y | 20% G | 22% Y | 23% S | 18% S | 19% A | 20% M | 13% A | 12% V |
| 8% S | 10% D | 6% L | 6% D | 19% Y | 18% G | 10% G | 10% G | 6% G | 4% L | 1% G | 2% F |
| 7% D | 5% N | 5% D | 6% S | 9% R | 6% D | 8% R | 8% W | 6% H | 1% E | 1% P | 1% H |
| 7% R | 5% R | 5% N | 4% L | 5% D | 5% R | 6% D | 7% R | 6% S | 1% G | | 1% S |
| 4% E | 4% L | 4% R | 4% N | 5% N | 4% L | 6% T | 5% D | 6% W | 1% S | | |
| 4% H | 4% S | 4% S | 4% R | 4% T | 3% N | 4% L | 4% A | 3% L | 1% V | | |
| 3% N | 3% A | 3% T | 4% T | 3% L | 3% P | 3% H | 4% F | 2% D | 1% Y | | |
| 3% W | 3% E | 3% A | 2% A | 3% P | 3% T | 3% P | 4% T | 2% F | | | |
| 2% A | 3% T | 2% F | 2% F | 2% A | 3% V | 2% A | 3% N | 2% P | | | |
| 2% K | 2% F | 2% I | 2% P | 2% F | 2% A | 2% N | 2% L | 2% R | | | |
| 2% L | 2% P | 2% P | 1% E | 2% V | 2% H | 2% V | 2% P | 2% T | | | |
| 2% P | 2% V | 2% V | 1% I | 1% E | 1% C | 1% E | 2% V | 2% V | | | |
| 1% F | 2% W | 2% W | 1% K | 1% H | 1% E | 1% F | 1% E | 1% C | | | |
| 1% I | 1% H | 1% E | 1% V | 1% I | 1% F | 1% I | 1% H | 1% I | | | |
| 1% Q | 1% I | 1% H | 1% W | 1% K | 1% I | 1% K | 1% I | 1% N | | | |
| 1% T | 1% K | 1% Q | | 1% Q | 1% K | 1% W | | | | | |
| 1% V | 1% Q | | | 1% W | 1% W | | | | | | |

(numbering according to Kabat)

Figure 6

| FW3 | | | | | | | | | | FW4 | |
|---|---|---|---|---|---|---|---|---|---|---|---|
| 95 | 96 | 97 | 98 | 99 | 100 | a | b | m | n | 101 | 102 |
| 20%Y<br>20%G<br>10%D<br>10%S<br>10%R<br>1.59%all | 20%Y<br>20%G<br>10%D<br>10%S<br>10%R<br>1.59%all | 40%Y<br>10%G<br>5%D<br>5%L<br>5%R<br>5%S<br>1.58%all | 15%Y<br>15%G<br>15%S<br>5%R<br>5%D<br>5%N<br>2.10%all | 15%Y<br>15%G<br>15%S<br>5%R<br>5%D<br>5%N<br>2.10%all | 15%Y<br>15%G<br>15%S<br>5%R<br>5%D<br>5%N<br>2.10%all | 15%Y<br>15%G<br>15%S<br>5%R<br>5%D<br>5%N<br>2.10%all | 30%Y<br>10%S<br>10%G<br>2.63%all | 30%Y<br>20%A<br>2.63%all | 60%F<br>20%M<br>1.05%all | 80%D<br>20%A | 80%Y<br>20%V |
| T1 | | T2 | T3 | | | | T4 | T5 | T6 | wobble | T7 |
| 19 | 19 | 19 | 19 | 19 | 19 | 19 | 19 | 19 | 19 | 2 | 2 |

Trim-lib Diversity

Figure 8

| FW3 | | | | | | | | | FW4 | | | |
|---|---|---|---|---|---|---|---|---|---|---|---|---|
| Y | C | 89 | 90 | 91 | 92 | 93 | 94 | 95 | 96 | T | F | G | G |
| | | 50%Q<br>10%F<br>10%S<br>1.57%all | 100%Q | 20%G<br>20%S<br>10%Y<br>2.63%all | 30%S<br>15%T<br>15%N<br>10%Y<br>1.57%all | 30%S<br>25%H<br>15%E<br>1.57%all | 25%Y<br>20%V<br>10%L<br>10%F<br>1.84%all | 100%P | 30%Y<br>20%L<br>10%P<br>10%F<br>1.57%all | | | |
| Trimix | | T8 | - | T9 | T10 | T11 | T12 | - | T13 | | | |
| Diversity | | 19 | 1 | 19 | 19 | 19 | 19 | 1 | 19 | | | |

Figure 11

Figure 17a
Data for purification with Isopropanol

| Construct | conc [mg/ml] | yield [mg] | yield [mg/L] | Tm [°C] |
|---|---|---|---|---|
| VkB1_VH3 | 0.14 | 0.9 | 3.70 | 71.1 |
| VkB3_VH3 | 1.00 | 5.4 | 21.59 | 70.4 |
| VkB7_VH3 | 0.00 | 0.0 | 0.00 | 0 |
| VkC3_VH3 | 0.50 | 3.8 | 15.10 | 70.2 |
| VkC8_VH3 | 0.32 | 2.1 | 8.25 | 61.2 |
| VkC19_VH3 | 0.19 | 1.0 | 3.90 | 62.4 |
| VkB1_VH5 | 0.64 | 4.6 | 18.53 | 68.4 |
| VkB3_VH5 | 1.02 | 7.1 | 28.53 | 70.4 |
| VkB7_VH5 | 0.13 | 0.7 | 2.65 | 68.9 |
| VkC3_VH5 | 0.91 | 6.8 | 27.23 | 68.7 |
| VkC8_VH5 | 1.14 | 8.5 | 34.19 | 62.4 |
| VkC19_VH5 | 0.81 | 6.1 | 24.43 | 66.3 |
| VkB1_VH9 | 1.11 | 7.8 | 31.06 | 68.7 |
| VkB3_VH9 | 0.84 | 7.2 | 28.60 | 68.2 |
| VkB7_VH9 | 0.16 | 0.8 | 3.30 | 69.4 |
| VkC3_VH9 | 1.51 | 11.4 | 45.43 | 70.4 |
| VkC8_VH9 | 1.40 | 9.8 | 39.27 | 65.055 |
| VkC19_VH9 | 1.05 | 7.9 | 31.59 | 65.94 |
| VkB1_VH1 RVT | 0.95 | 7.2 | 28.64 | 71.385 |
| VkB3_VH1 RVT | 0.77 | 5.8 | 23.09 | 75.39 |
| VkB7_VH1 RVT | 0.12 | 0.5 | 1.95 | 72.715 |
| VkC3_VH1 RVT | 0.96 | 7.2 | 28.82 | 75.42 |
| VkC8_VH1 RVT | 0.25 | 1.8 | 7.00 | 71.055 |
| VkC19_VH1 RVT | 0.90 | 6.7 | 26.87 | 71.22 |
| VkB1_VH1 | 0.68 | 5.0 | 20.04 | 70.97 |
| VkB3_VH1 | 1.03 | 7.7 | 30.62 | 72.3 |
| VkB7_VH1 | 0.12 | 0.7 | 2.66 | 72.67 |
| VkC3_VH1 | 0.52 | 3.9 | 15.51 | 74.9 |
| VkC8_VH1 | 1.03 | 7.7 | 30.99 | 70.9 |
| VkC19_VH1 | 0.59 | 4.5 | 17.91 | 70.93 |
| VkB1_VH2 | 0.81 | 5.4 | 21.47 | 69.43 |
| VkB3_VH2 | 0.64 | 4.5 | 17.87 | 70.595 |
| VkB7_VH2 | 0.00 | 0.0 | 0.00 | 0 |
| VkC3_VH2 | 0.84 | 5.9 | 23.44 | 68.725 |
| VkC8_VH2 | 1.21 | 9.1 | 36.32 | 67.17 |
| VkC19_VH2 | 0.00 | 0.0 | 0.00 | 0 |

| <0.5 mg/ml | < 10 mg | < 68 °C |
|---|---|---|
| 0.5 - 1 mg/ml | 10 - 20 mg | 68 - 72 °C |
| > 1 mg/ml | > 20 mg | > 72 °C |

Figure 17b
Data for purification w/o Isopropanol

| Construct | conc [mg/ml] | yield [mg] | yield [mg/L] | Tm [°C] |
|---|---|---|---|---|
| VkB1_VH3 | 0.27 | 1.8 | 7.20 | 71.6 |
| VkB3_VH3 | 0.71 | 5.0 | 19.91 | 69.9 |
| VkB7_VH3 | 0.00 | 0.0 | 0.00 | 0 |
| VkC3_VH3 | 0.97 | 7.2 | 28.81 | 70.7 |
| VkC8_VH3 | 0.49 | 3.2 | 12.64 | 61.1 |
| VkC19_VH3 | 0.07 | 0.5 | 1.84 | 62.4 |
| VkB1_VH5 | 0.07 | 0.1 | 0.53 | 68.6 |
| VkB3_VH5 | 0.90 | 4.9 | 19.79 | 70.2 |
| VkB7_VH5 | 0.12 | 0.6 | 2.39 | 68.7 |
| VkC3_VH5 | 1.12 | 10.1 | 40.25 | 69.4 |
| VkC8_VH5 | 1.18 | 11.2 | 44.96 | 62.6 |
| VkC19_VH5 | 1.14 | 10.8 | 43.38 | 66.1 |
| VkB1_VH9 | 0.73 | 5.5 | 21.90 | 68.7 |
| VkB3_VH9 | 1.11 | 7.7 | 30.95 | 68.7 |
| VkB7_VH9 | 0.16 | 1.2 | 4.83 | 70.2 |
| VkC3_VH9 | 1.18 | 8.9 | 35.44 | 70.2 |
| VkC8_VH9 | 1.00 | 9.0 | 35.91 | 65.61 |
| VkC19_VH9 | 0.87 | 7.8 | 31.30 | 65.86 |
| VkB1_VH1 RVT | 0.88 | 8.0 | 31.86 | 71.42 |
| VkB3_VH1 RVT | 0.64 | 6.1 | 24.30 | 75.745 |
| VkB7_VH1 RVT | 0.13 | 0.7 | 2.68 | 72.755 |
| VkC3_VH1 RVT | 1.05 | 7.9 | 31.47 | 75.83 |
| VkC8_VH1 RVT | 0.57 | 4.3 | 17.01 | 71.39 |
| VkC19_VH1 RVT | 0.95 | 7.1 | 28.60 | 72.595 |
| VkB1_VH1 | 0.64 | 5.8 | 23.19 | 72.18 |
| VkB3_VH1 | 0.83 | 5.8 | 23.12 | 74.455 |
| VkB7_VH1 | 0.12 | 0.7 | 2.69 | 75.3 |
| VkC3_VH1 | 1.00 | 7.5 | 29.90 | 74.9 |
| VkC8_VH1 | 1.16 | 8.7 | 34.83 | 70.9 |
| VkC19_VH1 | 0.75 | 5.6 | 22.52 | 71.01 |
| VkB1_VH2 | 0.59 | 5.0 | 20.03 | 68.43 |
| VkB3_VH2 | 0.73 | 5.4 | 21.51 | 70.84 |
| VkB7_VH2 | 0.55 | 5.3 | 21.07 | 70.51 |
| VkC3_VH2 | 0.91 | 7.7 | 30.81 | 70.51 |
| VkC8_VH2 | 0.64 | 6.4 | 25.50 | 65.98 |
| VkC19_VH2 | 0.08 | 0.5 | 2.17 | 63.66 |

| <0.5 mg/ml | | < 10 mg | < 68 °C |
|---|---|---|---|
| 0.5 - 1 mg/ml | | 10 - 20 mg | 68 - 72 °C |
| > 1 mg/ml | | > 20 mg | > 72 °C |

Figure 20

| | 89 T8 | | 90 | | 91 T9 | | 92 T10 | | 93 T11 | | 94 T12 | | 95 | | 96 T13 | |
|---|---|---|---|---|---|---|---|---|---|---|---|---|---|---|---|---|
| | F | P | F | P | F | P | F | P | F | P | F | P | F | P | F | P |
| A | 0.9 | 1.6 | | | 2.9 | 2.6 | 0.9 | 1.6 | 0.8 | 1.6 | 1.8 | 1.8 | | | 1.2 | 1.6 |
| C | | | | | | | | | | | | | | | | |
| D | 0.7 | 1.6 | | | 2.1 | 2.6 | 1.5 | 1.6 | 1.6 | 1.6 | 1.1 | 1.8 | | | 0.8 | 1.6 |
| E | 1.7 | 1.6 | | | 3.5 | 2.6 | 2.5 | 1.6 | 18.7 | 16.6 | 1.9 | 1.8 | | | 3.0 | 1.6 |
| F | 10.6 | 11.6 | | | 2.7 | 2.6 | 1.8 | 1.6 | 1.6 | 1.6 | 13.9 | 11.8 | | | 14.8 | 11.6 |
| G | 0.9 | 1.6 | | | 16.4 | 22.6 | 0.8 | 1.6 | 0.5 | 1.6 | 0.8 | 1.8 | | | 1.2 | 1.6 |
| H | 2.4 | 1.6 | | | 3.6 | 2.6 | 1.5 | 1.6 | 31.1 | 26.6 | 2.1 | 1.8 | | | 1.9 | 1.6 |
| I | 1.2 | 1.6 | | | 2.0 | 2.6 | 1.2 | 1.6 | 1.0 | 1.6 | 1.6 | 1.8 | | | 1.5 | 1.6 |
| K | 0.9 | 1.6 | 0.1 | | 2.9 | 2.6 | 1.7 | 1.6 | 1.1 | 1.6 | 1.3 | 1.8 | | | 1.7 | 1.6 |
| L | 1.3 | 1.6 | | | 1.2 | 2.6 | 1.9 | 1.6 | 1.3 | 1.6 | 6.6 | 11.8 | 0.1 | | 11.4 | 21.6 |
| M | 1.5 | 1.6 | | | 3.7 | 2.6 | 1.8 | 1.6 | 1.6 | 1.6 | 2.5 | 1.8 | | | 2.7 | 1.6 |
| N | 0.7 | 1.6 | | | 1.9 | 2.6 | 12.4 | 16.6 | 1.3 | 1.6 | 1.0 | 1.8 | | | 1.4 | 1.6 |
| P | 1.5 | 1.6 | | | 2.5 | 2.6 | 1.3 | 1.6 | 0.9 | 1.6 | 0.7 | 1.8 | 99.9 | 100 | 1.6 | 11.6 |
| Q | 56.1 | 51.6 | 99.9 | 100 | 3.2 | 2.6 | 1.8 | 1.6 | 1.6 | 1.6 | 1.1 | 1.8 | | | 2.3 | 1.6 |
| R | 0.6 | 1.6 | | | 1.4 | 2.6 | 1.1 | 1.6 | 1.3 | 1.6 | 1.3 | 1.8 | | | 1.0 | 1.6 |
| S | 11.0 | 11.6 | | | 21.0 | 22.6 | 28.2 | 31.6 | 27.6 | 31.6 | 1.6 | 1.8 | | | 1.4 | 1.6 |
| T | 1.2 | 1.6 | | | 2.9 | 2.6 | 17.4 | 16.6 | 1.4 | 1.6 | 1.2 | 1.8 | | | 1.1 | 1.6 |
| V | 2.3 | 1.6 | | | 5.0 | 2.6 | 2.9 | 1.6 | 2.7 | 1.6 | 25.6 | 21.8 | | | 2.4 | 1.6 |
| W | 3.0 | 1.6 | | | 4.3 | 2.6 | 1.8 | 1.6 | 1.6 | 1.6 | 2.5 | 1.8 | | | 3.9 | 1.6 |
| Y | 1.5 | 1.6 | | | 16.8 | 12.6 | 17.4 | 11.6 | 2.1 | 1.6 | 31.4 | 26.8 | | | 44.8 | 31.6 |

Figure 21

| | 95-96 T1 | | 97 T2 | | 98-100a T3 | | 100b T4 | | 100m T5 | | 100n T6 | | 101 W1 | | 102 T7 | |
|---|---|---|---|---|---|---|---|---|---|---|---|---|---|---|---|---|
| | F | P | F | P | F | P | F | P | F | P | F | P | F | P | F | P |
| A | 1.3 | 1.6 | 0.9 | 1.6 | 1.8 | 2.1 | 2.1 | 2.6 | 19.6 | 22.6 | 0.7 | 1.1 | 15.4 | 20.0 | | |
| C | | | | | | | | | | | | | | | | |
| D | 9.7 | 11.6 | 3.4 | 6.6 | 5.6 | 7.1 | 1.0 | 2.6 | 1.5 | 2.6 | 0.5 | 1.1 | 84.6 | 80.0 | | |
| E | 1.8 | 1.6 | 0.6 | 1.6 | 1.7 | 2.1 | 2.8 | 2.6 | 3.9 | 2.6 | 0.5 | 1.1 | | | | |
| F | 1.9 | 1.6 | 2.1 | 1.6 | 2.9 | 2.1 | 3.4 | 2.6 | 2.6 | 2.6 | 83.5 | 61.1 | | | | |
| G | 16.7 | 21.6 | 7.5 | 11.6 | 10.2 | 17.1 | 7.7 | 12.6 | 1.0 | 2.6 | 0.3 | 1.1 | | | | |
| H | 1.2 | 1.6 | 2.4 | 1.6 | 1.9 | 2.1 | 2.3 | 2.6 | 2.8 | 2.6 | 0.7 | 1.1 | | | | |
| I | 1.2 | 1.6 | 1.3 | 1.6 | 0.9 | 2.1 | 1.3 | 2.6 | 1.3 | 2.6 | 0.5 | 1.1 | | | | |
| K | 2.5 | 1.6 | 2.4 | 1.6 | 2.8 | 2.1 | 3.3 | 2.6 | 5.4 | 2.6 | 0.7 | 1.1 | | | | |
| L | 1.2 | 1.6 | 1.9 | 1.6 | 2.5 | 2.1 | 2.6 | 2.6 | 2.0 | 2.6 | 0.7 | 1.1 | | | | |
| M | 1.0 | 1.6 | 1.1 | 1.6 | 2.0 | 2.1 | 1.6 | 2.6 | 0.7 | 2.6 | 6.2 | 21.1 | | | | |
| N | 2.0 | 1.6 | 1.7 | 1.6 | 8.4 | 7.1 | 2.1 | 2.6 | 2.5 | 2.6 | 0.7 | 1.1 | | | | |
| P | 0.5 | 1.6 | 0.6 | 1.6 | 0.9 | 2.1 | 1.0 | 2.6 | 1.5 | 2.6 | 0.2 | 1.1 | | | | |
| Q | 0.5 | 1.6 | 0.6 | 1.6 | 0.8 | 2.1 | 1.3 | 2.6 | 1.0 | 2.6 | 0.8 | 1.1 | | | | |
| R | 5.5 | 11.6 | 2.8 | 6.6 | 4.0 | 7.1 | 1.3 | 2.6 | 1.1 | 2.6 | 0.5 | 1.1 | | | | |
| S | 14.2 | 11.6 | 8.8 | 6.6 | 25.0 | 17.1 | 15.5 | 12.6 | 4.1 | 2.6 | 1.8 | 1.1 | | | | |
| T | 2.8 | 1.6 | 2.4 | 1.6 | 3.1 | 2.1 | 2.6 | 2.6 | 3.4 | 2.6 | 0.5 | 1.1 | | | | |
| V | 3.2 | 1.6 | 1.5 | 1.6 | 2.2 | 2.1 | 3.3 | 2.6 | 2.8 | 2.6 | 0.8 | 1.1 | | | | |
| W | 0.7 | 1.6 | | | 0.8 | 2.1 | 0.2 | 2.6 | 0.7 | 2.6 | 0.2 | 1.1 | | | 17.5 | 20.0 |
| Y | 32.2 | 21.6 | 57.7 | 41.6 | 22.4 | 17.1 | 44.4 | 32.6 | 42.2 | 32.6 | 1.3 | 1.1 | | | 82.5 | 80.0 |

Figure 22

| | 50, 53, 56, 58 MMT-1 | | 51 | | 52 MMT-2 | | 52a | | 54 MMT-3 | | 55 MMT-4 | | 57 MMT-5 | | 59 | | 60 | | 61 W1 | | 62 | | 63 | | 64 | |
|---|---|---|---|---|---|---|---|---|---|---|---|---|---|---|---|---|---|---|---|---|---|---|---|---|---|---|
| | Aver F | P | F | P | F | P | F | P | F | P | F | P | F | P | F | P | F | P | F | P | F | P | F | P | F | P |
| A | 3.2 | 5.3 | | | | | | | 2.2 | 1.5 | | | | 1.0 | | | | | | | | | | | | |
| C | 4.0 | 5.3 | | | | | | | | | | | | | | | | | | | | | | | | |
| D | 5.1 | 5.3 | | | 39.8 | 50.0 | | | 8.6 | 11.5 | 8.6 | 10.0 | 2.2 | 1.0 | | | | | | | | | | | | |
| E | 5.6 | 5.3 | | | | | | | 3.2 | 1.5 | | | 3.2 | 1.0 | | | | | | | | | | | | |
| F | 3.2 | 5.3 | 100 | 100 | | | | | 1.1 | 1.5 | | | 1.1 | 1.0 | | | | | | | | | | | | |
| G | 8.3 | 5.3 | | | | | | | 1.1 | 1.5 | | | 2.2 | 1.0 | | | | | 62.4 | 60.0 | | | | | | |
| H | 5.4 | 5.3 | | | 18.3 | 10.0 | | | 2.2 | 1.5 | 73.1 | 80.0 | 10.8 | 11.0 | | | | | | | | | | | | |
| I | 3.5 | 5.3 | | | | | | | | 1.5 | | | 1.1 | 1.0 | | | | | | | | | 100 | 100 | | |
| K | 5.4 | 5.3 | | | | | 100 | 100 | 1.1 | 1.5 | | | 1.1 | 1.0 | | | | | | | | | | | 100 | 100 |
| L | 8.1 | 5.3 | | | | | | | 2.2 | 1.5 | | | | | | | | | | | | | | | | |
| M | 3.2 | 5.3 | | | | | | | 2.2 | 1.5 | | | 3.2 | 1.0 | | | | | | | 100 | 100 | | | | |
| N | 5.4 | 5.3 | | | 21.5 | 20.0 | | | 7.5 | 11.5 | | | | 1.0 | | | 100 | 100 | | | | | | | | |
| P | 5.1 | 5.3 | | | | | | | 1.1 | 1.5 | | | 1.1 | 1.0 | | | | | | | | | | | | |
| Q | 4.3 | 5.3 | | | | | | | | 1.5 | 18.3 | 10.0 | | 1.0 | | | | | | | | | | | | |
| R | 5.9 | 5.3 | | | | | | | 61.3 | 51.5 | | | | | | | | | 37.6 | 40.0 | | | | | | |
| S | 5.6 | 5.3 | | | | | | | 1.1 | 1.5 | | | 2.2 | 1.0 | | | | | | | | | | | | |
| T | 6.7 | 5.3 | | | | | | | 1.1 | 1.5 | | | 69.9 | 71.0 | 100 | 100 | | | | | | | | | | |
| V | 5.1 | 5.3 | | | | | | | 1.1 | 1.5 | | | 2.2 | 1.0 | | | | | | | | | | | | |
| W | 6.7 | 5.3 | | | 20.4 | 20.0 | | | 1.1 | 1.5 | | | | | | | | | | | | | | | | |
| Y | 6.7 | 5.3 | | | | | | | 3.2 | 1.5 | | | | 1.0 | | | | | | | | | | | | |

Figure 23

| | 50 | | 51 | | 52 | | 53 | | 54 | | 55 | | 56 | | 57 | | 58 | | 59 | | 60 | | 61 | | 62 | | 63 | | 64 | | 65 | |
|---|---|---|---|---|---|---|---|---|---|---|---|---|---|---|---|---|---|---|---|---|---|---|---|---|---|---|---|---|---|---|---|---|
| | W2 | | | | MMT-6 | | MMT-7 | | MMT-8 | | | | MMT-9 | | | | MMT-1 | | | | | | MMT-10 | | | | | | | | | |
| | F | P | F | P | F | P | F | P | F | P | F | P | F | P | F | P | F | P | F | P | F | P | F | P | F | P | F | P | F | P | F | P |
| A | | | | | | 1.6 | 20.2 | 17.1 | 1.1 | 1.6 | | | 2.1 | 2.6 | | | 2.1 | 5.3 | | | | | | | | | | | | | | |
| C | | | | | 4.3 | 1.6 | 1.1 | 2.1 | 7.4 | 11.6 | | | 1.1 | 2.6 | | | 2.1 | 5.3 | | | | | | | | | | | | | | |
| D | | | | | | 1.6 | 3.2 | 2.1 | | 1.6 | | | 4.3 | 2.6 | | | 10.6 | 5.3 | | | | | | | | | | | | | | |
| E | | | | | | 1.6 | 2.1 | 2.1 | 2.1 | 1.6 | | | 2.1 | 2.6 | | | 2.1 | 5.3 | | | | | | | | | | | | | | |
| F | | | | | | 1.6 | 12.8 | 17.1 | 66.0 | 61.6 | | | | 2.6 | | | 4.3 | 5.3 | | | | | | | | | | | | | | |
| G | | | | | | 1.6 | 6.4 | 2.1 | 2.1 | 1.6 | 100.0 | 100.0 | 4.3 | 2.6 | | | 10.6 | 5.3 | | | | | | | | | | | | | | |
| H | | | | | 1.1 | 1.6 | 1.1 | 2.1 | 2.1 | 1.6 | | | | 2.6 | | | 3.2 | 5.3 | | | | | | | | | | | | | | |
| I | | | | | | 1.6 | 2.1 | 2.1 | | 1.6 | | | 3.2 | 2.6 | | | 4.3 | 5.3 | | | | | | | | | | | | | | |
| K | | | 100.0 | 100.0 | 1.1 | 1.6 | 2.1 | 2.1 | 2.1 | 1.6 | | | 4.3 | 2.6 | | | 2.1 | 5.3 | | | | | | | | | | | | | | |
| L | | | | | 1.1 | 1.6 | 2.1 | 2.1 | 2.1 | 1.6 | | | | 2.6 | | | 5.3 | 5.3 | | | | | | | | | | | | | | |
| M | | | | | | 1.6 | 2.1 | 2.1 | | 1.6 | | | 4.3 | 2.6 | | | 1.1 | 5.3 | | | | | | | | | | | | | | |
| N | 25.5 | 20.0 | | | 2.1 | 1.6 | 2.1 | 2.1 | 2.1 | 1.6 | | | 2.1 | 2.6 | | | 5.3 | 5.3 | | | 33.0 | 40.0 | 100.0 | 100.0 | | | | | | | | |
| P | | | | | 4.3 | 1.6 | 2.1 | 2.1 | 1.1 | 1.6 | | | 2.1 | 2.6 | | | 8.5 | 5.3 | | | | | | | | | | | | | | |
| Q | | | | | | 1.6 | 16.0 | 17.1 | 1.1 | 1.6 | | | 2.1 | 2.6 | | | 7.4 | 5.3 | | | | | | | 100.0 | 100.0 | | | | | | |
| R | | | | | | 1.6 | 17.0 | 17.1 | 1.1 | 1.6 | | | 58.5 | 52.6 | 100.0 | 100.0 | 4.3 | 5.3 | | | | | | | | | | | | | | |
| S | | | | | 2.1 | 1.6 | 1.1 | 2.1 | 1.1 | 1.6 | | | 4.3 | 2.6 | | | 3.2 | 5.3 | | | 67.0 | 60.0 | | | | | 98.9 | 100.0 | | | | |
| T | | | | | 4.3 | 1.6 | 4.3 | 2.1 | 1.1 | 1.6 | | | 4.3 | 2.6 | | | 8.5 | 5.3 | | | | | | | | | | 1.1 | | | | |
| V | 74.5 | 80.0 | | | 76.6 | 71.6 | 1.1 | 2.1 | 4.3 | 1.6 | | | | 2.6 | | | 9.6 | 5.3 | | | | | | | | | | | | | | |
| W | | | | | | | | | | | | | | | | | | | | | | | | | | | | | | | | |
| Y | | | | | 2.1 | 1.6 | 2.1 | 2.1 | 4.3 | 1.6 | | | 5.3 | 2.6 | | | 5.3 | 5.3 | 100.0 | 100.0 | | | | | | | | | 100.0 | 100.0 | | |

Figure 24

| | 50 MMT-1 | | 51 | | 52 MMT-11 | | 55 MMT-12 | | 53 MMT-13 | | 54 W3 | | 56 MMT-14 | | 57 MMT-15 | | 58 | | 59 | | 60 W4 | | 61 | | 62 | | 63 | | 64 | | 65 | |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| | F | P | F | P | F | P | F | P | F | P | F | P | F | P | F | P | F | P | F | P | F | P | F | P | F | P | F | P | F | P | F | P |
| A | 6.0 | 5.3 | | | 2.4 | 4.2 | 1.2 | 3.2 | 7.2 | 4.7 | | | 2.4 | 3.2 | 2.4 | 3.2 | | | | | 39.8 | 40.0 | | | | | | | | | | |
| C | 4.8 | 5.3 | | | | 4.2 | | 3.2 | | 4.7 | | | | 3.2 | | 3.2 | | | | | | | | | | | | | | | | |
| D | 6.0 | 5.3 | | | 3.6 | 4.2 | 4.2 | 3.2 | 3.6 | 4.7 | | | 4.8 | 3.2 | | 3.2 | | | | | | | 100.0 | 100.0 | | | | | | | | |
| E | 8.4 | 5.3 | | | 8.4 | 4.2 | 2.4 | 3.2 | 8.4 | 4.7 | | | | 3.2 | 4.8 | 3.2 | | | | | | | | | | | | | | | | |
| F | 2.4 | 5.3 | | | 3.6 | 4.2 | 2.4 | 3.2 | 3.6 | 4.7 | 65.1 | 70.0 | | 3.2 | 1.2 | 3.2 | | | | | | | | | | | | | | | | |
| G | 7.2 | 5.3 | 100.0 | 100.0 | | 4.2 | 12.7 | 23.2 | 10.8 | 14.7 | | | 3.6 | 3.2 | 3.6 | 3.2 | | | | | | | | | | | | | | | | |
| H | 3.6 | 5.3 | | | 7.2 | 4.2 | 4.2 | 3.2 | 7.2 | 4.7 | | | 3.6 | 3.2 | 4.8 | 3.2 | | | | | | | | | | | | | | | 100.0 | 100.0 |
| I | 3.6 | 5.3 | | | 3.6 | 4.2 | 2.4 | 3.2 | 3.6 | 4.7 | | | 2.4 | 3.2 | 14.5 | 13.2 | | | | | | | | | | | | | | | | |
| K | 3.6 | 5.3 | | | 1.2 | 4.2 | 2.4 | 3.2 | 6.0 | 4.7 | | | 1.2 | 3.2 | 1.2 | 3.2 | | | | | | | | | | | | | | | | |
| L | 7.2 | 5.3 | | | 2.4 | 4.2 | 2.4 | 3.2 | 2.4 | 4.7 | | | 2.4 | 3.2 | 7.2 | 3.2 | | | | | | | | | | | | | 100.0 | 100.0 | | |
| M | 3.6 | 5.3 | | | 7.2 | 4.2 | 4.8 | 3.2 | 3.6 | 4.7 | | | 3.6 | 3.2 | 3.6 | 3.2 | | | | | | | | | | | | | | | | |
| N | 6.0 | 5.3 | | | 2.4 | 4.2 | 2.4 | 3.2 | 3.6 | 4.7 | | | 18.1 | 23.2 | 3.6 | 3.2 | | | | | | | | | | | | | | | | |
| P | 3.6 | 5.3 | | | 3.6 | 4.2 | 0.6 | 3.2 | 7.2 | 4.7 | | | 1.2 | 3.2 | 10.8 | 3.2 | | | | | 60.2 | 60.0 | | | | | | | | | | |
| Q | 7.2 | 5.3 | | | 6.0 | 4.2 | 8.4 | 3.2 | 7.2 | 4.7 | | | 8.4 | 3.2 | | 3.2 | | | | | | | | | 100.0 | 100.0 | | | | | | |
| R | 2.4 | 5.3 | | | 2.4 | 4.2 | 2.4 | 3.2 | 3.6 | 4.7 | 34.9 | 30.0 | 2.4 | 3.2 | 2.4 | 3.2 | | | | | | | | | | | | | | | | |
| S | 4.8 | 5.3 | | | 25.3 | 24.2 | 27.1 | 23.2 | 1.2 | 4.7 | | | 3.6 | 3.2 | 1.2 | 3.2 | | | | | | | | | | | | | | | | |
| T | 7.2 | 5.3 | | | 6.0 | 4.2 | 4.8 | 3.2 | 2.4 | 4.7 | | | 1.2 | 3.2 | 26.5 | 33.2 | | | | | | | | | | | 100.0 | 100.0 | | | | |
| V | 6.0 | 5.3 | | | 7.2 | 4.2 | 6.0 | 3.2 | 9.6 | 4.7 | | | 4.8 | 3.2 | 9.6 | 3.2 | | | | | | | | | | | | | | | | |
| W | 8.4 | 5.3 | | | 3.6 | 4.2 | 4.2 | 3.2 | 4.8 | 4.7 | | | 2.4 | 3.2 | | 3.2 | | | | | | | | | | | | | | | | |
| Y | 1.2 | 5.3 | | | 3.6 | 4.2 | 4.8 | 3.2 | 3.6 | 4.7 | | | 31.3 | 23.2 | 2.4 | 3.2 | 100.0 | 100.0 | 100.0 | 100.0 | | | | | | | | | | | | |

| Kabat No. | nearst germline | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | | | | | | | | | | | | | | | | | | | |
| mVLB1 (BALB/c) | D00081\|IGKV1-117*01\|Mus | D | I | L | M | T | Q | T | P | L | S | L | P | V | S | L | G | D | Q |
| mVLB3 (BALB/c) | K02159\|IGKV3-12*01\|Mus | D | I | V | L | T | Q | S | P | A | S | L | A | V | S | L | G | Q | R |
| mVLB7 (BALB/c) | AF044198\|IGKV7-33*01\|Mus | D | I | V | M | T | Q | S | P | T | F | L | A | V | T | A | S | Q | K |
| mVLC3 (C75BL6) | Y15968\|IGKV3-4*01\|Mus | D | I | V | L | T | Q | S | P | A | S | L | A | V | S | L | G | Q | R |
| mVLC6 (C75BL6) | AJ235947\|IGKV8-28*01\|Mus | D | I | V | M | T | Q | S | P | S | S | L | S | V | S | A | G | E | K |
| mVLC19 (C75BL6) | AJ235935\|IGKV19-93*01\|Mus | D | I | Q | M | T | Q | S | P | S | S | L | A | A | S | L | G | G | K |
| rVL1 | consensus group1 | D | I | V | M | T | Q | S | P | S | S | L | S | V | S | A | G | E | K |
| rVL2 | consensus group2 | D | I | Q | M | T | Q | S | P | S | S | L | S | A | S | L | G | D | R | mouse/rat

Figure 27b

| | | | 19 | 20 | 21 | 22 | 23 | 24 | 25 | 26 | 27 | 28 | 29 | 30 | 30a | 30b | 30c | 30d | 30e | 30f | 31 | 32 | 33 | 34 |
|---|---|---|---|---|---|---|---|---|---|---|---|---|---|---|---|---|---|---|---|---|---|---|---|---|
| LCDR1 | LCDR1 | LCDR1 | A | S | I | S | C | R | S | S | Q | S | I | V | H | S | N | ■ | ■ | G | N | Y | L | E |
| | | | A | T | I | S | C | R | A | S | K | S | V | S | T | S | G | ■ | ■ | Y | S | Y | M | H |
| | | | V | T | I | S | C | T | A | S | E | S | L | Y | S | S | K | H | K | V | H | Y | L | A |
| | | | A | T | I | S | C | K | A | S | Q | S | V | D | Y | D | G | ■ | ■ | D | N | Y | M | N |
| | | | V | T | M | S | C | K | S | S | Q | S | L | L | N | S | G | N | Q | K | Q | Y | L | A |
| | | | V | T | ■ | T | C | K | A | S | Q | D | I | N | K | ■ | ■ | ■ | ■ | ■ | ■ | Y | I | A |
| | | | V | S | ■ | S | C | R | S | S | Q | S | L | V | H | S | D | G | K | K | T | Y | L | N |
| | | | V | T | ■ | E | C | K | A | S | Q | N | I | Y | K | ■ | ■ | ■ | ■ | ■ | ■ | Y | L | A |

Figure 27c

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| mVLB1 | GAT | ATC | CTG | ATG | ACC | CAG | ACC | CCA | CTG | AGC | CTG | CCA | GTT | AGC | CTG | GGC | GAT | CAG |
| mVLB3 | GAT | ATC | GTG | CTG | ACC | CAG | ACC | CCA | AGC | CCA | CTG | GCC | GTG | AGC | CTG | GGC | CAA | CGC |
| mVLB7 | GAT | ATC | GTG | ATG | ACC | CAG | AGC | CCA | AGC | TTT | CTG | GCC | GTG | ACC | GCC | AGC | AAA | AAA |
| mVLC3 | GAT | ATC | GTG | CTG | ACC | CAG | AGC | CCA | GCG | AGC | CTG | GCC | GTG | AGC | CTG | GGC | CAA | CGC |
| mVLC8 | GAT | ATC | GTG | ATG | ACC | CAG | AGC | CCA | AGC | AGC | CTG | AGC | GTT | AGC | GCA | GGC | GAA | AAA |
| mVLC19 | GAT | ATC | CAG | ATG | ACC | CAG | AGC | CCA | AGC | AGC | CTG | AGC | GCC | AGC | CTG | GGC | GGC | AAA |
| rVL1 | GAT | ATC | GTG | ATG | ACC | CAG | TCT | CCG | AGC | AGC | CTG | GCC | GTT | AGC | GCG | GGT | GAA | AAA |
| rVL2 | GAT | ATC | CAG | ATG | ACC | CAG | AGC | CCG | AGC | AGC | CTG | AGC | GCG | AGC | CTG | GGT | GAT | CGT |

Either one of two amino acids (T or V) can be found in these residues (Vκ1 and Vκ3 only)
Sequence region retrieved from the Sequence Analysis Software (SAS)
Position of the diversified region
Potential length variability
No amino acid at this position mouse/rat Kabat CDRs
Kabat No

Figure 28b

| | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|---|---|---|---|---|---|---|---|---|
| | S | G | S | G | S | G | T | D | F | T | L | K | I | S | R | V | E | A | E | D | L | G | V | Y | Y |
| | S | G | S | G | S | G | T | D | F | T | L | N | I | H | P | V | E | E | E | D | A | A | V | Y | Y |
| | T | G | S | G | S | G | T | D | F | T | L | T | I | S | S | V | Q | V | E | D | L | T | H | Y | Y |
| | S | G | S | G | S | G | T | D | F | T | L | N | I | H | P | V | E | E | E | D | A | A | T | Y | Y |
| | T | G | S | G | S | G | T | D | F | T | L | T | I | S | S | V | Q | A | E | D | L | A | V | Y | Y |
| | S | G | S | G | S | G | R | D | Y | S | F | S | I | S | N | L | E | P | E | D | I | A | T | Y | Y |
| | S | G | S | G | S | G | T | D | F | T | L | K | I | S | R | V | E | A | E | D | L | G | V | Y | Y |
| | S | G | S | G | S | G | T | D | Y | T | L | T | I | S | S | L | Q | P | E | D | V | A | T | Y | F |

Figure 29a

| 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|
| K | I | S | R | V | E | A | E | D | L | G | V | Y | Y | C |
| N | I | H | P | V | E | E | E | D | A | A | T | Y | Y | C |
| T | I | S | S | V | Q | V | E | D | L | T | H | Y | Y | C |
| N | I | I | P | V | E | L | E | D | A | A | T | Y | Y | C |
| T | I | S | S | V | Q | A | E | D | L | A | T | Y | Y | C |
| S | I | S | N | L | E | P | E | D | I | A | V | Y | Y | C |
| K | I | S | R | V | E | A | E | D | L | G | V | Y | Y | C |
| T | I | S | S | L | Q | P | E | D | V | A | T | Y | F | C |

| | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|
| | | | | | | | | Bbsl | | | | | | | |
| | AAA | ATC | AGC | CGC | GTG | GAA | GCC | GAA | GAC | CTG | GGC | GTG | TAT | TAT | TGC |
| | AAC | ATC | CAC | CCG | GTG | GAA | GAA | GAA | GAC | GCC | GCC | ACC | TAT | TAT | TGC |
| | AGC | ATC | AGC | AGC | GTG | CAG | GTG | GAA | GAC | CTG | ACC | AAT | TAT | TAC | TGC |
| | AAC | ATC | GAC | CCG | GTG | GAA | GAA | GAA | GAC | GCC | GCC | CAT | TAT | TAT | TGC |
| | ACC | ATT | AGC | AGC | GTG | CAG | GCC | GAA | GAC | CTG | GCC | ACC | TAT | TAC | TGC |
| | ACC | ATT | AGC | AAC | GTG | GAA | CCG | GAA | GAC | ATC | GCC | GTG | TAT | TAT | TGC |
| | AGC | ATT | AGC | CGT | CTG | GAA | GCG | GAA | GAC | CTG | GGC | ACC | TAT | TAT | TGC |
| | AAA | ATT | AGC | TCT | GTG | GAA | GCG | GAA | GAC | CTG | GCC | GTG | TAT | TAT | TGC |
| | ACG | ATT | AGC | CTG | CTG | CAA | CCG | GAA | GAC | GTG | GCG | ACC | TAT | TTT | TGC |

Figure 30a

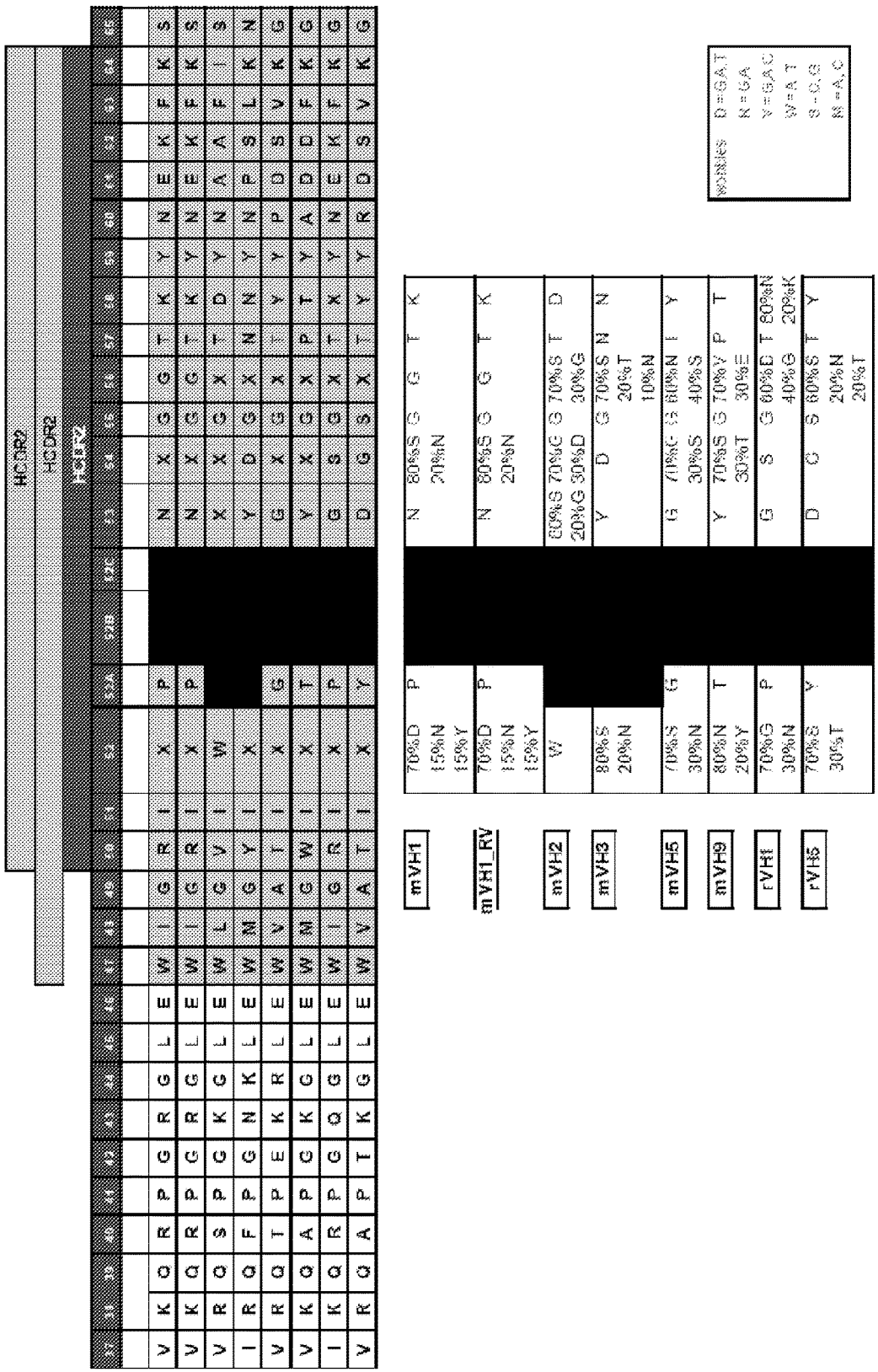

| | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 |
|---|---|---|---|---|---|---|---|---|---|---|---|---|---|---|---|---|---|---|---|---|---|---|---|---|---|---|---|---|---|
| | K | A | T | L | T | V | D | K | P | S | S | T | A | Y | M | Q | L | S | S | L | T | S | E | D | S | A | V | Y | Y |
| | | | T | L | T | V | D | K | P | S | S | T | A | Y | M | Q | L | S | S | L | T | S | E | D | S | A | V | Y | Y |
| | R | L | S | I | S | K | D | N | S | K | S | Q | V | F | F | K | M | N | S | L | Q | A | D | D | T | A | I | Y | Y |
| | R | I | I | T | R | D | T | T | A | K | N | Q | F | F | L | K | L | N | S | V | T | T | E | D | T | A | T | Y | Y |
| | R | F | T | S | S | R | D | N | S | K | N | T | L | Y | L | Q | M | S | S | L | R | S | E | D | T | A | M | Y | F |
| | R | F | A | F | S | L | E | T | S | A | S | T | A | Y | L | Q | I | N | N | L | K | N | E | D | T | A | T | Y | Y |
| | K | A | T | F | T | V | D | K | S | S | S | T | A | Y | M | Q | L | S | S | L | T | P | E | D | T | A | V | Y | Y |
| | R | F | T | I | S | R | D | N | A | K | S | T | L | Y | L | Q | M | D | S | L | R | S | E | D | T | A | T | Y | Y |

| 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 |
|---|---|---|---|---|---|---|---|---|---|---|---|---|---|---|---|---|---|---|---|---|---|---|---|---|---|---|---|---|
| AAA | GCC | AGC | CTG | ACC | GTG | GAT | AAA | CCG | AGC | ACC | GCC | TAT | ATG | CAA | CTG | AGT | AGC | | | CTG | ACC | AGC | GAA | GAT | AGC | GCC | GTG | TAT | TAT |
| CG | G | GTG | ACC | CTG | ACC | GTG | GAT | AAA | CCG | AGC | ACC | GCC | TAT | ATG | CAA | CTG | AGT | | | CTG | ACC | AGC | GAA | GAT | AGC | GCC | GTG | TAT | TAT |
| | | CGC | CTG | AGC | ATC | AGC | GAT | AAC | AGC | AAA | AGC | ACC | GCC | TTC | AAA | CTG | AAC | AGC | | | CTG | CAA | GCC | GAT | GAT | ACC | GCC | ATC | TAT | TAT |
| | | CGC | CTG | AGC | ATC | AGC | ACC | AAC | AGC | AAA | AGC | CAG | GTG | TTT | CTG | CTG | AAC | AGC | | | GTG | ACC | ACC | GAA | GAT | ACC | GCC | GCC | TAT | TAT |
| | | CGC | CTG | ATT | AGC | CGC | GAA | ACC | AGC | AAA | AAC | ACC | CAG | TTT | CTG | CTG | AAC | AGC | | | CTG | ACC | AGC | GAA | GAT | ACC | GCC | ACC | TAT | TAT |
| | | CGC | CTG | TTT | AGC | CTG | GAA | ACC | AGC | AAA | AGC | ACC | GCC | TAT | ATG | CTG | CAA | ATG | | | CTG | CGC | AGC | GAA | GAT | ACC | GCC | ATG | TAT | TTT |
| | | AAA | CTG | TTT | ACC | GAT | AAA | GTG | ACC | AGC | AGC | ACC | GCG | TAT | CTG | CAA | ATT | AAC | | | AAA | AAC | GAA | GAT | ACC | GCC | ACC | TAT | TAT | TAC |
| | | GCG | ACC | ATT | AGC | CGT | GAT | AAC | GCG | AAA | AGC | ACC | CTG | TAT | ATG | CAG | GTG | TCC | | | AGC | CCG | AGC | GAA | GAT | ACC | GCG | GGG | TAT | TAT |
| | | CGT | TTT | ACC | ATT | AGC | CGT | GAT | AAC | GCG | AAA | AAC | ACC | CTG | TAT | CTG | CAA | ATG | | | GAT | AGC | CGT | AGC | GAA | GAT | ACC | GCG | ACC | TAT | TAT |

Figure 31d

| | | 92 | 93 | 94 | 95 | 96 | 97 | 98 | 99 | 100 | 100a | 100b | 100c | 100d | 100e | 100f | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|
| HCDR3 | BstEII | | | | | | | | | | | | | | | | | | | StyI | | | | | | | | BlpI | |
| | | T | GC | GGG | X | X | X | X | X | X | X | X | X | X | X | X | X | TGG | GGC | CAA | GGC | ACC | ACC | CTG | ACC | GTT | AGC | TCA | AGT |
| | | T | GC | GGG | X | X | X | X | X | X | X | X | X | X | X | X | X | TGG | GGC | CAA | GGC | ACC | ACC | CTG | ACC | GTT | AGC | TCA | AGT |
| | | T | GC | GGG | X | X | X | X | X | X | X | X | X | X | X | X | X | TGG | GGC | CAA | GGC | ACC | ACC | CTG | ACC | GTT | AGC | TCA | AGT |
| | | T | GC | GGG | X | X | X | X | X | X | X | X | X | X | X | X | X | TGG | GGC | CAA | GGC | ACC | ACC | CTG | ACC | GTT | AGC | TCA | AGT |
| | | T | GC | GGG | X | X | X | X | X | X | X | X | X | X | X | X | X | TGG | GGC | CAA | GGC | ACC | ACC | CTG | ACC | GTT | AGC | TCA | AGT |
| | | T | GC | GGG | X | X | X | X | X | X | X | X | X | X | X | X | X | TGG | GGC | CAA | GGC | ACC | GTG | ATG | GTG | GTT | AGC | TCA | AGT |
| | | T | GC | GGG | X | X | X | X | X | X | X | X | X | X | X | X | X | TGG | GGC | CAA | GGC | ACC | GTG | ATG | GTG | ACG | GTT | AGC | TCA | AGT |
| | | T | GC | GGG | X | X | X | X | X | X | X | X | X | X | X | X | X | TGG | GGC | CAA | GGC | ACC | GTG | ATG | GTG | ACG | GTT | AGC | TCA | AGT |

Figure 36

|  |  |  |  |  | FW4 |  |  |  |  |  |  |  |
|---|---|---|---|---|---|---|---|---|---|---|---|---|
| Y | Y | W | Y | F | D | F | W | G | P | G | T | M | V | T | V | S | S |
|  | D | Y | Y | F | D | Y | W | G | Q | G | V | M | V | T | V | S | S |
|  | N | W | V | F | A | Y | W | G | Q | G | T | L | V | T | V | S | S |
|  | Y | Y | Y | V | M | D | A | W | G | Q | G | A | S | V | T | V | S | S |

Styl-site      Blpl-site

M13798|IGHJ1*01
X56791|IGHJ2*01
X56791|IGHJ3*01
X56791|IGHJ4*01

Figure 42

| | pMx31_Displ. | | pMx9 Fab_FH format | | | | | | IgG Format | | | | | |
|---|---|---|---|---|---|---|---|---|---|---|---|---|---|---|
| | MOR Display Rate (yes/no) | NVS Display Rate (yes/no) | NVS yield [mg/L] with Iso | NVS yield [mg/L] w/o Iso | MOR Yield [mg/l cult.] | SEC monomer portion [%] | Tm [°C] with iso | Tm [°C] w/o Iso | MOR titer rIgG2b [mg/l cult.] | MOR titer rIgG2c [mg/l cult.] | NVS titer IgG rIgG2b | Tm [°C] IgG DAS rIgG2b | NVS titer IgG rIgG2c | Tm [°C] IgG DAS rIgG2c |
| VL1_VH1 | | | 5.0 | 9.1 | 16 | 100 | 65.1 | 65.1 | n.a. | 0.8 | 23 | 66.5 | 10.2 | 70.2 |
| VL2_VH1 | | | 0.0 | 1.2 | 6 | 100 | - | 49.3 | 0.2 | 1.1 | 12.6 | 67.3 | 7.8 | 73.9 |
| VL1_VH5 | | | 12.6 | 19.9 | 13 | 100 | 67.7 | 67.9 | 0 | 13 | 21 | 67.9 | 25.4 | 72.5 |
| VL2_VH5 | | | 0.0 | 1.6 | 7 | 100 | - | 49.6 | 2.1 | 26 | 28.5 | 70.7 | 4.2 | 74.7 |

Figure 44

| 50 | 51 | 52  | 52a | 52b | 52c | 55 | 56  | 57 | 58 |
|----|----|-----|-----|-----|-----|----|-----|----|----|
| T  | I  | 70S | Y   | D   | G   | S  | 60S | T  | Y  |
|    |    | 30T |     |     |     |    | 20N |    |    |
|    |    | W17 |     |     |     |    | 20T |    |    |
|    |    |     |     |     |     |    | W18 |    |    | rVH5

SEQUENCE LISTING

```
<160> NUMBER OF SEQ ID NOS: 207

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Lys His Lys His Lys
1               5

<210> SEQ ID NO 3
<211> LENGTH: 5
<212> TYPE: PRT
<213> ORGANISM: Mus sp.

<400> SEQUENCE: 3

Thr Trp Pro Ser Glu
1               5

<210> SEQ ID NO 4
<211> LENGTH: 6
<212> TYPE: PRT
<213> ORGANISM: Mus sp.

<400> SEQUENCE: 4

Lys Thr Thr Pro Pro Ser
1               5

<210> SEQ ID NO 5
<211> LENGTH: 4
<212> TYPE: PRT
<213> ORGANISM: Mus sp.
```

-continued

<400> SEQUENCE: 5

Val Pro Arg Asp
1

<210> SEQ ID NO 6
<211> LENGTH: 11
<212> TYPE: PRT
<213> ORGANISM: Mus sp.

<400> SEQUENCE: 6

Trp Gly Gly Asp Gly Phe Tyr Ala Met Asp Tyr
1               5                   10

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: see specification as filed for detailed
      description of substitutions and preferred embodiments

<400> SEQUENCE: 7
ggtcgcggcc tcgagtggat tggccgcatt datccgaaca rcggcggcac caaatataac      60
gaa                                                                    63

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: see specification as filed for detailed
      description of substitutions and preferred embodiments

<400> SEQUENCE: 8
ggcaaaggtc tcgagtggct gggcgtgatt tggrgcgrcg gcrgcaccga ttataacgcc      60
gcc                                                                    63

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: see specification as filed for detailed
      description of substitutions and preferred embodiments

<400> SEQUENCE: 9
gaaaaacgcc tcgagtgggt ggcgaccatt arcggtggcr gtggcarcac ctattatcca      60
gatagc                                                                 66

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 10
gtggaagaag aagacgccgc cacctattat tgc                                33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggaagccg aagacctggg cgtgtattat tgc                                33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgcaggtgg aagacctgac ccattattac tgc                                33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgcaggccg aagacctggc cgtgtattac tgc                                33

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggccacgta cgtttcagtt ccagtttggt gcccgcacca aagg                    44

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggccacgta cgtttcagtt c                                             21

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
cgcgtggaag actgcgcgc                                              19

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cataacgaag acgccttggc ccca                                        24

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cataacgaag acgccttg                                               18

<210> SEQ ID NO 19
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 19
gaagacgccg ccacctatta ttgcnnncag nnnnnnnnnn nnccgnnnac ctttggcggt  60
ggcacca                                                           67
```

-continued

```
<210> SEQ ID NO 20
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 20
gaagacctgg gcgtgtatta ttgcnnncag nnnnnnnnnn nnccgnnnac ctttggcggt    60
ggcacca                                                              67

<210> SEQ ID NO 21
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
``` combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 21
gaagacctga cccattatta ctgcnnncag nnnnnnnnnn nnccgnnnac ctttggcggt    60
ggcacca                                                              67

<210> SEQ ID NO 22
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 22
gaagacctgg ccgtgtatta ctgcnnncag nnnnnnnnnn nnccgnnnac ctttggcggt    60
ggcacca                                                              67

<210> SEQ ID NO 23
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: This region discloses a, c, t or g in any
      combination except 'taa', 'tga' or 'tag'
<220> FEATURE:
<221> NAME/KEY: modified_base

```
<222> LOCATION: (22)..(24)
<223> OTHER INFORMATION: This region discloses a, c, t or g in any
      combination except 'taa', 'tga' or 'tag'
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (28)..(30)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (43)..(45)
<223> OTHER INFORMATION: This region discloses a, c, t or g in any
      combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<221> NAME/KEY: modified_base
<222> LOCATION: (49)..(49)
<223> OTHER INFORMATION: a, c, t or g
<220> FEATURE:
<221> NAME/KEY: modified_base
<222> LOCATION: (50)..(52)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 23
gtggaagact gcgcgcggnn nnnnnnnnnn nnnnnnnnnn nnnnnnnnnn nntggggcca      60
aggcgtct                                                              68

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtcgcggcc tcgagtgg                                                   18

<210> SEQ ID NO 25
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
gtttatccac ggtcagggtc acccggcttt tgaa                              34

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtttatccac ggtcagggtc acc                                          23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtgaccctg accgtggata aac                                          23

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggcaaaggtc tcgagtgg                                                18

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctgttatct ttgctgatgc tcaggcggct aataaa                            36

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctgttatct ttgctgatgc                                              20

<210> SEQ ID NO 31
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 31
gcatcagcaa agataacagc                                                    20

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaaaaacgcc tcgagtgg                                                      18

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgcggctaat ggtaaagcgg cctttcacgc t                                       31

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgcggctaat ggtaaagc                                                      18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctttaccat tagccgcg                                                      18

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgacgcccag cgcgcaataa ta                                                 22

<210> SEQ ID NO 37
<211> LENGTH: 18
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 37
ggccagggcc tcgagtgg                                                         18

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccacggtaaa ggtcgctttg cctttgaatt t                                          31

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccacggtaaa ggtcgctttg                                                       20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caaagcgacc tttaccgtgg                                                       20

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgacgcccag cgcgcagtaa tacacc                                                26

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
accaaaggtc tcgagtgg                                                         18

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
cacggctaat ggtaaaacgg cctttcacgc t                                31

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacggctaat ggtaaaacgg                                             20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgttttacc attagccgtg                                             20

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgacgcccag cgcgcaataa taggtc                                      26

<210> SEQ ID NO 47
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (43)..(45)
<223> OTHER INFORMATION: This region discloses a, c, t or g in any
      combination except 'taa', 'tga' or 'tag'
<220> FEATURE:

```
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<221> NAME/KEY: modified_base
<222> LOCATION: (49)..(51)
<223> OTHER INFORMATION: This region discloses a, c, t or g in any
      combination except 'taa', 'tga' or 'tag'
<220> FEATURE:
<221> NAME/KEY: modified_base
<222> LOCATION: (52)..(54)
<223> OTHER INFORMATION: This region discloses a, c, t or g in any
      combination except 'taa', 'tga' or 'tag'
<220> FEATURE:
<221> NAME/KEY: modified_base
<222> LOCATION: (61)..(61)
<223> OTHER INFORMATION: a, c, t or g
<220> FEATURE:
<223> OTHER INFORMATION: see specification as filed for detailed
      description of substitutions and preferred embodiments

<400> SEQUENCE: 47
ggtcgcggcc tcgagtggat tggcnnnatt nnnccgnnnn nnnnnnnnnn nnnntataac      60
naaattcaaa agccgggtga cc                                              82

<210> SEQ ID NO 48
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: a, c, t or g
<220> FEATURE:
<221> NAME/KEY: modified_base
<222> LOCATION: (29)..(31)
<223> OTHER INFORMATION: This region discloses a, c, t or g in any
      combination except 'taa', 'tga' or 'tag'
<220> FEATURE:
<221> NAME/KEY: modified_base
<222> LOCATION: (32)..(34)
<223> OTHER INFORMATION: This region discloses a, c, t or g in any
      combination except 'taa', 'tga' or 'tag'
<220> FEATURE:
<221> NAME/KEY: modified_base
<222> LOCATION: (35)..(37)
<223> OTHER INFORMATION: This region discloses a, c, t or g in any
      combination except 'taa', 'tga' or 'tag'
<220> FEATURE:
<221> NAME/KEY: modified_base
<222> LOCATION: (41)..(43)
<223> OTHER INFORMATION: This region discloses a, c, t or g in any
      combination except 'taa', 'tga' or 'tag'
<220> FEATURE:
<221> NAME/KEY: modified_base
<222> LOCATION: (47)..(49)
<223> OTHER INFORMATION: This region discloses a, c, t or g in any
      combination except 'taa', 'tga' or 'tag'
<220> FEATURE:
<221> NAME/KEY: modified_base
<222> LOCATION: (56)..(58)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 48
ggcaaaggtc tcgagtggct gggcnattnn nnnnnnnggc nnnaccnnnt ataacnnngc      60
ctttattagc cgcctgagca tc                                              82
```

```
<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(40)
<223> OTHER INFORMATION: a, c, t or g
<220> FEATURE:
<221> NAME/KEY: modified_base
<222> LOCATION: (41)..(43)
<223> OTHER INFORMATION: This region discloses a, c, t or g in any
      combination except 'taa', 'tga' or 'tag'
<220> FEATURE:
<221> NAME/KEY: modified_base
<222> LOCATION: (44)..(46)
<223> OTHER INFORMATION: This region discloses a, c, t or g in any
      combination except 'taa', 'tga' or 'tag'
<220> FEATURE:
<221> NAME/KEY: modified_base
<222> LOCATION: (47)..(49)
<223> OTHER INFORMATION: This region discloses a, c, t or g in any
      combination except 'taa', 'tga' or 'tag'
<220> FEATURE:
<221> NAME/KEY: modified_base
<222> LOCATION: (56)..(56)
<223> OTHER INFORMATION: a, c, t or g
<220> FEATURE:
<223> OTHER INFORMATION: see specification as filed for detailed
      description of substitutions and preferred embodiments

<400> SEQUENCE: 49
gaaaaacgcc tcgagtgggt ggcgnnnatt nnnnnnnnnn nnnnnnnnnt attatngata      60
gcgtgaaagg ccgctttacc                                                 80

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Val Gln Leu
1

<210> SEQ ID NO 51
<211> LENGTH: 11
```

```
<212> TYPE: PRT
<213> ORGANISM: Mus sp.

<400> SEQUENCE: 51

Trp Gly Gly Asp Gly Phe Tyr Ala Met Asp Tyr
1               5                   10

<210> SEQ ID NO 52
<211> LENGTH: 11
<212> TYPE: PRT
<213> ORGANISM: Mus sp.

<400> SEQUENCE: 52

Trp Gly Gln Gly Thr Thr Leu Thr Val Ser Ser
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Thr Phe Thr Ser Tyr Trp Met His
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ile Asp Pro Asn Ser Gly Gly Thr Lys Tyr Asn Glu Lys Phe Lys
1               5                   10                  15

Ser

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Pro Tyr Tyr Ala Phe Ala Tyr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Asp Tyr Arg Gly Ala Phe Ala Tyr
1               5

<210> SEQ ID NO 57
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Tyr Tyr Tyr Ala Phe Asp Val
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Gly Val Asp Asp Phe Asp Val
1               5

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Arg Ala Tyr Ala Gly Tyr Val Phe Asp Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Tyr Ser Tyr Tyr Glu Ala Phe Asp Tyr
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Thr Ser Arg Phe Asp Tyr
1               5

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

Lys Ala Ser Gln Ser Val Asp Tyr Asp Gly Asp Ser Tyr Met Asn
1               5                   10                  15

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Ala Ala Ser Asn Leu Glu Ser Gly Ile Pro Ala Arg Phe Ser Gly
1               5                   10                  15

Ser

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Tyr Asn Ser Tyr Pro Leu
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Tyr Trp Ser Arg Pro Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Gln Tyr Trp Ser Tyr Pro Phe
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Ser Ser His Tyr Pro Leu
1               5

<210> SEQ ID NO 68
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 68

Gln Gln Ser Asn Ala Tyr Pro Arg
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gln Lys Ile Gln Arg Pro Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Asp Tyr Glu Lys Pro Tyr
1               5

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Thr Phe Ser Ser Tyr Thr Met Ser Trp Val Arg Gln Thr Pro Glu
1               5                   10                  15

Lys Arg Leu Glu
            20

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ile Ser Gly Gly Gly Gly Asn Thr Tyr Tyr Pro Asp Ser Val Lys
1               5                   10                  15

Gly

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 73

Arg Trp Tyr Tyr Ala Phe Asp Tyr
1               5

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Tyr Tyr His Tyr Phe Ser Asp Phe Asp Tyr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Ile Tyr Tyr Ala Phe Asp Tyr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Leu Gly Gln Glu Lys Pro Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Gly Asn His Phe Pro Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Gly Thr Ser Lys Pro Tyr
1               5

<210> SEQ ID NO 79
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Asp Gly Ser Thr Tyr Ala Phe Ala Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ser Ser Tyr Thr Tyr Ala Phe Asp Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Asp Ser Tyr Thr Tyr Ala Phe Ala Tyr
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Tyr Tyr Tyr Ala Phe Asp Tyr
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Tyr Tyr Tyr Ala Phe Asp Tyr
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Tyr Lys Tyr Ala Phe Asp Tyr
```

```
1               5

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Thr Ala Tyr Gly Tyr Arg Tyr Tyr Phe Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Lys Tyr Ala Phe Asp Tyr
1               5

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Lys Ser Val Ser Thr Ser Gly Tyr Ser Tyr Met His
1               5                   10                  15

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Leu Ala Ser Asn Leu Glu Ser Gly Val Pro Ala Arg Phe Ser Gly
1               5                   10                  15

Ser

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Tyr Ser Glu Tyr Pro Phe
1               5

<210> SEQ ID NO 90
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 90

Gln Gln Tyr Ser Ser Tyr Pro Phe
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Phe Gln Tyr Tyr Glu Arg Pro His
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Gln Ile Tyr Ser Phe Pro Leu
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Tyr Tyr Ser Tyr Pro Phe
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Tyr His Lys Tyr Pro Phe
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Tyr Glu Lys Pro Tyr
1               5
```

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Tyr Asn His Val Pro Phe
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Tyr Arg Ser Tyr Met Asp Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Tyr Arg Ser Tyr Phe Asp Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Tyr Arg Ser Tyr Phe Asp Val
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln His Trp Glu Tyr Pro His
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 101

Gln Gln Tyr Trp Gln Tyr Pro Phe
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gln Tyr Trp Ser Tyr Pro Phe
1               5

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Tyr Tyr Gly Ser Lys Tyr Pro Phe Asp Tyr
1               5                   10

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Tyr Tyr Gly Ile Phe Asp Tyr
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Ile Tyr Tyr Ala Phe Asp Tyr
1               5

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ser Ser Gln Ser Ile Val His Ser Asn Gly Asn Thr Tyr Leu Glu
1               5                   10                  15

<210> SEQ ID NO 107
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 107

Tyr Lys Val Ser Asn Arg Phe Ser Gly Val Pro Asp Arg Phe Ser Gly
1               5                   10                  15
Ser

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Gln Arg Ser His Tyr Pro Leu
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Glu Glu His Val Pro Leu
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Tyr Ser Ser Tyr Pro Phe
1               5

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Met Tyr Tyr Ser Tyr Gly Met Thr Phe Asp Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112
```

```
Met Tyr Tyr Ala Ser Gly Met Ala Phe Asp Tyr
1               5                   10
```

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Tyr Arg Tyr Gly Ser Gly Tyr Tyr Phe Asp Tyr
1               5                   10
```

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Tyr Thr Tyr Ser Met Gly Tyr Tyr Phe Asp Tyr
1               5                   10
```

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Arg Tyr Tyr Asp Asn Leu Thr Phe Ala Val
1               5                   10
```

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Ser Gly Tyr Gly Tyr Tyr Phe Ala Tyr
1               5
```

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Thr Ser Ser Ser Phe Trp Tyr Ala Phe Asp Tyr
1               5                   10
```

<210> SEQ ID NO 118
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 118

Gln Gln Asp Asp His Tyr Pro Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Asp Asn Glu Tyr Pro Tyr
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Gln Gly Ser His Tyr Pro Arg
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Gly Ser His Tyr Pro Arg
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Gln Glu Glu Glu Trp Pro Asp
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Gln Arg Ser His Tyr Pro Gln
1               5

```
<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Gln Leu Tyr Ser Tyr Pro Lys
1               5

<210> SEQ ID NO 125
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Ser Tyr
            20                  25                  30

Tyr Met His
        35

<210> SEQ ID NO 126
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Trp Val Lys Gln Arg Pro Gly Gln Gly Leu Glu Trp Ile Gly Tyr Ile
1               5                   10                  15

Tyr Pro Gly Ser
            20

<210> SEQ ID NO 127
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Gly Thr Asn Tyr Asn Glu Lys Phe Lys Gly Lys Ala Thr Leu Thr
1               5                   10                  15

Val Asp Lys Ser Ser Ser Thr Ala Tyr Met Gln Leu Ser Ser Leu Thr
            20                  25                  30

Ser Glu Asp Ser Ala Val Tyr Tyr Cys Ala Arg
        35                  40

<210> SEQ ID NO 128
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 128

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Ala
        35

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Val Arg Gln Ala Pro Thr Lys Gly Leu Glu Trp Val Ala Ser Ile
1               5                   10                  15

Ser Thr Asp Gly
        20

<210> SEQ ID NO 130
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ser Ser Thr Tyr Tyr Arg Asp Ser Val Lys Gly Arg Phe Thr Ile Ser
1               5                   10                  15

Arg Asp Asn Ala Lys Ser Thr Leu Tyr Leu Gln Met Asp Ser Leu Arg
            20                  25                  30

Ser Glu Asp Thr Ala Thr Tyr Tyr Cys Ala Arg
        35                  40

<210> SEQ ID NO 131
<211> LENGTH: 11
<212> TYPE: PRT
<213> ORGANISM: Rattus sp.

<400> SEQUENCE: 131

Trp Gly Gln Gly Val Met Val Thr Val Ser Ser
1               5                   10

<210> SEQ ID NO 132
<211> LENGTH: 6
<212> TYPE: PRT
<213> ORGANISM: Rattus sp.

<400> SEQUENCE: 132

Glu Thr Thr Ala Pro Ser
1               5

<210> SEQ ID NO 133
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<223> OTHER INFORMATION: see specification as filed for detailed
      description of substitutions and preferred embodiments

<400> SEQUENCE: 133
accaaaggtc tcgagtgggt ggcgaccatt asctatgatg gcagcavcac ctattatcgt    60
gatagc                                                              66

<210> SEQ ID NO 134
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: This region discloses a, c, t or g in any
      combination except 'taa', 'tga' or 'tag'
<220> FEATURE:
<221> NAME/KEY: modified_base
<222> LOCATION: (31)..(33)
<223> OTHER INFORMATION: This region discloses a, c, t or g in any
      combination except 'taa', 'tga' or 'tag'
<220> FEATURE:
<221> NAME/KEY: modified_base
<222> LOCATION: (34)..(36)
<223> OTHER INFORMATION: This region discloses a, c, t or g in any
      combination except 'taa', 'tga' or 'tag'
<220> FEATURE:
<221> NAME/KEY: modified_base
<222> LOCATION: (37)..(39)
<223> OTHER INFORMATION: This region discloses a, c, t or g in any
      combination except 'taa', 'tga' or 'tag'
<220> FEATURE:
<221> NAME/KEY: modified_base
<222> LOCATION: (40)..(42)
<223> OTHER INFORMATION: This region discloses a, c, t or g in any
      combination except 'taa', 'tga' or 'tag'
<220> FEATURE:
<221> NAME/KEY: modified_base
<222> LOCATION: (46)..(48)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 134
gaagacgtgg cgacctattt ttgcnnncag nnnnnnnnnn nnccgnnnac ctttggtgcg    60
ggcacca                                                             67

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ctgcaaccgg aagacgtggc gacctatttt tgc                                33

<210> SEQ ID NO 136
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 136
cggccacgta cgtttgattt ccagtttggt gccaccgcca aagg    44

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cggccacgta cgtttgattt c    21

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Phe Thr Phe Ser Asn Tyr Gly Met Ala Trp Val Arg Gln Ala Pro Thr
1               5                   10                  15

Lys Gly Leu Glu
            20

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Thr Ile Ser Tyr Asp Gly Ser Ser Thr Tyr Tyr Arg Asp Ser Val Lys
1               5                   10                  15

Gly

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Ser Trp Gly Tyr Tyr Arg Arg Lys Phe Asp Tyr
1               5                   10

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Tyr Tyr Thr Gly Ser Phe Asp
1               5

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Asp Tyr Gly Gly Trp Arg Tyr Lys Phe Asp Tyr
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Asp Trp Gly Gly Met Arg Tyr Lys Met Asp Tyr
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Gly Trp Tyr Lys Gly Arg Tyr Lys Phe Asp Tyr
1               5                   10

<210> SEQ ID NO 145
<211> LENGTH: 25
<212> TYPE: PRT
<213> ORGANISM: Mus sp.

<400> SEQUENCE: 145

Lys Ala Thr Leu Thr Val Asp Lys Pro Ser Ser Thr Ala Tyr Met Gln
1               5                   10                  15

Leu Ser Ser Leu Thr Ser Glu Asp Ser
            20                  25

<210> SEQ ID NO 146
<211> LENGTH: 25
<212> TYPE: PRT
<213> ORGANISM: Mus sp.

<400> SEQUENCE: 146

Arg Val Thr Leu Thr Val Asp Lys Pro Ser Ser Thr Ala Tyr Met Gln
1               5                   10                  15

Leu Ser Ser Leu Thr Ser Glu Asp Ser
            20                  25

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Tyr Trp Tyr Phe Asp Val Trp Gly Ala Gly Thr Thr Val Thr Val Ser
1               5                   10                  15

Ser

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Tyr Phe Asp Tyr Trp Gly Gln Gly Thr Thr Leu Thr Val Ser Ser
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Trp Phe Ala Tyr Trp Gly Gln Gly Thr Leu Val Thr Val Ser Ala
1               5                   10                  15

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Tyr Tyr Ala Met Asp Tyr Trp Gly Gln Gly Thr Ser Val Thr Val Ser
1               5                   10                  15

Ser

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Trp Thr Phe Gly Gly Gly Thr Lys Leu Glu Ile Lys Arg Ala
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Thr Phe Gly Gly Gly Thr Lys Leu Glu Ile Lys Arg Ala
1               5                   10
```

```
<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Thr Phe Ser Asp Gly Thr Arg Leu Glu Ile Lys Pro Ala
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Phe Thr Phe Gly Ser Gly Thr Lys Leu Glu Ile Lys Arg Ala
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Thr Phe Gly Ala Gly Thr Lys Leu Glu Leu Lys Arg Ala
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, Tyr, Ile, Phe or Leu

<400> SEQUENCE: 156

Xaa Thr Phe Gly Gly Gly Thr Lys Leu Glu Ile Lys Arg Thr
1               5                   10

<210> SEQ ID NO 157
<211> LENGTH: 10
<212> TYPE: PRT
<213> ORGANISM: Mus sp.
<220> FEATURE:
<221> NAME/KEY: MOD_RES
<222> LOCATION: (3)..(3)
<223> OTHER INFORMATION: Asp, Asn or Tyr
<220> FEATURE:
<221> NAME/KEY: MOD_RES
<222> LOCATION: (6)..(6)
<223> OTHER INFORMATION: Ser or Asn
<220> FEATURE:
<223> OTHER INFORMATION: see specification as filed for detailed
      description of substitutions and preferred embodiments

<400> SEQUENCE: 157

Arg Ile Xaa Pro Asn Xaa Gly Gly Thr Lys
```

```
                1               5                         10

<210> SEQ ID NO 158
<211> LENGTH: 9
<212> TYPE: PRT
<213> ORGANISM: Mus sp.
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (7)..(7)
<223> OTHER INFORMATION: Ser or Gly
<220> FEATURE:
<223> OTHER INFORMATION: see specification as filed for detailed
      description of substitutions and preferred embodiments

<400> SEQUENCE: 158

Val Ile Trp Xaa Xaa Gly Xaa Thr Asp
1               5

<210> SEQ ID NO 159
<211> LENGTH: 10
<212> TYPE: PRT
<213> ORGANISM: Mus sp.
<220> FEATURE:
<221> NAME/KEY: MOD_RES
<222> LOCATION: (3)..(3)
<223> OTHER INFORMATION: Ser or Asn
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (8)..(8)
<223> OTHER INFORMATION: Asn or Ser
<220> FEATURE:
<223> OTHER INFORMATION: see specification as filed for detailed
      description of substitutions and preferred embodiments

<400> SEQUENCE: 159

Thr Ile Xaa Gly Gly Xaa Gly Xaa Thr Tyr
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Asp, Asn, Tyr or His
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Gly, Ser or Asp
<220> FEATURE:
```

```
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)..(13)
<223> OTHER INFORMATION: Glu or Gln
<220> FEATURE:
<223> OTHER INFORMATION: see specification as filed for detailed
      description of substitutions and preferred embodiments

<400> SEQUENCE: 160

Xaa Ile Xaa Pro Xaa Xaa Xaa Xaa Xaa Xaa Tyr Asn Xaa Lys Phe Lys
1               5                   10                  15

Ser

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Met
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Ser or Ala
<220> FEATURE:
<223> OTHER INFORMATION: see specification as filed for detailed
      description of substitutions and preferred embodiments

<400> SEQUENCE: 161

Xaa Ile Xaa Xaa Xaa Gly Xaa Thr Xaa Tyr Asn Xaa Ala Phe Ile Ser
1               5                   10                  15

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(9)
<223> OTHER INFORMATION: Any amino acid
```

```
<220> FEATURE:
<221> NAME/KEY: MOD_RES
<222> LOCATION: (12)..(12)
<223> OTHER INFORMATION: Pro or Ala
<220> FEATURE:
<223> OTHER INFORMATION: see specification as filed for detailed
      description of substitutions and preferred embodiments

<400> SEQUENCE: 162

Xaa Ile Xaa Xaa Xaa Xaa Xaa Xaa Xaa Tyr Tyr Xaa Asp Ser Val Lys
1               5                   10                  15

Gly

<210> SEQ ID NO 163
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (96)..(99)
<223> OTHER INFORMATION: Any amino acid
<220> FEATURE:
<221> NAME/KEY: MOD_RES
<222> LOCATION: (101)..(101)
<223> OTHER INFORMATION: Any amino acid
<220> FEATURE:
<223> OTHER INFORMATION: see specification as filed for detailed
      description of substitutions and preferred embodiments

<400> SEQUENCE: 163

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Xaa Gln Xaa
                85                  90                  95

Xaa Xaa Xaa Pro Xaa Thr Phe Gly Gly Gly Thr Lys Leu Glu Ile Lys
            100                 105                 110

Arg Thr

<210> SEQ ID NO 164
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(98)
```

<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<223> OTHER INFORMATION: see specification as filed for detailed
      description of substitutions and preferred embodiments

<400> SEQUENCE: 164

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Xaa Gln Xaa Xaa
                85                  90                  95

Xaa Xaa Pro Xaa Thr Phe Gly Gly Gly Thr Lys Leu Glu Ile Lys Arg
            100                 105                 110

Thr

<210> SEQ ID NO 165
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (97)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<223> OTHER INFORMATION: see specification as filed for detailed
      description of substitutions and preferred embodiments

<400> SEQUENCE: 165

Asp Ile Val Met Thr Gln Ser Pro Thr Phe Leu Ala Val Thr Ala Ser
1               5                   10                  15

Lys Lys Val Thr Ile Ser Cys Thr Ala Ser Glu Ser Leu Tyr Ser Ser
            20                  25                  30

Lys His Lys Val His Tyr Leu Ala Trp Tyr Gln Lys Lys Pro Glu Gln
        35                  40                  45

Ser Pro Lys Leu Leu Ile Tyr Gly Ala Ser Asn Arg Tyr Ile Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Val Glu Asp Leu Thr His Tyr Tyr Cys Xaa Gln
                85                  90                  95

Xaa Xaa Xaa Xaa Pro Xaa Thr Phe Gly Gly Gly Thr Lys Leu Glu Ile

Lys Arg Thr
         115

<210> SEQ ID NO 166
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(98)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<223> OTHER INFORMATION: see specification as filed for detailed
      description of substitutions and preferred embodiments

<400> SEQUENCE: 166

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Xaa Gln Xaa Xaa
                85                  90                  95

Xaa Xaa Pro Xaa Thr Phe Gly Gly Gly Thr Lys Leu Glu Ile Lys Arg
            100                 105                 110

Thr

<210> SEQ ID NO 167
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (97)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<223> OTHER INFORMATION: see specification as filed for detailed
      description of substitutions and preferred embodiments

<400> SEQUENCE: 167

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Xaa Gln
                85                  90                  95

Xaa Xaa Xaa Xaa Pro Xaa Thr Phe Gly Gly Gly Thr Lys Leu Glu Ile
            100                 105                 110

Lys Arg Thr
        115

<210> SEQ ID NO 168
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (91)..(94)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<223> OTHER INFORMATION: see specification as filed for detailed
      description of substitutions and preferred embodiments

<400> SEQUENCE: 168

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Xaa Gln Xaa Xaa Xaa Xaa Pro Xaa
                85                  90                  95

Thr Phe Gly Gly Gly Thr Lys Leu Glu Ile Lys Arg Thr
            100                 105

<210> SEQ ID NO 169
<211> LENGTH: 115
<212> TYPE: PRT
<213> ORGANISM: Artificial Sequence
<220> FEATURE:
<223> OTHER INFORMATION: Description of Artificial Sequence: Synthetic

```
                          consensus
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (97)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<223> OTHER INFORMATION: see specification as filed for detailed
      description of substitutions and preferred embodiments

<400> SEQUENCE: 169

Asp Ile Val Met Thr Gln Ser Pro Ser Ser Leu Ala Val Ser Ala Gly
1               5                   10                  15

Glu Lys Val Ser Ile Ser Cys Arg Ser Ser Gln Ser Leu Val His Ser
            20                  25                  30

Asp Gly Lys Lys Thr Tyr Leu Asn Trp Tyr Leu Gln Lys Pro Gly Gln
        35                  40                  45

Ser Pro Gln Leu Leu Ile Tyr Trp Val Ser Asn Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Xaa Gln
                85                  90                  95

Xaa Xaa Xaa Xaa Pro Xaa Thr Phe Gly Gly Gly Thr Lys Leu Glu Ile
            100                 105                 110

Lys Arg Thr
        115

<210> SEQ ID NO 170
<211> LENGTH: 109
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (91)..(94)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<223> OTHER INFORMATION: see specification as filed for detailed
      description of substitutions and preferred embodiments

<400> SEQUENCE: 170

Asp Ile Gln Met Thr Gln Ser Pro Ser Ser Leu Ser Ala Ser Leu Gly
1               5                   10                  15

Asp Arg Val Thr Ile Glu Cys Lys Ala Ser Gln Asn Ile Tyr Lys Tyr
            20                  25                  30

Leu Ala Trp Tyr Gln Gln Lys Pro Gly Lys Ala Pro Lys Leu Leu Ile
        35                  40                  45

Tyr Asn Ala Asn Ser Leu Gln Thr Gly Val Pro Ser Arg Phe Ser Gly
```

```
            50                  55                  60
Ser Gly Ser Gly Thr Asp Tyr Thr Leu Thr Ile Ser Ser Leu Gln Pro
 65                  70                  75                  80

Glu Asp Val Ala Thr Tyr Phe Cys Xaa Gln Xaa Xaa Xaa Xaa Pro Xaa
                 85                  90                  95

Thr Phe Gly Ala Gly Thr Lys Leu Glu Leu Lys Arg Thr
            100                 105
```

<210> SEQ ID NO 171
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (280)..(282)
<223> OTHER INFORMATION: This region discloses a, c, t or g in any
      combination except 'taa', 'tga' or 'tag'
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combinationexcept 'taa', 'tga' and 'tag'
<220> FEATURE:
<223> OTHER INFORMATION: see specification as filed for detailed
      description of substitutions and preferred embodiments

<400> SEQUENCE: 171

```
gatatcctga tgacccagac cccactgagc ctgccagtta gcctgggcga tcaggccagc     60
attagctgcc gcagcagcca gagcattgtg catagcaacg gcaacaccta cctggaatgg    120
tacctgcaaa aaccgggcca gagcccgaaa ctgctgatct ataaagttag caaccgcttt    180
agcggcgtgc cggatcgctt cagcggcagc ggatccggca ccgatttcac cctgaaaatc    240
agccgcgtgg aagccgaaga cctgggcgtg tattattgcn nnnnnnnnn nnnnnnnnn     300 nnnaccttg gcggtggcac caaactggaa atcaaacgta cg                        342
```

<210> SEQ ID NO 172

```
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (277)..(279)
<223> OTHER INFORMATION: This region discloses a, c, t or g in any
      combination except 'taa', 'tga' or 'tag'
<220> FEATURE:
<221> NAME/KEY: modified_base
<222> LOCATION: (280)..(282)
<223> OTHER INFORMATION: This region discloses a, c, t or g in any
      combination except 'taa', 'tga' or 'tag'
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 172
gatatcgtgc tgacccagag cccagcaagc ctggccgtga gcctgggcca acgcgccacc      60
attagctgcc gcgccagcaa aagcgttagc accagcggct atagctatat gcactggtac     120
cagcagaaac cgggccagcc gccgaaactg ctgatctatc tggcgagcaa cctggaaagc     180
ggcgtgccag cccgctttag cggcagcgga tccggcaccg atttcaccct gaacatccac     240
ccggtggaag aagaagacgc cgccacctat tattgcnnnn nnnnnnnnnn nnnnnnnnnn     300
acctttggcg gtggcaccaa actggaaatc aaacgtacg                            339

<210> SEQ ID NO 173
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
```

<222> LOCATION: (286)..(288)
<223> OTHER INFORMATION: This region discloses a, c, t or g in any
      combination except 'taa', 'tga' or 'tag'
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag'
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 173

```
gatatcgtga tgacccagag cccgaccttt ctggccgtga ccgccagcaa aaaagtgacc      60
attagctgca ccgccagcga aagcctgtat agcagcaaac ataaagtgca ctatctggcc    120
tggtaccaga aaaaaccgga acagagcccg aaactgctga tctatggcgc cagcaaccgc    180
tatattggcg tgccggatcg ctttaccggc agcggatccg gcaccgattt caccctgacc    240
atcagcagcg tgcaggtgga agacctgacc cattattact gcnnnnnnnn nnnnnnnnnn    300
nnnnnnacct ttggcggtgg caccaaactg gaaatcaaac gtacg                    345
```

<210> SEQ ID NO 174
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (277)..(279)
<223> OTHER INFORMATION: This region discloses a, c, t or g in any
      combination except 'taa', 'tga' or 'tag'
<220> FEATURE:
<221> NAME/KEY: modified_base
<222> LOCATION: (280)..(282)
<223> OTHER INFORMATION: This region discloses a, c, t or g in any
      combination except 'taa', 'tga' or 'tag'
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'

```
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 174
gatatcgtgc tgacccagag cccagcgagc ctggccgtga gcctgggcca acgcgccacc    60
attagctgca aagccagcca gagcgtggat tatgatggcg atagctatat gaactggtac   120
cagcagaaac cgggccagcc gccgaaactg ctgatctatg ccgccagcaa cctggaaagc   180
ggcattccag cccgctttag cggcagcgga tccggcaccg atttcaccct gaacatccac   240
ccggtggaag aagaagacgc cgccacctat tattgcnnnn nnnnnnnnnn nnnnnnnnn    300 acctttggcg gtggcaccaa actggaaatc aaacgtacg                          339

<210> SEQ ID NO 175
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
```

<223> OTHER INFORMATION: This region discloses a, c, t or g in any
      combination except 'taa', 'tga' or 'tag'
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 175
gatatcgtga tgacccagag cccgagcagc ctgagcgtta gcgcaggcga aaaagtgacc      60
atgagctgca aaagcagcca gagcctgctg aacagcggca accagaaaaa ctatctggcc     120
tggtaccagc agaaaccggg ccagccgccg aaactgctga tctatggcgc cagcacccgc     180
gaaagcggcg tgccggatcg ctttaccggc agcggatccg gcaccgattt caccctgacc     240
attagcagcg tgcaggccga agacctggcc gtgtattact gcnnnnnnnn nnnnnnnnnn     300
nnnnnnacct tggcggtgg caccaaactg gaaatcaaac gtacg                      345

<210> SEQ ID NO 176
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (265)..(267)
<223> OTHER INFORMATION: This region discloses a, c, t or g in any
      combination except 'taa', 'tga' or 'tag'
<220> FEATURE:
<221> NAME/KEY: modified_base
<222> LOCATION: (268)..(270)
<223> OTHER INFORMATION: This region discloses a, c, t or g in any
      combination except 'taa', 'tga' or 'tag'
<220> FEATURE:
<221> NAME/KEY: modified_base
<222> LOCATION: (271)..(273)
<223> OTHER INFORMATION: This region discloses a, c, t or g in any
      combination except 'taa', 'tga' or 'tag'
<220> FEATURE:
<221> NAME/KEY: modified_base
<222> LOCATION: (274)..(276)
<223> OTHER INFORMATION: This region discloses a, c, t or g in any
      combination except 'taa', 'tga' or 'tag'
<220> FEATURE:
<221> NAME/KEY: modified_base
<222> LOCATION: (277)..(279)
<223> OTHER INFORMATION: This region discloses a, c, t or g in any
      combination except 'taa', 'tga' or 'tag'
<220> FEATURE:
<221> NAME/KEY: modified_base
<222> LOCATION: (280)..(282)
<223> OTHER INFORMATION: This region discloses a, c, t or g in any
      combination except 'taa', 'tga' or 'tag'
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 176

```
gatatccaga tgacccagag cccgagcagc ctgagcgcca gcctgggcgg caaagtgacc        60
attacctgca aagccagcca ggatattaac aaatatatcg cctggtacca gcataaaccg       120
ggcaaaggcc cacgcctgct gattcattat accagcaccc tgcaaccggg cattccgagc       180
cgctttagcg gcagcggatc cggtcgcgat tatagcttca gcattagcaa cctggaaccg       240
gaagacatcg ccacctatta ttgcnnnnnn nnnnnnnnnn nnnnnnnnac ctttggcggt       300
ggcaccaaac tggaaatcaa acgtacg                                           327
```

<210> SEQ ID NO 177
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<221> NAME/KEY: modified_base
<222> LOCATION: (289)..(291)
<223> OTHER INFORMATION: This region discloses a, c, t or g in any
      combination except 'taa', 'tga' or 'tag'
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag'
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 177

```
gatatcgtga tgacccagtc tccgagcagc ctggccgtta gcgcgggtga aaaagtgagc        60
attagctgca gaagcagcca gagcctggtt catagcgatg gcaaaaaaac ctatctgaac       120
tggtacctgc aaaaaccggg ccagagcccg cagctgctga tttattgggt gagcaaccgt       180
gaaagcggcg tgccggatcg ttttagcggc agcggatccg gcaccgattt taccctgaaa       240
attagccgtg tggaagcgga agacctgggc gtgtattatt gcnnnnnnnn nnnnnnnnn        300 nnnnnnacct ttggcggtgg caccaaactg gaaatcaaac gtacg                       345
```

```
<210> SEQ ID NO 178
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (265)..(267)
<223> OTHER INFORMATION: This region discloses a, c, t or g in any
      combination except 'taa', 'tga' or 'tag'
<220> FEATURE:
<221> NAME/KEY: modified_base
<222> LOCATION: (268)..(270)
<223> OTHER INFORMATION: This region discloses a, c, t or g in any
      combination except 'taa', 'tga' or 'tag'
<220> FEATURE:
<221> NAME/KEY: modified_base
<222> LOCATION: (271)..(273)
<223> OTHER INFORMATION: This region discloses a, c, t or g in any
      combination except 'taa', 'tga' or 'tag'
<220> FEATURE:
<221> NAME/KEY: modified_base
<222> LOCATION: (274)..(276)
<223> OTHER INFORMATION: This region discloses a, c, t or g in any
      combination except 'taa', 'tga' or 'tag'
<220> FEATURE:
<221> NAME/KEY: modified_base
<222> LOCATION: (277)..(279)
<223> OTHER INFORMATION: This region discloses a, c, t or g in any
      combination except 'taa', 'tga' or 'tag'
<220> FEATURE:
<221> NAME/KEY: modified_base
<222> LOCATION: (280)..(282)
<223> OTHER INFORMATION: This region discloses a, c, t or g in any
      combination except 'taa', 'tga' or 'tag'
<220> FEATURE:
<221> NAME/KEY: modified_base
<222> LOCATION: (283)..(285)
<223> OTHER INFORMATION: This region discloses a, c, t or g in any
      combination except 'taa', 'tga' or 'tag'
<220> FEATURE:
<221> NAME/KEY: modified_base
<222> LOCATION: (286)..(288)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 178
gatatccaga tgacccagag cccgagcagc ctgagcgcga gcctgggtga tcgtgtgacc     60
attgaatgca aagcgagcca gaacatctat aaatatctgg cctggtacca gcagaaaccg    120
ggcaaagcgc cgaaactgct gatttataac gcgaacagcc tgcaaaccgg tgtgccgagc    180
cgttttagcg gcagcggatc cggcaccgat tatacc ctga cgattagctc tctgcaaccg    240
gaagacgtgg cgacctattt ttgcnnnnnn nnnnnnnnnn nnnnnnnnac ctttggtgcg    300
ggcaccaaac tggaactgaa acgtacg                                        327

<210> SEQ ID NO 179
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Asp, Asn or Tyr
<220> FEATURE:
<221> NAME/KEY: MOD_RES
```

```
<222> LOCATION: (55)..(55)
<223> OTHER INFORMATION: Ser or Asn
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 179

Glu Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Xaa Pro Asn Xaa Gly Gly Thr Lys Tyr Asn Glu Lys Phe
    50                  55                  60

Lys Ser Lys Ala Thr Leu Thr Val Asp Lys Pro Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Xaa Xaa Xaa Xaa Xaa Xaa Xaa Xaa Xaa Xaa Xaa Trp Gly
            100                 105                 110

Gln Gly Thr Thr Leu Thr Val Ser Ser
        115                 120

<210> SEQ ID NO 180
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Asp, Asn or Tyr
<220> FEATURE:
<221> NAME/KEY: MOD_RES
<222> LOCATION: (55)..(55)
<223> OTHER INFORMATION: Ser or Asn
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
```

```
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 180
```

| | | | | | | | | | | | | | | |
|---|---|---|---|---|---|---|---|---|---|---|---|---|---|---|
| Glu | Val | Gln | Leu | Gln | Gln | Pro | Gly | Ala | Glu | Leu | Val | Lys | Pro | Gly | Ala |
| 1 | | | | 5 | | | | | 10 | | | | | 15 | |
| Ser | Val | Lys | Leu | Ser | Cys | Lys | Ala | Ser | Gly | Tyr | Thr | Phe | Thr | Ser | Tyr |
| | | | 20 | | | | | 25 | | | | | 30 | | |
| Trp | Met | His | Trp | Val | Lys | Gln | Arg | Pro | Gly | Arg | Gly | Leu | Glu | Trp | Ile |
| | | 35 | | | | | 40 | | | | | 45 | | | |
| Gly | Arg | Ile | Xaa | Pro | Asn | Xaa | Gly | Gly | Thr | Lys | Tyr | Asn | Glu | Lys | Phe |
| 50 | | | | | 55 | | | | | 60 | | | | | |
| Lys | Ser | Arg | Val | Thr | Leu | Thr | Val | Asp | Lys | Pro | Ser | Ser | Thr | Ala | Tyr |
| 65 | | | | | 70 | | | | | 75 | | | | | 80 |
| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |
| Ala | Arg | Xaa | Xaa | Xaa | Xaa | Xaa | Xaa | Xaa | Xaa | Xaa | Xaa | Xaa | Trp | Gly | |
| | | | 100 | | | | | 105 | | | | | 110 | | |
| Gln | Gly | Thr | Thr | Leu | Thr | Val | Ser | Ser | | | | | | | |
| | | 115 | | | | | 120 | | | | | | | | |

```
<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (53)..(53)
<223> OTHER INFORMATION: Ser or Gly
<220> FEATURE:
<221> NAME/KEY: MOD_RES
<222> LOCATION: (54)..(54)
<223> OTHER INFORMATION: Gly or Asp
<220> FEATURE:
<221> NAME/KEY: MOD_RES
<222> LOCATION: (56)..(56)
<223> OTHER INFORMATION: Ser or Gly
<220> FEATURE:
<221> NAME/KEY: MOD_RES
<222> LOCATION: (98)..(99)
<223> OTHER INFORMATION: Any amino acid
<220> FEATURE:
<221> NAME/KEY: MOD_RES
<222> LOCATION: (100)..(104)
<223> OTHER INFORMATION: Any amino acid or not present
<220> FEATURE:
<221> NAME/KEY: MOD_RES
<222> LOCATION: (105)..(107)
<223> OTHER INFORMATION: Any amino acid
<220> FEATURE:
<221> NAME/KEY: MOD_RES
<222> LOCATION: (108)..(108)
<223> OTHER INFORMATION: Asp or Ala
<220> FEATURE:
<221> NAME/KEY: MOD_RES
<222> LOCATION: (109)..(109)
<223> OTHER INFORMATION: Tyr or Val
```

-continued

```
<220> FEATURE:
<223> OTHER INFORMATION: see specification as filed for detailed
      description of substitutions and preferred embodiments

<400> SEQUENCE: 181

Glu Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Xaa Xaa Gly Xaa Thr Asp Tyr Asn Ala Ala Phe Ile
    50                  55                  60

Ser Arg Leu Ser Ile Ser Lys Asp Asn Ser Lys Ser Gln Val Phe Phe
65              70                  75                  80

Lys Met Asn Ser Leu Gln Ala Asp Asp Thr Ala Ile Tyr Tyr Cys Ala
                85                  90                  95

Arg Xaa Xaa Xaa Xaa Xaa Xaa Xaa Xaa Xaa Xaa Xaa Trp Gly Gln
            100                 105                 110

Gly Thr Thr Leu Thr Val Ser Ser
        115                 120

<210> SEQ ID NO 182
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (53)..(53)
<223> OTHER INFORMATION: Ser or Asn
<220> FEATURE:
<221> NAME/KEY: MOD_RES
<222> LOCATION: (57)..(57)
<223> OTHER INFORMATION: Ser, Thr or Asn
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 182

Glu Val Gln Leu Gln Glu Ser Gly Pro Gly Leu Val Lys Pro Ser Gln
1               5                   10                  15

Ser Leu Ser Leu Thr Cys Ser Val Ser Gly Tyr Ser Ile Thr Ser Gly
            20                  25                  30

Tyr Tyr Trp Asn Trp Ile Arg Gln Phe Pro Gly Asn Lys Leu Glu Trp
```

```
            35                  40                  45
Met Gly Tyr Ile Xaa Tyr Asp Gly Xaa Asn Asn Tyr Asn Pro Ser Leu
        50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                85                  90                  95

Ala Arg Xaa Xaa Xaa Xaa Xaa Xaa Xaa Xaa Xaa Xaa Xaa Xaa Trp Gly
            100                 105                 110

Gln Gly Thr Thr Leu Thr Val Ser Ser
        115                 120

<210> SEQ ID NO 183
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Ser or Asn
<220> FEATURE:
<221> NAME/KEY: MOD_RES
<222> LOCATION: (55)..(55)
<223> OTHER INFORMATION: Gly or Ser
<220> FEATURE:
<221> NAME/KEY: MOD_RES
<222> LOCATION: (57)..(57)
<223> OTHER INFORMATION: Asn or Ser
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 183

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Xaa Gly Gly Xaa Gly Xaa Thr Tyr Tyr Pro Asp Ser Val
    50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
```

```
                    85                  90                  95

Ala Arg Xaa Xaa Xaa Xaa Xaa Xaa Xaa Xaa Xaa Xaa Trp Gly
            100                 105                 110

Gln Gly Thr Thr Leu Thr Val Ser Ser
            115                 120

<210> SEQ ID NO 184
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Asn or Tyr
<220> FEATURE:
<221> NAME/KEY: MOD_RES
<222> LOCATION: (55)..(55)
<223> OTHER INFORMATION: Ser or Thr
<220> FEATURE:
<221> NAME/KEY: MOD_RES
<222> LOCATION: (57)..(57)
<223> OTHER INFORMATION: Val or Glu
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 184

Glu Val Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Glu Trp Met
        35                  40                  45

Gly Trp Ile Xaa Thr Tyr Xaa Gly Xaa Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Xaa Xaa Xaa Xaa Xaa Xaa Xaa Xaa Xaa Xaa Trp Gly
            100                 105                 110

Gln Gly Thr Thr Leu Thr Val Ser Ser
            115                 120
```

```
<210> SEQ ID NO 185
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Gly or Asn
<220> FEATURE:
<221> NAME/KEY: MOD_RES
<222> LOCATION: (57)..(57)
<223> OTHER INFORMATION: Asp or Gly
<220> FEATURE:
<221> NAME/KEY: MOD_RES
<222> LOCATION: (59)..(59)
<223> OTHER INFORMATION: Asn or Lys
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 185

Glu Val Gln Leu Gln Gln Ser Gly Ala Glu Leu Val Lys Pro Gly Ser
1               5                   10                  15

Ser Val Lys Met Ser Cys Lys Ala Ser Gly Tyr Thr Phe Thr Ser Tyr
            20                  25                  30

Tyr Ile Tyr Trp Ile Lys Gln Arg Pro Gly Gln Gly Leu Glu Trp Ile
        35                  40                  45

Gly Arg Ile Xaa Pro Gly Ser Gly Xaa Thr Xaa Tyr Asn Glu Lys Phe
    50                  55                  60

Lys Gly Lys Ala Thr Phe Thr Val Asp Lys Ser Ser Ser Thr Ala Tyr
65                  70                  75                  80

Met Gln Leu Ser Ser Leu Thr Pro Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Trp Gly
            100                 105                 110

Gln Gly Val Met Val Thr Val Ser Ser
        115                 120

<210> SEQ ID NO 186
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (52)..(52)
<223> OTHER INFORMATION: Ser or Thr
<220> FEATURE:
<221> NAME/KEY: MOD_RES
<222> LOCATION: (57)..(57)
<223> OTHER INFORMATION: Ser, Asn or Thr
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(105)
<223> OTHER INFORMATION: Any amino acid or not present
<220> FEATURE:
<221> NAME/KEY: MOD_RES
<222> LOCATION: (106)..(108)
<223> OTHER INFORMATION: Any amino acid
<220> FEATURE:
<221> NAME/KEY: MOD_RES
<222> LOCATION: (109)..(109)
<223> OTHER INFORMATION: Asp or Ala
<220> FEATURE:
<221> NAME/KEY: MOD_RES
<222> LOCATION: (110)..(110)
<223> OTHER INFORMATION: Tyr or Val
<220> FEATURE:
<223> OTHER INFORMATION: see specification as filed for detailed
      description of substitutions and preferred embodiments

<400> SEQUENCE: 186

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Ala Trp Val Arg Gln Ala Pro Thr Lys Gly Leu Glu Trp Val
        35                  40                  45

Ala Thr Ile Xaa Tyr Asp Gly Ser Xaa Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Xaa Xaa Xaa Xaa Xaa Xaa Xaa Xaa Xaa Xaa Xaa Trp Gly
            100                 105                 110

Gln Gly Val Met Val Thr Val Ser Ser
        115                 120

<210> SEQ ID NO 187
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
```

<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 187
gaagtgcaat tgcagcagcc aggcgccgaa ctggttaaac caggcgccag cgtgaaactg    60
agctgcaaag cctccggata tacctttacc agctattgga tgcattgggt gaaacagcgc   120
ccaggtcgcg gcctcgagtg gattggccgc attdatccga acarcggcgg caccaaatat   180
aacgaaaaat tcaaaagcaa agccaccctg accgtggata aaccgagcag caccgcctat   240
atgcaactga gtagcctgac cagcgaagat agcgccgtgt attattgcgc gcggnnnnnn   300
nnnnnnnnnn nnnnnnnnnn nnnnnnnnnn tggggccaag gcaccaccct gaccgttagc   360
tcaagc                                                              366

<210> SEQ ID NO 188
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:

<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 188
gaagtgcaat tgcagcagcc aggcgccgaa ctggttaaac caggcgccag cgtgaaactg      60
agctgcaaag cctccggata tacctttacc agctattgga tgcattgggt gaaacagcgc    120
ccaggtcgcg gcctcgagtg gattggccgc attdatccga acarcggcgg caccaaatat    180
aacgaaaaat tcaaaagccg ggtgaccctg accgtggata aaccgagcag caccgcctat    240
atgcaactga gtagcctgac cagcgaagat agcgccgtgt attattgcgc gcggnnnnnn    300
nnnnnnnnnn nnnnnnnnnn nnnnnnnnnn tggggccaag gcaccaccct gaccgttagc    360
tcaagc    366

<210> SEQ ID NO 189
<211> LENGTH: 363
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: modified_base
<222> LOCATION: (292)..(294)
<223> OTHER INFORMATION: This region discloses a, c, t or g in any
      combination except 'taa', 'tga' or 'tag'
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag'
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 189
gaagtgcaat tgaaacagag cggccctggc ctggtgcagc cgagccagag cctgagcatt      60
acctgcaccg tgtccggatt cagcctgacc agctatggcg tgcattgggt tcgccagagc     120
ccgggcaaag gtctcgagtg gctgggcgtg atttggrgcg rcggcrgcac cgattataac     180 gccgcctttta ttagccgcct gagcatcagc aaagataaca gcaaaagcca ggtgttcttc     240
aaaatgaaca gcctgcaagc cgatgatacc gccatctatt attgcgcgcg gnnnnnnnnn     300
```
nnnnnnnnnn nnnnnnnnnn nnnnnnntgg ggccaaggca ccaccctgac cgttagctca    360
agc                                                                  363

<210> SEQ ID NO 190
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combinationexcept 'taa', 'tga' and 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 190
gaagtgcaat tgcaggaaag cggccctggc ctggttaaac cgagccagag cctgagcctg    60

```
acctgtagcg tgtccggata tagcattacc agcggctact actggaactg gattcgccag    120
tttccgggca acaaactcga gtggatgggc tacattarct acgatggcav caacaactat    180
aacccgagcc tgaaaaaccg cattagcatc acccgcgata ccagcaaaaa ccagtttttt    240
ctgaaactga acagcgtgac caccgaagat accgccacct attattgcgc gcggnnnnnn    300
nnnnnnnnnn nnnnnnnnnn nnnnnnnnnn tggggccaag gcaccaccct gaccgttagc    360
tcaagc                                                               366
```

<210> SEQ ID NO 191
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)

<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 191

```
gaagtgcaat tggtggaaag cggcggtggt ctggttaaac caggcggcag cctgaaactg      60
agctgcgccg cctccggatt caccttagc agctatacca tgagctgggt tcgccagacc      120
ccggaaaaac gcctcgagtg ggtggcgacc attarcggtg gcrgtggcar cacctattat     180
ccagatagcg tgaaaggccg ctttaccatt agccgcgata acgccaaaaa caccctgtat     240
ctgcaaatga gcagcctgcg cagcgaagat accgccatgt attattcgcg gcggnnnnnn     300
nnnnnnnnnn nnnnnnnnnn nnnnnnnnnn tggggccaag gcaccaccct gaccgttagc     360
tcaagc                                                                 366
```

<210> SEQ ID NO 192
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any

```
combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 192
gaagtgcaat tggtgcagag cggcccagaa ctgaaaaaac cgggcgaaac cgtgaaaatt     60
agctgcaaag cctccggata tacctttacc acctatggca tgagctgggt gaaacaggcc   120
ccaggcaaag gtctcgagtg gatgggctgg attwacacct atascggcgw gccgacctat   180
gccgatgatt tcaaaggccg ctttgccttt agcctggaaa ccagcgccag caccgcctat   240
ctgcaaatta acaacctgaa aaacgaagat accgccacct atttttgcgc gcggnnnnnn   300
nnnnnnnnnn nnnnnnnnnn nnnnnnnnnn tggggccaag gcaccaccct gaccgttagc   360
tcaagc                                                              366

<210> SEQ ID NO 193
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag'
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (313)..(315)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
```

```
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<221> NAME/KEY: modified_base
<222> LOCATION: (331)..(333)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 193
gaagtgcaat tgcagcagag cggtgcggaa ctggtgaaac cgggcagcag cgtgaaaatg    60
agctgcaaag cgtccggata tacctttacc agctactaca tctactggat taaacagcgt   120
ccgggccagg gcctcgagtg gattggccgt attggcaacc cgggtagcgg cgrtaccaam   180
tacaacgaaa aattcaaagg caaagcgacc tttaccgtgg ataaaagcag cagcaccgcg   240
tatatgcagc tgtccagcct gaccccggaa gataccgcgg tgtattactg cgcgcggnnn   300
nnnnnnnnnn nnnnnnnnnn nnnnnnnnnn nnntggggcc aaggcgtgat ggtgacggtt   360
agctcaagc                                                          369

<210> SEQ ID NO 194
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (295)..(297)
<223> OTHER INFORMATION: This region discloses a, c, t or g in any
      combination except 'taa', 'tga' or 'tag'
<220> FEATURE:
<221> NAME/KEY: modified_base
<222> LOCATION: (298)..(300)
<223> OTHER INFORMATION: This region discloses a, c, t or g in any
      combination except 'taa', 'tga' or 'tag'
<220> FEATURE:
<221> NAME/KEY: modified_base
<222> LOCATION: (301)..(303)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (304)..(306)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (307)..(309)
<223> OTHER INFORMATION: This region discloses a, c, t or g in any
      combination except 'taa', 'tga' or 'tag' or is not present
<220> FEATURE:
<221> NAME/KEY: modified_base
<222> LOCATION: (310)..(312)
<223> OTHER INFORMATION: This region discloses a, c, t or g in any
      combination except 'taa', 'tga' or 'tag' or is not present
<220> FEATURE:
```

```
<221> NAME/KEY: modified_base
<222> LOCATION: (313)..(315)
<223> OTHER INFORMATION: This region discloses a, c, t or g in any
      combinationexcept 'taa', 'tga' and 'tag' or is not present
<220> FEATURE:
<221> NAME/KEY: modified_base
<222> LOCATION: (316)..(318)
<223> OTHER INFORMATION: This region discloses a, c, t or g in any
      combination except 'taa', 'tga' or 'tag'
<220> FEATURE:
<221> NAME/KEY: modified_base
<222> LOCATION: (319)..(321)
<223> OTHER INFORMATION: This region discloses a, c, t or g in any
      combination except 'taa', 'tga' or 'tag'
<220> FEATURE:
<221> NAME/KEY: modified_base
<222> LOCATION: (322)..(324)
<223> OTHER INFORMATION: This region discloses a, c, t or g in any
      combination except 'taa', 'tga' or 'tag'
<220> FEATURE:
<221> NAME/KEY: modified_base
<222> LOCATION: (325)..(327)
<223> OTHER INFORMATION: This region discloses a, c, t or g in any
      combination except 'taa', 'tga' or 'tag'
<220> FEATURE:
<221> NAME/KEY: modified_base
<222> LOCATION: (328)..(330)
<223> OTHER INFORMATION: This region discloses a, c, t or g in any
      combination except 'taa', 'tga' or 'tag'
<220> FEATURE:
<223> OTHER INFORMATION: see specification as filed for detailed
      description of substitutions and preferred embodiments

<400> SEQUENCE: 194
gaagtgcaat tggtggaaag cggcggtggt ctggttcagc cgggtcgtag cctgaaactg      60
agctgcgcgg cgtccggatt tacctttagc aactatggca tggcgtgggt tcgccaggcg     120
ccgaccaaag gtctcgagtg ggtggcgacc attasctatg atggcagcar cacctattat     180
cgtgatagcg tgaaaggccg ttttaccatt agccgtgata acgcgaaaag caccctgtat     240
ctgcaaatgg atagcctgcg tagcgaagat accgcgacct attattgcgc gcggnnnnnn     300
nnnnnnnnnn nnnnnnnnnn nnnnnnnnnn tggggccaag cgtgatggt gacggttagc      360 tcaagc                                                                366

<210> SEQ ID NO 195
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Ile Val Met Thr Gln Ser Pro Ser Ser Leu Ala Val Ser Ala Gly
1               5                   10                  15

Glu Lys Val Ser Ile Ser Cys Arg Ser Ser Gln Ser Leu Val His Ser
            20                  25                  30

Asp Gly Lys Lys Thr Tyr Leu Asn Trp Tyr Leu Gln Lys Pro Gly Gln
        35                  40                  45

Ser Pro Gln Leu Leu Ile Tyr Trp Val Ser Asn Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Gly Gln
                85                  90                  95

Ala Thr His Ile Pro Tyr Thr Phe Gly Ala Gly Thr Lys Leu Glu Leu
```

Lys Arg Ala Asp Ala
        115

<210> SEQ ID NO 196
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Ser Pro Ser Ser Leu Ser Ala Ser Leu Gly
1               5                   10                  15

Asp Arg Val Thr Ile Glu Cys Lys Ala Ser Gln Asn Ile Tyr Lys Tyr
            20                  25                  30

Leu Ala Trp Tyr Gln Gln Lys Pro Gly Lys Ala Pro Lys Leu Leu Ile
        35                  40                  45

Tyr Asn Ala Asn Ser Leu Gln Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Tyr Asn Ser Tyr Pro Tyr
                85                  90                  95

Thr Phe Gly Ala Gly Thr Lys Leu Glu Leu Lys Arg Ala Asp Ala
            100                 105                 110

<210> SEQ ID NO 197
<211> LENGTH: 18
<212> TYPE: PRT
<213> ORGANISM: Rattus sp.

<400> SEQUENCE: 197

Tyr Tyr Trp Tyr Phe Asp Phe Trp Gly Pro Gly Thr Met Val Thr Val
1               5                   10                  15

Ser Ser

<210> SEQ ID NO 198
<211> LENGTH: 16
<212> TYPE: PRT
<213> ORGANISM: Rattus sp.

<400> SEQUENCE: 198

Asp Tyr Phe Asp Tyr Trp Gly Gln Gly Val Met Val Thr Val Ser Ser
1               5                   10                  15

<210> SEQ ID NO 199
<211> LENGTH: 16
<212> TYPE: PRT
<213> ORGANISM: Rattus sp.

<400> SEQUENCE: 199

Asn Trp Phe Ala Tyr Trp Gly Gln Gly Thr Leu Val Thr Val Ser Ser
1               5                   10                  15

<210> SEQ ID NO 200
<211> LENGTH: 17
<212> TYPE: PRT
<213> ORGANISM: Rattus sp.

<400> SEQUENCE: 200

```
Tyr Tyr Val Met Asp Ala Trp Gly Gln Gly Ala Ser Val Thr Val Ser
1               5                   10                  15

Ser

<210> SEQ ID NO 201
<211> LENGTH: 14
<212> TYPE: PRT
<213> ORGANISM: Rattus sp.

<400> SEQUENCE: 201

Trp Thr Phe Gly Gly Gly Thr Lys Leu Glu Leu Lys Arg Thr
1               5                   10

<210> SEQ ID NO 202
<211> LENGTH: 14
<212> TYPE: PRT
<213> ORGANISM: Rattus sp.

<400> SEQUENCE: 202

Asn Thr Phe Gly Ala Gly Thr Lys Leu Glu Leu Lys Arg Thr
1               5                   10

<210> SEQ ID NO 203
<211> LENGTH: 14
<212> TYPE: PRT
<213> ORGANISM: Rattus sp.

<400> SEQUENCE: 203

Asp Thr Phe Gly Ala Gly Thr Lys Leu Glu Leu Lys Arg Thr
1               5                   10

<210> SEQ ID NO 204
<211> LENGTH: 14
<212> TYPE: PRT
<213> ORGANISM: Rattus sp.

<400> SEQUENCE: 204

Tyr Thr Phe Gly Ala Gly Thr Lys Leu Glu Leu Lys Arg Thr
1               5                   10

<210> SEQ ID NO 205
<211> LENGTH: 14
<212> TYPE: PRT
<213> ORGANISM: Rattus sp.

<400> SEQUENCE: 205

Phe Thr Phe Gly Ser Gly Thr Lys Leu Glu Ile Lys Arg Thr
1               5                   10

<210> SEQ ID NO 206
<211> LENGTH: 14
<212> TYPE: PRT
<213> ORGANISM: Rattus sp.

<400> SEQUENCE: 206

Leu Thr Phe Gly Ser Gly Thr Lys Leu Glu Ile Lys Arg Thr
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
       peptide
<220>  FEATURE:
<221>  NAME/KEY: MOD_RES
<222>  LOCATION: (3)..(3)
<223>  OTHER INFORMATION: Ser or Thr
<220>  FEATURE:
<221>  NAME/KEY: MOD_RES
<222>  LOCATION: (8)..(8)
<223>  OTHER INFORMATION: Ser, Asn or Tyr
<220>  FEATURE:
<223>  OTHER INFORMATION: see specification as filed for detailed
       description of substitutions and preferred embodiments

<400>  SEQUENCE: 207

Thr Ile Xaa Tyr Asp Gly Ser Xaa Thr Tyr
1               5                   10
```

RODENT COMBINATORIAL ANTIBODY LIBRARIES

CROSS REFERENCE TO RELATED APPLICATIONS

This application claims the benefit of U.S. provisional application Ser. No. 61/299,380 filed Jan. 29, 2010, which is incorporated by reference in its entirety.

SEQUENCE LISTING

The instant application contains a Sequence Listing which has been submitted via EFS-Web and is hereby incorporated by reference in its entirety. Said ASCII copy, created on Oct. 5, 2012, is named MS100US.txt and is 120,516 bytes in size.

FIELD OF THE INVENTION

The present invention relates to and provides rodent libraries, such as combinatorial antibody libraries which are suitable for selection of fully rodent antibodies, e.g. murine or rat antibodies. The invention also relates to synthetic nucleic acid sequences which encode individual or collections of rodent antibodies, i.e. nucleic acid sequences encoding rodent antibody libraries. Methods for generating and using such libraries are provided. In particular, the invention relates to the preparation of a library of rodent-derived antibody genes by the use of synthetic consensus and/or closest homologs to germline sequences which cover the structural repertoire of antibodies encoded in the genome.

BACKGROUND OF THE INVENTION

Over the last several years, many humanized or fully human antibodies have been tested in clinical trials, and several of them have been approved for therapeutic application (Hoogenboom, H. R. (2005), Nat Biotechnol 23, 1105-1116; Carter, P. J. (2006). Nat Rev Immunol 6, 343-357). Although the human antibodies typically selected by phage display (Hoogenboom, 2005) are not likely to be immunogenic and therefore quickly neutralized in human, they usually suffer from rapid clearance in experimental animals due to induction of anti-human antibodies. The rapid clearance of human antibodies prevents long-term target-validation, mechanistic and ADME (PK/PD) preclinical studies in rodents. For these reasons, it is highly desirable to have available antibodies which are not immunogenic in the respective animal models. Most preferably, such antibodies are fully derived from the respective animal species. For example, an antibody used in murine animal experiments is ideally a fully murine antibody. Likewise, an antibody used in rat animal experiments is ideally a fully rat antibody.

For the generation of human antibodies synthetic combinatorial antibody libraries have been used, e.g. the HuCAL GOLD library described in Rothe et al., 2008, *J Mol Biol* 376, 1182-1200. The selection by phage display of well expressed, target-selective high affinity-binders was demonstrated in these fully human library (Steidl et al. 2008. *Mol Immunol* 46(1):135-44). Synthetic combinatorial libraries offer several advantages over libraries derived from naïve B-cell sources. Natural occurring gene sequences encoding antibody frameworks can be chosen and readily designed for high antibody-production yield in prokaryotic or eukaryotic hosts, e.g. by codon-optimization. Also, the synthetic nature of the libraries enables the implementation of other features, e.g. a modular design of the antibody frameworks with unique restriction sites. Such willfully introduced restriction sites at appropriate positions enable downstream optimization processes such as antibody maturation; for example, pools of binders can be rapidly optimized without knowledge of particular sequences using pre-built diversified complementarity determining region (CDR) cassettes. Mostly this optimization process is driven for a higher antigen affinity and then known as affinity maturation (Steidl et al. 2008. *Mol Immunol* 46(1):135-44).

A similar approach was not deemed to be possible for rodent antibody libraries. Numerous reports demonstrate the belief in the scientific community that, e.g., mouse antibody libraries cannot be produced with sufficient complexity and/or with reasonably useful expression levels. Historically, mouse antibody-libraries were derived by PCR amplification of a VH-gene pool from spleens of immunized mice (Ward et al., 1989, *Nature* 341, 544-546). However, such libraries were fraught with problems, such as for example poor expression of the library members.

Only recently, the first synthetic mouse antibody library has been reported (Cobaugh et al., 2008, *Journal of Molecular Biology* 378, 622-633). But there, the library was focused towards peptide binders, based on single framework derived from antibody 26-10, and highly diversified in HCDR3 only.

WO 06/030238 describes the "surprising discovery that an antibody framework region based on a murine VH14 heavy chain and a murine VK2 light chain [ . . . ] is solubly expressed in a microorganism and is stable [ . . . ]". See lines 15-28 on page 3 of WO 06/030238. This summarizes all previous, failed attempts in the art to come up with similar murine or other rodent libraries. Notably, WO 06/030238 only reported on the soluble expression of one—and only one—particular VH/VL pair. Accordingly, no other rodent libraries were reported so far as having been successful. Further, no rodent antibody library comprising more than one specific VH/VL pair has been disclosed.

Despite these discouraging references, the present inventors aimed for the generation of antibody libraries of a rodent nature, such as a fully murine and fully rat nature, respectively, and/or collectively. Such libraries could prove suitable for the selection of fully murine and rat antibodies with desired biophysical properties and target specificity. One of the main aims was to build a synthetic fully murine combinatorial antibody library (hereinafter HuCAL MOUSE) and a fully rat combinatorial antibody library (hereinafter HuCAL RAT), preferably comprising as many distinct VL/VH-frameworks as possible.

WO 01/92291 describes a method for the RNA trans-splicing mediated covalent intracellular fusion of transcripts of two different genes. In Example 9a mouse library of dTS (double trans splicing) genes is constructed by comparing and the leader exons of 41 functional mouse VH genes. No mouse antibody libraries were however generated.

De Jaeger et al (FEBS Letters (1997) 403, 116-22) use a single-chain murine phage display library for the isolation of binders against an enzyme from *Petunia hybrida*. This library is however not a synthetic library. Furthermore the library of de Jaeger et al. is derived from immunized mice, i.e. the library was generated from nucleic acid material that has been pre-exposed to the antigen.

Sommavilla et al (J Immunol Methods (2010) 353, 31-43) report the design and construction of a naive mouse antibody library. Like other attempts, the libraries of Sommavilla et al. only contain one VH and one VL germline gene.

To the inventors' knowledge, neither a synthetic rodent antibody library nor any other reliable rodent antibody library with a diverse VH/VL composition previously has been disclosed which comprises members of more than one VH and/or more than one VL germline family. One of the breakthroughs in the instant invention is based on the observation that different frameworks impose distinct conformations on CDRs, and hence affect the range of antibody-structures capable of antigen binding. This is one of the main problems in the generation of rodent antibodies, and one of the reasons why up until now no rodent antibody library as contemplated by the present invention has been generated. For the first time it was possible overcome the prejudice in the prior art. Rational analysis of the naturally occurring rodent antibody sequences and sophisticated design of the libraries, led to the first synthetic rodent antibody libraries that are broadly useful for biomedical research.

SUMMARY OF THE INVENTION

Since frameworks encoded by murine germline sequences are expected not to be immunogenic in mice, we searched in the IMGT database (Giudicelli, et al. (1997), *Nucleic Acids Res* 25, 206-211) for germline sequences representing classes of the most abundant murine antibodies. We tested six representative murine VL kappa germline sequences (3 for C57BL/6 mouse strain and 3 for Balb/c mouse strain) and five representative murine VH germline sequences (plus a variant of a mVH1 germline sequence, termed mVH1_RV). Out of the 36 possible mVL-mVH combinations we identified five combinations which exhibited the following advantageous properties: (i) they are well displayed on the tip of filamentous phages in Fab-format, (ii) they are expressed in high amounts and in soluble form in Fab-format, as well as in IgG formats, (iii) they are thermodynamically stable, and (iv) they are identified frequently in the Kabat antibody-database.

For the five most favorable mVL-mVH combinations the L-CDR3 and the H-CDR3 regions were replaced by highly diversified L-CDR3 and H-CDR3 library cassettes, respectively, thereby achieving an overall library diversity of more than $1 \times 10^{10}$ For the purpose of affinity-maturation of binders obtained from initial panning rounds, L-CDR3 and H-CDR2 maturation cassettes were synthesized and cloned into auxiliary vector.

Besides the modularity, other features of the HuCAL GOLD-system (Rothe et al., 2008, J Mol Biol 376, 1182-1200), were implemented as well, e.g. the CysDisplay® technology (see WO 00/105950). Binders selected from the synthetic rodent antibody-library can for example be used for target validation in mouse. Furthermore, selected murine or rat antibodies exhibiting a similar binding mode as their HuCAL GOLD-derived target-specific counterparts may be used as non-immunogenic surrogates in respective animal experiments, for example for toxicology and pharmacology studies.

The present invention relates generally to synthetic rodent antibody libraries, preferably libraries comprising members of at least two VH germline families and/or at least two VL germline families. Specifically the present invention provides synthetic mouse and rat antibody libraries, although libraries of other rodent species are contemplated by the invention.

The present invention also provides synthetic rodent antibody libraries comprising more than 50% of the natural mouse VH repertoire and/or more than 50% of the natural mouse VL repertoire. Said libraries furthermore cover more than 50% of the naturally occurring H-CDR3 lengths of the murine H-CDR3 repertoire.

The present invention also provides synthetic rodent antibody libraries in which essentially all VH-VL combinations of said library are efficiently displayed.

The present invention also provides synthetic rodent antibody libraries in which essentially all VH-VL combinations are well expressed in *E. coli* in Fab format.

The present invention also provides synthetic rodent antibody libraries in which wherein essentially all VH-VL combinations are well expressed in a mammalian system in IgG format.

The present invention also provides synthetic rodent antibody libraries in which all VH-VL combinations are thermally stable.

The present invention also provides collections of nucleic acid molecules encoding the antibodies of said synthetic rodent antibody libraries.

The present invention also provides vectors encoding said nucleic acid molecules.

The present invention also provides recombinant host cells comprising said nucleic acid molecules or vectors.

The present invention also provides methods to isolate antibodies specific for an antigen, said method comprising the steps of:

(a) contacting the synthetic rodent antibody libraries of the present invention with an antigen;
(b) removing those members of the library which do not bind to (or are not specific for) the antigen; and
(c) recovering those members of the library bound to (or specific for) the antigen.

The present invention also provides an antibody isolated from a library contemplated by the present invention, including a modified isolate such as a humanized antibody. The present invention also provides an antibody variant derived from an antibody isolated from a library contemplated by the present invention, including antibody variants, wherein said antibody variant is a humanized antibody.

The selection of the frameworks was chosen to optimize the chance of obtaining antibodies which possess favourable biophysical properties and which are devoid of short comings of antibodies derived from synthetic libraries which have not undergone in-vivo maturation. Such favorable and desired biophysical properties include higher stability, higher expression levels and a low tendency for aggregation.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, advantages, and aspects of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows an alignment of framework region 3 of mVH1 (SEQ ID NO: 145) and the variant mVH1_RV (SEQ ID NO: 146). This variant comprises K77R and T78V mutations. In this variant a stabilising salt bridge is formed between R77 and D100, which adds extra high stability.

FIG. 2 shows framework region 4 for the heavy chains (SEQ ID NOS 147-150, respectively, in order of appearance) and the mouse library.

FIGS. 4 a-b show the natural amino acid distribution of murine HCDR3 sequences for HCDR3 sequences of the length of 7, 8, 9, 10, 11 and 12 amino acids. Single amino acid distributions are aligned by grouping for the D-segment (leading to a right-centred alignment).

FIG. 5 summarizes all lengths in one murine HCDR3 design. The weighted average was calculated for each position.

FIG. 6 shows the murine HCDR3 design after implementing all required modifications.

FIG. 8 shows the murine LCDR3 design (residues 87-100 of SEQ ID NO: 168) after implementing all required modifications.

FIG. 11 shows the murine HCDR2 design after implementing all required modifications.

FIGS. 17 a-b show an overview of expression yields of all tested mouse framework combinations after washing on IMAC with and without isopropanol in a color code for selection criteria.

FIG. 20 depicts the representation of the actual amino acids found in the LCDR3 of the murine library of the present invention, as compared to the predicted occurrence the these residues. "T" in the second row refers to trinucleotide mixtures used for the synthesis of the diversified oligonucleotides for the CDR cassette. Letters "F" and "P" indicate found and planned residue occurrence, respectively.

FIG. 21 depicts the representation of the actual amino acids found in the HCDR3 of the murine library of the present invention, as compared to the predicted occurrence the these residues. "T" and "W" in the second row refers to trinucleotide mixtures and wobble nucleotides, respectively, used for the synthesis of the diversified oligonucleotides for the CDR cassette. Letters "F" and "P" indicate found and planned residue occurrence, respectively.

FIG. 22 depicts the representation of the actual amino acids found in the HCDR2 maturation cassette of the murine VH1 RV sublibrary of the present invention, as compared to the predicted occurrence the these residues. "MMT" and "W" in the second row refers to trinucleotide mixtures and wobble nucleotides, respectively, used for the synthesis of the diversified oligonucleotides for the maturation cassette. Letters "F" and "P" indicate found and planned residue occurrence, respectively.

FIG. 23 depicts the representation of the actual amino acids found in the HCDR2 maturation cassette of the murine VH2 sublibrary of the present invention, as compared to the predicted occurrence the these residues. "MMT" and "W" in the second row refers to trinucleotide mixtures and wobble nucleotides, respectively, used for the synthesis of the diversified oligonucleotides for the maturation cassette. Letters "F" and "P" indicate found and planned residue occurrence, respectively.

FIG. 24 depicts the representation of the actual amino acids found in the HCDR2 maturation cassette of the murine VH5 sublibrary of the present invention, as compared to the predicted occurrence the these residues. "MMT" and "W" in the second row refers to trinucleotide mixtures and wobble nucleotides, respectively, used for the synthesis of the diversified oligonucleotides for the maturation cassette. Letters "F" and "P" indicate found and planned residue occurrence, respectively.

Figure 25:
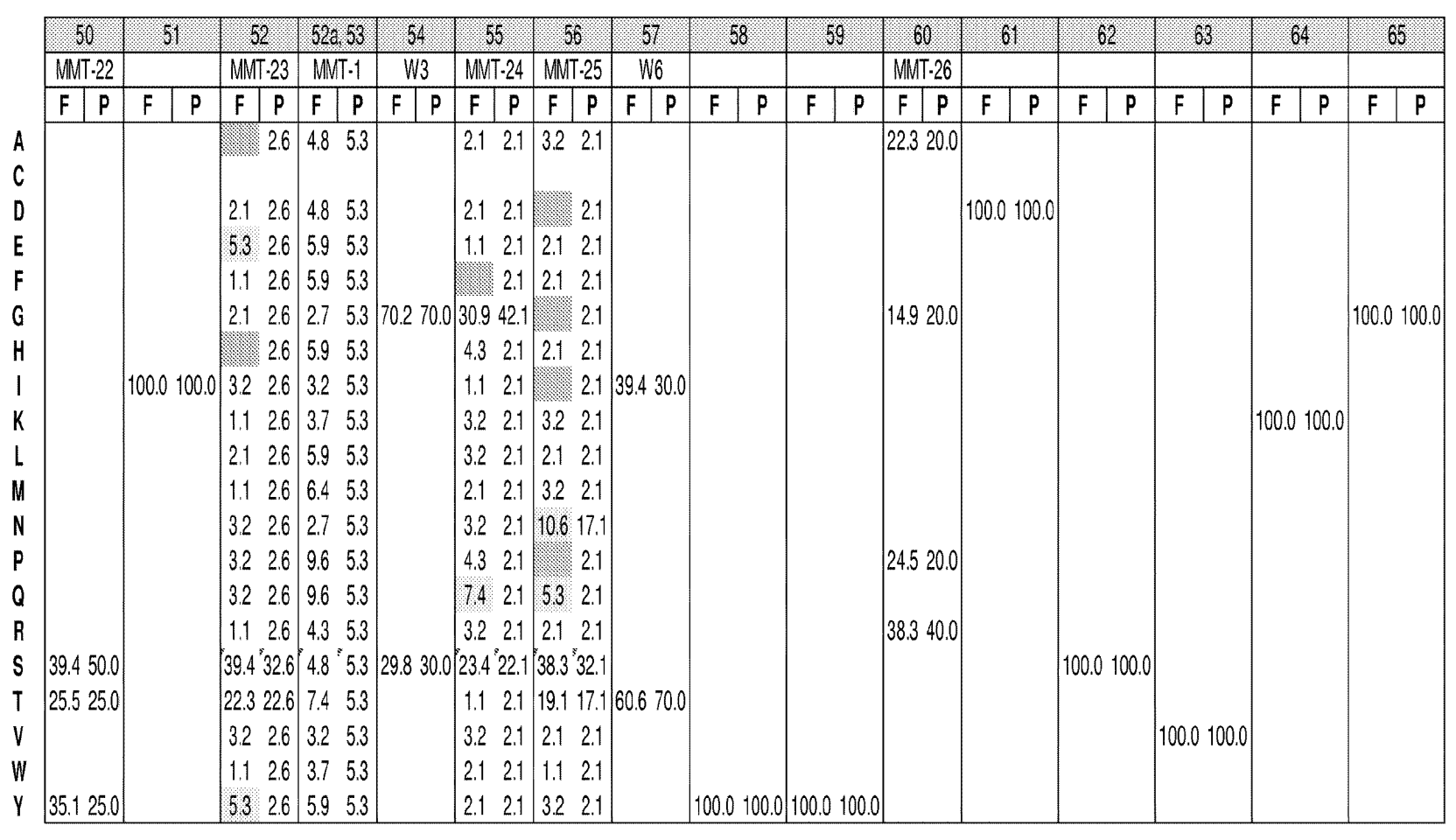

FIG. 25 depicts the representation of the actual amino acids found in the HCDR2 maturation cassette of the rat library of the present invention, as compared to the predicted occurrence the these residues. "MMT" and "W" in the second row refers to trinucleotide mixtures and wobble nucleotides, respectively, used for the synthesis of the diversified oligonucleotides for the maturation cassette. Letters "F" and "P" indicate found and planned residue occurrence, respectively.

FIG. 36 shows framework 4 region of the rat VH mastergene (SEQ ID NOS 197-200, respectively, in order of appearance)

FIG. 42 shows an overview of expression yields of all tested Fab rat framework combinations after washing on IMAC with and without isopropanol in a color code for selection criteria.

FIG. 44 shows the variability introduced in the HCDR2 of the naïve HuCAL rat library (SEQ ID NO: 207).

DETAILED DESCRIPTION OF THE INVENTION

Figure 3:
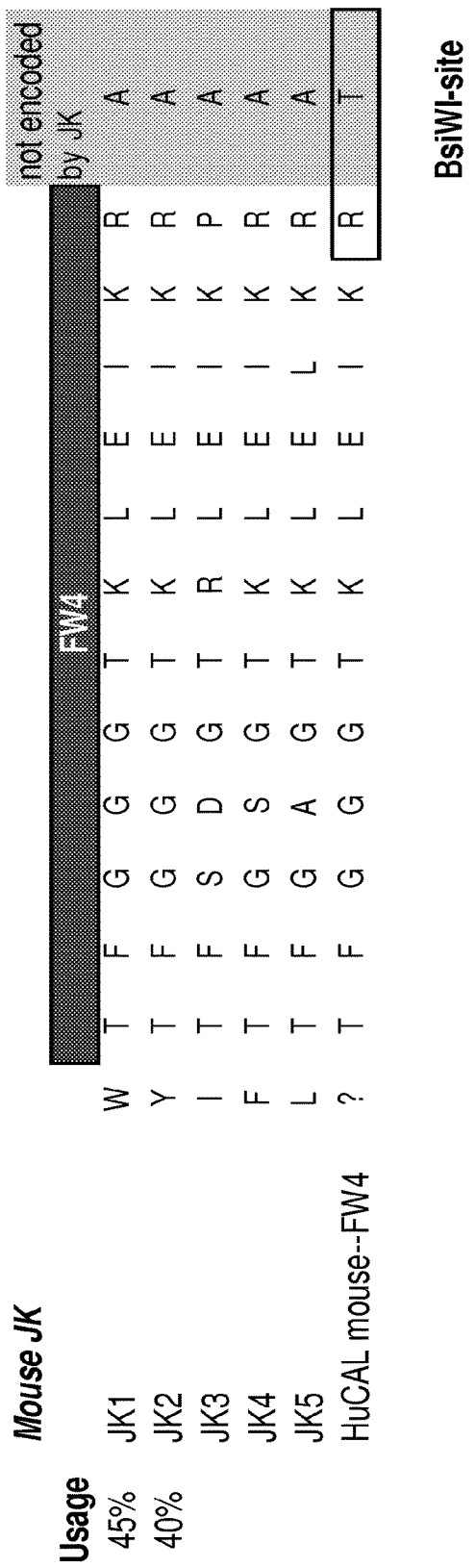
FIG. 3 shows framework region 4 for the light chains (SEQ ID NOS 151-156, respectively, in order of appearance) and the mouse library.

Unless defined otherwise, all technical and scientific terms used herein have the same meaning as commonly understood by those of ordinary skill in the art to which this invention pertains.

The terms "about" or "approximately" in the context of numerical values and ranges refers to values or ranges that approximate or are close to the recited values or ranges such that the invention can perform as intended, such as having a desired number or percentage of sequence homology, as is apparent to the skilled person from the teachings contained herein. This is due, at least in part, to the varying culture conditions and the variability of biological systems. Thus, these terms encompass values beyond those resulting from systematic error. These terms make explicit what is implicit.

All ranges set forth herein in the summary and description of the invention include all numbers or values thereabout or therebetween of the numbers of the range. The ranges of the invention expressly denominate and set forth all integers, decimals and fractional values in the range. The term "about" can be used to describe a range.

The term "antibody" as used herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "antigen binding portion" or "fragment" of an antibody are used equivalently in the present application. These terms refer to one or more fragments of an intact antibody that retain the ability to specifically bind to a given antigen. Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain; and an isolated complementarity determining region (CDR). Preferred antigen binding portions or fragments of antibodies are Fab fragments.

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "high affinity" for an antibody, such as an IgG antibody, refers to an antibody having a $K_D$ of $10^{-8}$ M or less, $10^{-9}$ M or less, or $10^{-10}$ M, or $10^{-11}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

The term "binding specificity" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

Specific binding between two entities means a binding with an equilibrium constant ($K_A$) of at least $1\times10^7$ M$^{-1}$, $10^8$ M$^{-1}$, $10^9$ M$^{-1}$, $10^{10}$ M$^{-1}$, or $10^{11}$ M$^{-1}$. The phrase "specifically (or selectively) binds" to an refers to a binding reaction that is determinative of the presence of a cognate in a heterogeneous population of proteins and other biologics. In addition to the equilibrium constant ($K_A$) noted above, an antibody of the invention typically also has a dissociation rate constant (Kd) of about $1\times10^{-2}$ s$^{-1}$, $1\times10^{-3}$ s$^{-1}$, $1\times10^{-4}$ s$^{-1}$, $1\times10^{-4}$ s$^{-1}$, or lower, and binds to a target antigen with an affinity that is at least two-fold greater than its affinity for binding to a non-specific antigen. The phrases "an antibody recognizing an antigen" and "an antibody specific for an antigen" are used interchangeably herein with the term "an antibody which binds specifically to an antigen".

The terms "cross-block", "cross-blocked" and "cross-blocking" are used interchangeably herein to mean the ability of an antibody or other binding agent to interfere with the binding of other antibodies or binding agents to the same target in a standard competitive binding assay.

The ability or extent to which an antibody or other binding agent is able to interfere with the binding of another antibody or binding molecule to the same target, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced immunogenicity in human as compared to the original mouse antibody.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but is not limited to Xoma technology disclosed in U.S. Pat. No. 5,766,886.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "rodent antibody", as used herein, is intended to include antibodies having variable regions in which both the framework and CDR regions are derived from sequences of rodent origin. For example both, the framework and CDR regions may be derived from sequences of mouse origin, or both the framework and CDR regions may be derived from sequences of rat origin. Furthermore, if the antibody contains a constant region, the constant region also is derived from such rodent sequences, e.g., rodent germline sequences, or mutated versions of rodent germline sequences. The rodent antibodies of the invention may include amino acid residues not encoded by rodent sequences (e.g., mutations introduced by random or site-specific mutagenesis in vitro or by somatic mutation in vivo).

The term "rodent" is art recognized and includes the following species: mouse, rat, squirrel, chipmunk, gopher, porcupine, beaver, hamster, gerbil, guinea pig, degu, chinchilla, prairie dog, and groundhog. In certain aspects of the present invention said mouse is selected from the laboratory strains Balb/c and C57BL/6.

The term "isolated antibody" refers to an antibody that is substantially free of other antibodies having different antigenic. An isolated antibody that specifically binds to an antigen may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The terms "monoclonal antibody" or "monoclonal antibody composition" as used herein refer to a preparation of antibody molecules of single molecular composition. A monoclonal antibody composition displays a single binding specificity and affinity for a particular epitope.

Antibody libraries can be derived from immunoglobulins, or fragments thereof, that are biased towards certain specificities present in immunized animals or naturally immunized, or infected, humans. Alternatively, antibody libraries can be derived from naïve immunoglobulins, or fragments thereof, i.e. immunoglobulins that are not biased towards specificities found in the immune system. Such libraries are referred to as "unbiased" libraries. In preferred embodiments the present invention provides unbiased antibody libraries, i.e. the libraries are not pre-exposed to the antigen of interest. Due to the absence of any bias, such libraries comprise antibodies binding to any potential target antigen of interest Typically, immune antibody libraries are constructed with VH and VL gene pools that are cloned from source B cells by PCR-based (or related) cloning techniques. In the same way it is also possible to generate unbiased, naïve antibody libraries. Unbiased, naïve antibody libraries can however also be generated in a synthetic way in which the entire library is constructed entirely in vitro. Recombinant DNA technology is employed and may be used to mimic the natural biases and redundancies of the natural antibody repertoire. Such antibody libraries are referred to as "synthetic" antibody libraries. The term "fully synthetic" library refers to antibody libraries which are completely, i.e. fully, de novo constructed by DNA synthesis, e.g. by total gene synthesis, PCR-based methods, or related DNA technologies. In such libraries the entire DNA is constructed de novo, i.e. the part encoding the CDRs, as well as the parts (e.g. the framework regions) encoding the parts surrounding the CDRs of the antibodies of the library. The terms "synthetic" and "fully synthetic" therefore refer to the de novo origin of the DNA. In contrast, in a "semi-synthetic" antibody library only parts of the antibodies of the library are constructed de novo, whereas other parts, e.g. certain CDR regions, are derived from natural sources. (numerous reviews on this matter exist, see e.g. Sidhu et al.; Nat Chem Biol (2006), 2, 682-8). In certain aspects, the present invention provides a synthetic rodent antibody library. In preferred aspect, the present invention provides a fully synthetic rodent antibody library.

The term "library" refers to a collection of distinct molecules comprising typically more than $10^3$, more than $10^4$, more than $10^5$, more than $10^6$, more than $10^7$, more than $10^8$, more than $10^9$ or even more than $10^{10}$ members. A library in the context of the present invention is a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a certain aspect, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants. The term "collection" is essentially used interchangeably with the term "library".

The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package, www.gcg.com, using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "recombinant antibody", as used herein, includes all antibodies that are prepared, expressed, created or isolated by recombinant means, such as antibodies isolated from an animal (e.g., a mouse) that is transgenic or transchromosomal for rodent immunoglobulin genes or a hybridoma prepared therefrom, antibodies isolated from a host cell transformed to express rodent human antibody, e.g., from a transfectoma, antibodies isolated from a recombinant, combinatorial rodent antibody library, and antibodies prepared, expressed, created or isolated by any other means that involve splicing of all or a portion of a rodent immunoglobulin gene, sequences to other DNA sequences. Such recombinant rodent antibodies have variable regions in which the framework and CDR regions are derived from rodent germline immunoglobulin sequences. In certain embodiments, however, such recombinant rodent antibodies can be subjected to in vitro mutagenesis (or, when an animal transgenic for rodent Ig sequences is used, in vivo somatic mutagenesis) and thus the amino acid sequences of the VH and VL regions of the recombinant antibodies are sequences that, while derived from and related to rodent germline VH and VL sequences, may not naturally exist within the rodent antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Restriction sites that are "unique" are restriction sites that exist or appear only once on a given nucleic acid molecule. Typically such a nucleic acid molecule is a vector which encodes the library members of the present invention.

The term "mVL" is abbreviated for variable domain of the murine light immunoglobulin chain. The term "mVH" is abbreviated for variable domain of the murine heavy immunoglobulin chain. The term "rVL" is abbreviated for variable domain of the rat light immunoglobulin chain. The term "rVH" is abbreviated for variable domain of the rat heavy immunoglobulin chain. The term "IMGT" is abbreviated for ImMunoGeneTics, an on-line database, (Giudicelli, et al. (1997), *Nucleic Acids Res* 25, 206-211)).

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compositions or antibodies to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The term "position-dependent amino-acid usage" refers to the likelihood of occurrence of a particular amino acid sequence at a given position in a polypeptide. In the present invention, the position-dependent amino acid usage was determined for the re-arranged amino acid sequences classified by the individual germline gene. This enables the individual, precise design of the CDRs within its natural germline context.

In certain aspects the present invention provides a synthetic rodent antibody library which comprises members of at least two germline families. In other aspects said library comprises members of at least three, at least four or at least five germline families. In preferred aspects said synthetic rodent antibody library is a murine rodent library. In other aspects said synthetic rodent antibody library is a rat rodent library In certain aspects the present invention provides a synthetic murine antibody library which comprises more than 50% of the natural mouse VH repertoire. In other aspects said library comprises more than 60%, more than 70%, more than 75%, more than 80%, more than 85%, more than 90% or more than 95% of the natural mouse VH repertoire.

In certain aspects the present invention provides a synthetic murine antibody library which comprises members of at least two VH germline families. In other aspects said library comprises members of at least three, at least four or at least five VH germline families. In certain aspects said VH germline families are selected from VH1, VH2, VH3, VH5 and VH9.

In certain aspects the present invention provides a synthetic murine antibody library which comprises more than 50% of the natural mouse VL repertoire. In other aspects said library comprises more than 60%, more than 70%, more than 75%, more than 80%, more than 85%, more than 90% or more than 95% of the natural mouse VL repertoire.

In certain aspects the present invention provides a synthetic murine antibody library which comprises members of at least two VL germline families. In other aspects said library comprises members of at least three VL germline families. In certain aspects said VL germline families are VL-kappa germline families selected from VL1, VL3, VL7, VL8 and VL19.

In certain aspects the present invention provides a synthetic murine antibody library which comprises at least one, at least two, at least three, at least four or at least five of the following VH germline genes: IGHV1-72*01 (VH1), IGHV2-2*01 (VH2), IGHV3-6*01 (VH3), IGHV5-9*04 (VH5), and IGHV9-3*01 (VH9). In other aspects the present invention provides a synthetic murine antibody library which comprises the following VH germline genes: IGHV1-72*01 (VH1), IGHV2-2*01 (VH2), and IGHV5-9*04 (VH5), In certain embodiments the present invention provides a synthetic murine antibody library which comprises a variant VH1 germline gene IGHV1-72*01 which contains a K77R and/or a T78V mutation. In certain aspects said variant VH1 germline gene IGHV1-72*01 contains K77R mutation. In other aspects said variant contains a T78V mutation. In preferred aspects said variant contains a K77R and a T78V mutation.

In certain aspects the present invention provides a synthetic murine antibody library which comprises at least one, at least two, at least three, at least four, at least five or at least six of the following VL-kappa germline genes: IGKV1-117*01 (Vk1), IGKV3-12*01 (Vk3), IGHV3-4*01 (Vk3), IGHV7-33*01 (Vk7), IGHV8*21*01 (Vk8) and GHV19-93*01 (Vk19). In other aspects the present invention provides a synthetic murine antibody library which comprises at least two of the following VL-kappa germline genes: IGKV1-117*01 (Vk1), IGKV3-12*01 (Vk3), and IGHV3-4*01 (Vk3).

In certain aspects the present invention provides a synthetic murine antibody library which comprises the VH germline genes IGHV1-72*01 (VH1), IGHV2-2*01 (VH2), and IGHV5-9*04 (VH5) and at least two of the following VL-kappa germline genes: IGKV1-117*01 (Vk1), IGKV3-12*01 (Vk3), and IGHV3-4*01 (Vk3).

In certain aspects of the present invention the germline genes require modification in order to include restriction sites and to achieve modularity of the library. Therefore, in certain aspects the present invention provides a synthetic murine antibody library comprising one or more of the following modified germline genes: IGHV1-72*01 with a Q1E mutation; IGHV1-72*01 with a Q1E, a K77R and a A78V mutation; IGHV2-2*01 with a Q1E mutation; IGHV3-6*01 with a D1E and a T26S mutation; IGHV5-9*04 with a K3Q mutation; IGHV9-3*01 with a Q1E, a I2V and a K53E mutation and IGKV1-117*01 with a V2I mutation.

In certain embodiments the present invention provides a synthetic murine antibody library which comprises H-CDR3s which cover more than 50% of the naturally occurring H-CDR3 lengths of the murine H-CDR3 repertoire. In other aspects said library comprises more than 60%, more than 70%, more than 75%, more than 80%, more than 85%, more than 90% or more than 95% of the naturally occurring H-CDR3 lengths of the murine H-CDR3 repertoire.

In certain aspects the present invention provides a synthetic murine antibody library which comprises H-CDR3s of the length of 7-12 amino acids. In other aspects the present invention provides a synthetic murine antibody library which comprises H-CDR3s of the length of 7 amino acids and/or 8 amino acids and/or 9 amino acids and/or 10 amino acids and/or 11 amino acids and/or 12 amino acids.

In certain aspects the present invention provides a synthetic murine antibody library which comprises a H-CDR3 design as shown in FIG. 5 or FIG. 6. In certain aspects the present invention provides a synthetic murine antibody library which comprises a H-CDR3 design as shown in FIG. 6.

In certain aspects the present invention provides a synthetic murine antibody library in which the H-CDR3 region has a diversity of at least $1.0*10^8$. In other aspects the present invention provides a synthetic murine antibody library which the H-CDR3 region has a diversity of at least $1.0*10^9$, of at least $1.0*10^{10}$, of at least $1.0*10^{11}$, of at least $1.0*10^{12}$ or of at least $1.0*10^{13}$.

In certain aspects the present invention provides a synthetic murine antibody library which comprises L-CDR3s which cover more than 80% of the naturally occurring L-CDR3 lengths of the murine L-CDR3 repertoire. In other aspects said library comprises more than 85%, more than 90% or more than 95% of the naturally occurring L-CDR3 lengths of the murine L-CDR3 repertoire.

In certain aspects the present invention provides a synthetic murine antibody library which comprises a L-CDR3 of the length of 8 amino acids. In certain aspects the present invention provides a synthetic murine antibody library in which the L-CDR3 of essentially all members of the library is of the length of 8 amino acids.

Figure 7:
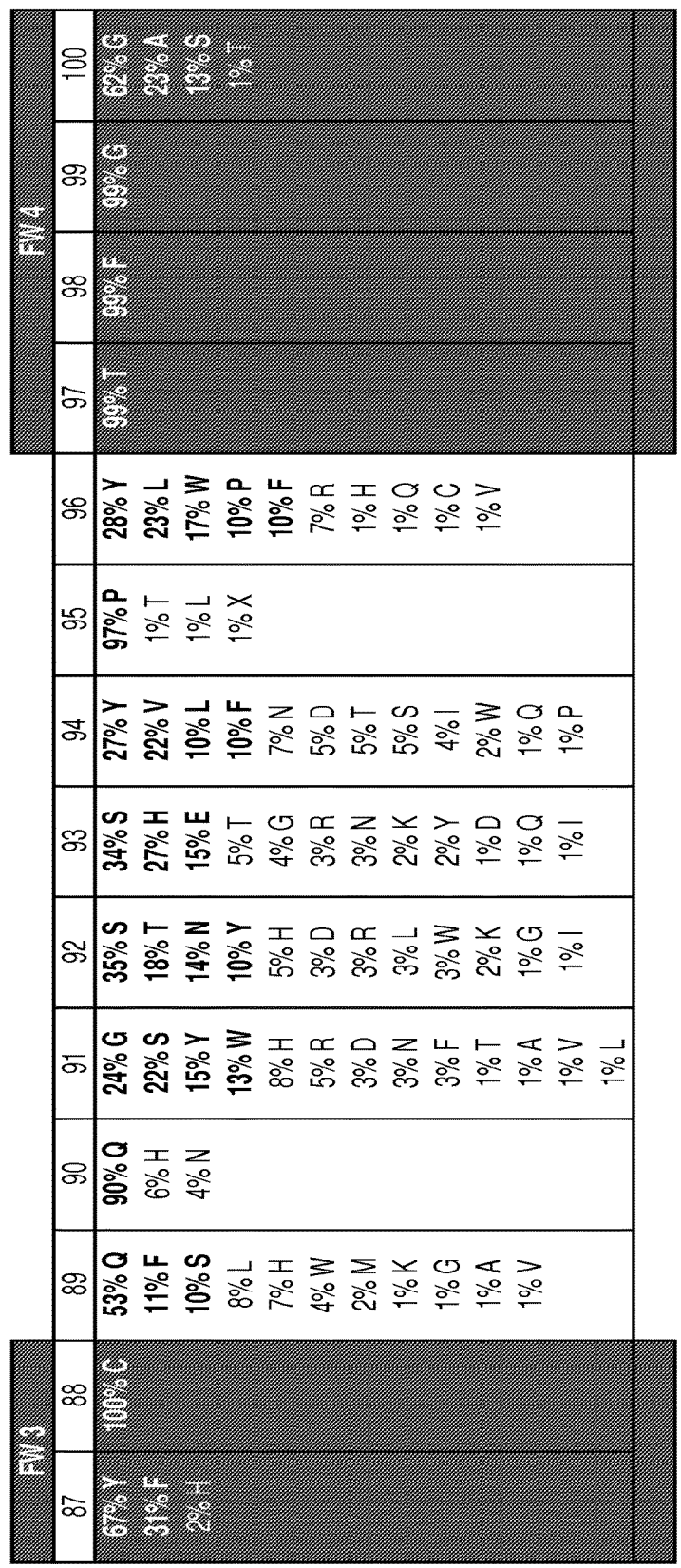
FIG. 7 shows the natural amino acid distribution of murine LCDR3 sequences of the length of 8 amino acids.

In certain aspects the present invention provides a synthetic murine antibody library which comprises a L-CDR3 design as shown in FIG. 7 or FIG. 8. In certain aspects the present invention provides a synthetic murine antibody library which comprises a L-CDR3 design as shown in FIG. 8.

In certain aspects the present invention provides a synthetic murine antibody library in which the L-CDR3 region has a diversity of at least $1.0*10^4$. In other aspects the present invention provides a synthetic murine antibody library which the L-CDR3 region has a diversity of at least $1.0*10^5$, of at least $1.0*10^6$ or of at least $1.0*10^7$.

In certain aspects the present invention provides a synthetic murine antibody library in which at least one of amino acid residues 52, 52a, 54, 56 and 58 (Kabat numbering) of the H-CDR2 is diversified. In other aspects the present invention provides a synthetic murine antibody library in which at least two, at least three, at least four or at least five of amino acid residues 52, 52a, 54, 56 and 58 (Kabat numbering) of the H-CDR2 are diversified.

Figure 10:
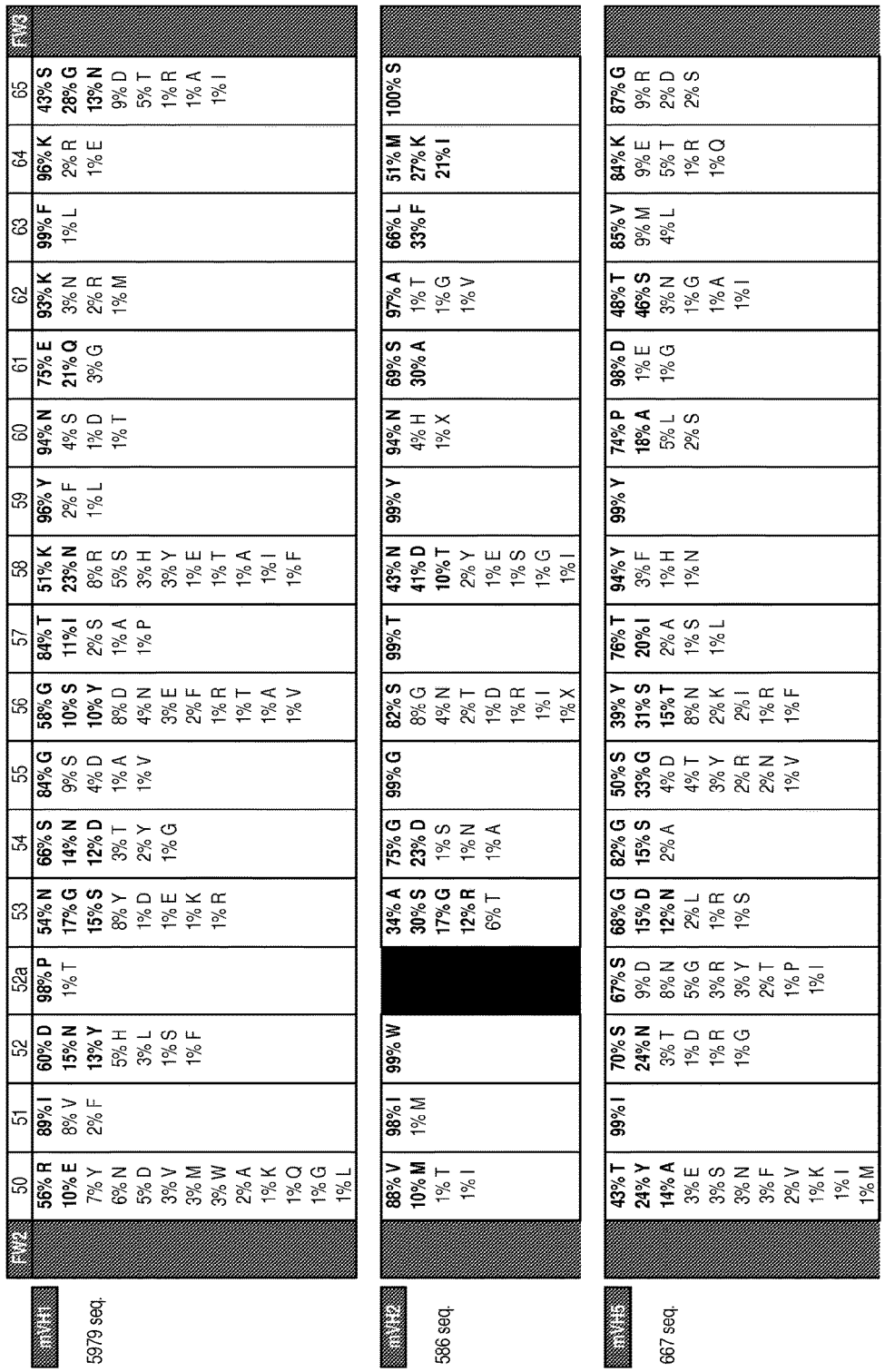
FIG. 10 summarizes the position-dependent amino acid distribution of the HCDR2 of the three selected mVH mastergenes (SEQ ID NOS 160-162, respectively, in order of appearance).
Figure 11:
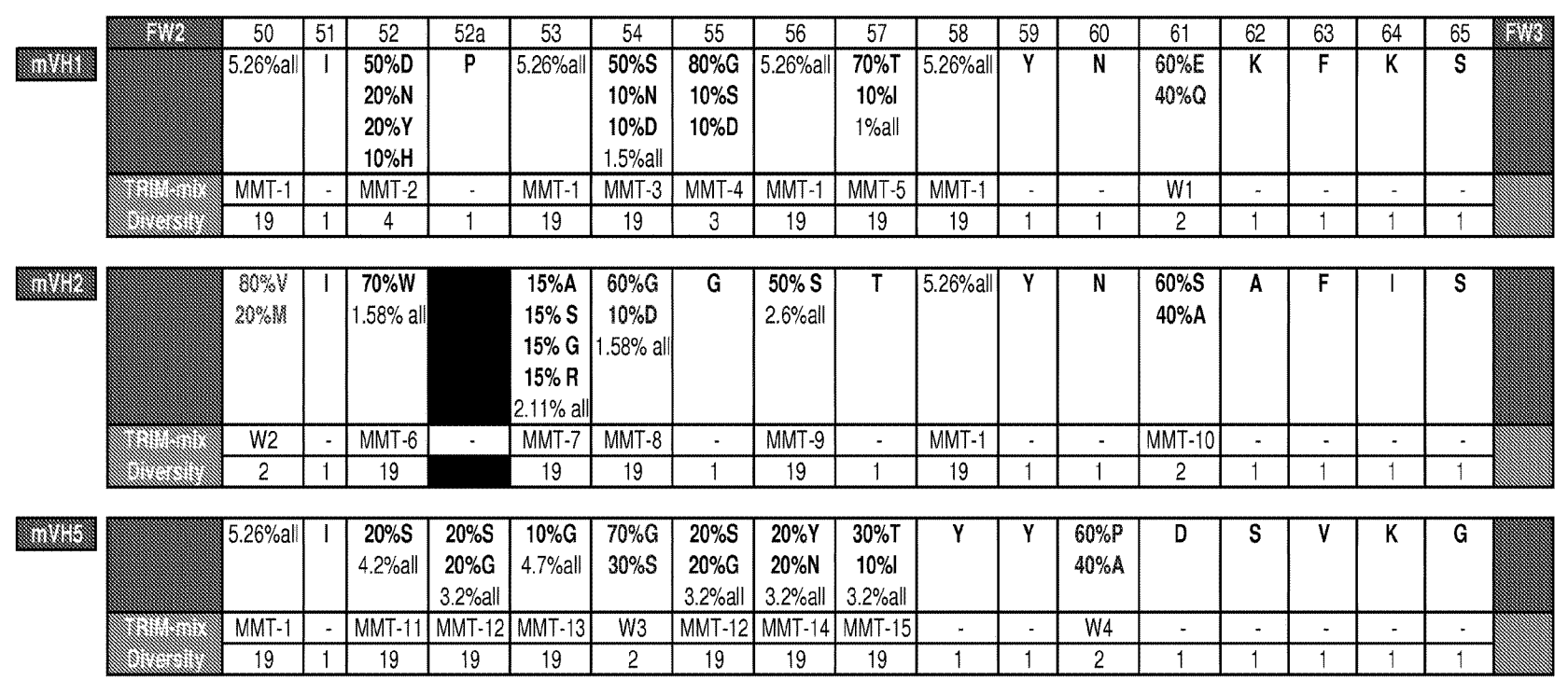

In certain aspects the present invention provides a synthetic murine antibody library which comprises a H-CDR2 design as shown in FIG. 10 or FIG. 11. In certain aspects the present invention provides a synthetic murine antibody library which comprises a H-CDR2 design as shown in FIG. 11.

In certain aspects the present invention provides a synthetic murine antibody library in which the H-CDR2 region has a diversity of at least $1.0*10^5$. In other aspects the present invention provides a synthetic murine antibody library which the H-CDR2 region has a diversity of at least $1.0*10^6$, of at least $1.0*10^7$, of at least $1.0*10^8$, of at least $1.0*10^9$ or of at least $1.0*10^{10}$.

In certain aspects the present invention provides a synthetic murine antibody library with a VH1 germline gene which comprises a diversity of at least $1.0*10^5$ in the H-CDR2 region. In other aspects the present invention provides a synthetic murine antibody library with a VH1 germline which comprises a diversity of at least $1.0*10^6$, of at least $1.0*10^7$, of at least $1.0*10^8$ or of at least $1.0*10^9$ in the H-CDR2 region.

In certain aspects the present invention provides a synthetic murine antibody library with a VH2 germline gene which comprises a diversity of at least $1.0*10^3$ in the H-CDR2 region. In other aspects the present invention provides a synthetic murine antibody library with a VH2 germline gene which comprises a diversity of at least $1.0*10^4$, of at least $1.0*10^5$, of at least $1.0*10^6$ or of about $1.0*10^7$ in the H-CDR2 region.

In certain aspects the present invention provides a synthetic murine antibody library with a VH5 germline gene which comprises a diversity of at least $1.0*10^5$ in the H-CDR2 region. In other aspects the present invention provides a synthetic murine antibody library with a VH5 germline which comprises a diversity of at least $1.0*10^6$, of at least $1.0*10^7$, of at least $1.0*10^8$ or of at least $1.0*10^9$ in the H-CDR2 region.

In certain aspects the present invention provides a synthetic murine antibody library wherein essentially all VH-VL combinations are efficiently displayed. In other aspects the present invention provides a synthetic murine antibody library wherein all or substantially all VH-VL combinations, with the exception of all VLB7-combinations are efficiently displayed. In yet other aspects the present invention provides a synthetic murine antibody library comprising at least two, at least three, at least four or at least five VH germline genes and at least two, at least three, at least four or at least five VL germline genes, wherein each of the VH-VL combinations comprised in said library is efficiently displayed. Efficiency of display can be measured by sandwich phage ELISA as described in the present invention.

In certain aspects the present invention provides a synthetic murine antibody library wherein essentially all VH-VL combinations are well expressed in *E. coli* in Fab format. In other aspects the present invention provides a synthetic murine antibody library wherein all or substantially all VH-VL combinations, with the exception of all VLB7-combinations are well expressed in *E. coli* in Fab format. In yet other aspects the present invention provides a synthetic murine antibody library comprising at least two, at least three, at least four or at least five VH germline genes and at least two, at least three, at least four or at least five VL germline genes, wherein each of the VH-VL combinations comprised in said library is well expressed in *E. coli* in Fab format. Expression in Fab format in *E. coli* can be quantified. In certain aspects the present invention provides a synthetic murine antibody library wherein essentially all VH-VL combinations are expressed at levels of more than 5 mg/L in a bacterial culture. In certain aspects the present invention provides a synthetic murine antibody library wherein essentially all VH-VL combinations are expressed at levels of more than 10 mg/L in a bacterial culture. In certain aspects the present invention provides a synthetic murine antibody library wherein most VH-VL combinations are expressed at levels of more than 15 mg/L in a bacterial culture. In certain aspects the present invention provides a synthetic murine antibody library wherein at least two, at least three, at least four or at least five VH-VL combinations are expressed at levels of more than 20 mg/L in a bacterial culture.

In certain aspects the present invention provides a synthetic murine antibody library wherein essentially all VH-VL combinations are well expressed in a mammalian system in IgG format. In other aspects the present invention provides a synthetic murine antibody library wherein all or substantially all VH-VL combinations, with the exception of all VLB7-combinations are well expressed in a mammalian system in IgG format. In yet other aspects the present invention provides a synthetic murine antibody library comprising at least two, at least three, at least four or at least five VH germline genes and at least two, at least three, at least four or at least five VL germline genes, wherein each of the VH-VL combinations comprised in said library is well expressed in a mammalian system in IgG format. Expression in a mammalian system in IgG format can be quantified. In certain aspects said mammalian system is a mammalian suspension culture. In other aspects said mammalian system is a mammalian adherent cell culture. In certain aspects said IgG format is an IgG1 format. In other aspects said IgG format is an IgG2a format. In certain aspects said mammalian system comprises HKB11 cells. In other aspects said mammalian system comprises PERC.6 cells. In yet other aspects said mammalian system comprises CHO cells. In certain aspects the present invention provides a synthetic murine antibody library wherein essentially all VH-VL combinations are expressed at levels of more than 5 mg/L in a mammalian system in IgG format. In certain aspects the present invention provides a synthetic murine antibody library wherein essentially all VH-VL combinations are expressed at levels of more than 10 mg/L in a mammalian system in IgG format. In certain aspects the present invention provides a synthetic murine antibody library wherein most VH-VL combinations are expressed at levels of more than 15 mg/L in a mammalian system in IgG format. In certain aspects the present invention provides a synthetic murine antibody library wherein at least two, at least three, at least four or at least five VH-VL combinations are expressed at levels of more than 20 mg/L in a mammalian system in IgG format.

In certain aspects the present invention provides a synthetic murine antibody library wherein all or substantially all of the members of said library are stable in isoproanol at a concentration of 30%) (v/v). It is an assumption that all CDR derivatives of a stable framework will behave like the tested mastergenes.

In certain aspects the present invention provides a synthetic murine antibody library wherein all or substantially all VH-VL combinations are thermally stable. Thermal stability can be measured as described in the present application. In certain aspects the present invention provides a synthetic murine antibody library wherein essentially all VH-VL combinations have a $T_m$ of more than 62° C. In other aspects the present invention provides a synthetic murine antibody library wherein essentially all VH-VL combinations have a $T_m$ of more than 64° C. In yet other aspects the present invention provides a synthetic murine antibody library wherein essentially all VH-VL combinations have a $T_m$ of more than 66° C. In yet other aspects the present invention provides a synthetic murine antibody library wherein most VH-VL combinations have a $T_m$ of more than 68° C. In yet other aspects the present invention provides a synthetic murine antibody library wherein many VH-VL combinations have a $T_m$ of more than 70° C. In certain aspects the present invention provides a synthetic murine antibody library wherein all or substantially all VH1-combinations have a $T_m$ of more than 70° C. In other aspects the present invention provides a synthetic murine antibody library wherein all or substantially all VH1_RV-combinations have a $T_m$ of more than 70° C. In yet other aspects the present invention provides a synthetic murine antibody library wherein all VLB1-combinations have a $T_m$ of more than 68° C. In yet other aspects the present invention provides a synthetic murine antibody library wherein all VLB3-combinations have a $T_m$ of more than 68° C. In yet other aspects the present invention provides a synthetic murine antibody library wherein all VLB7-combinations have a $T_m$ of more than 68° C. In yet other aspects the present invention provides a synthetic murine antibody library wherein all VLC3-combinations have a $T_m$ of more than 68° C.

In certain aspects the present invention provides rodent antibodies which possess favourable biophysical properties. Such antibodies are devoid of short comings of antibodies derived from synthetic libraries which have not undergone in-vivo maturation. Such favourable and desired biophysical properties include higher stability, higher expression levels and a low tendency for aggregation.

In certain aspects the present invention provides an antibody isolated from a rodent library contemplated by the present invention. In certain aspects said antibody may be a modified or a variant antibody of an antibody isolated from a rodent library contemplated by the present invention. In other aspects said modified or variant antibody may be a humanized antibody.

Each compositions and attendant aspects, and each method and attendant aspects, which are described above can be combined with another in a manner consistent with the teachings contained herein. According to the embodiments of the inventions, all methods and the steps in each method can be applied in any order and repeated as many times in a manner consistent with the teachings contained herein.

The invention is further described by the following examples, which do not limit the invention in any manner. For example, certain design features described below may be unique to the "HuCAL MOUSE" or "HuCAL RAT" design and not required in an alternative rodent library contemplated by the present invention.

EXAMPLES

Example 1

Generation of a Murine Antibody Library (HuCAL Mouse)

Example 1.1

Selection of VL- and VH-Germline Sequences for Generation of the Murine Master Genes Public available data were analyzed for usage of murine VH germline families (see Kaushik et al., Res. Immunol. (1996) 147, 9-26). The following table summarizes the occurrence of the different VH germlines:

TABLE 1

| VH | % in Kabat DB (var. strains) | Name (Kaushik et al. (1996)) | % in Kaushik et al. (BALB/c) | % in Kaushik et al. (var. strains) |
|---|---|---|---|---|
| VH1 | 33 | J558 | 30 | 45 |
| VH2 | 24 | Q52 | 14 | 10 |
| VH3 | 24 | 30-60 | 8 | 17 |
| VH5 | 16 | 7183 | 11 | 11 |
| VH9 | 10 | VGAM | 9 | 10 |
| SUM | 87 | | 72 | 93 |

Our aim was to generate a library that comprises as many germline families as possible. A library containing one member of each of the listed germline-families as master-gene would include more than 85% of the mouse VH repertoire, and exactly this was the goal of our task.

Germline-families often comprise more than one germline gene. For the listed families the number of germline gene ranges from 7 (VH2) to 134 (VH1)—the exact number depends on the mouse strain. Since most animal studies focus on BALB/c– and C57BL-6 mouse strains, only germline genes favoured by these strains were considered as basis for master-genes of the murine library. See Table 2. A reasonable intersection of VH-germline genes of both mouse strains was found and used exclusively.

TABLE 2

| | # of germline-genes in family | |
|---|---|---|
| VH | (var. strains) | (BALB/c & C57BL-6) |
| VH1 | 134 | 35 |
| VH2 | 7 | 2 |
| VH3 | 5 | 4 |
| VH5 | 20 | 9 |
| VH9 | 8 | 7 |

Among the murine light chains, kappa light chains constitute the majority of all light chains, accounting to about 90% of serum immunoglobulins isolated from mice (Frank and Gutman, 1988, Mol Immunol 25, 953-960). Therefore only VL-kappa was considered in the murine library. Since BALB/c mice and C57BL-6 mice do not share the same VL-germline-usage, the development of VL-mastergenes for BALB/c and C57BL-6 was done separately. Table 3 shows the germline families that occur most frequently.

TABLE 3

| BALB/c | |
|---|---|
| VL-kappa-family | Usage in % |
| 1 | 40 |
| 3 | 33 |
| 7 | 12 |
| SUM | 85 |

| C57BL-6 | |
|---|---|
| VL-kappa-family | Usage in % |
| 3 | 49 |
| 8 | 19 |
| 19 | 17 |
| SUM | 85 |

We aimed to prepare a library that contains one member of each of the listed germline families. Such a library will include >85% of the VL-sequences of BALB/c and C57BL-6 mice. Although germline family kappa-3 is used by both strains, two separate master genes are required, because different germline-genes, with in total 5 nucleotide differences, are preferred. Thus, in total 6 VL-mastergenes are required. Certain alterations of these germline genes are required to form master genes which maintain the modularity of the library.

Example 1.2

Selection of Master Genes

Two approaches were taken for the selection of the most frequently used germline genes, which are to be used as master genes:

a) Identification of the most prominent germline gene within the respective germline families b) Identification of the germline gene, which is most akin to the consensus of all germline-genes within one family.

Ideally, both approaches would result in the same germline-gene.

Example 1.2.1

Identification of the Most Prominent Germline-Gene within the Respective Germline-Families The germline gene used most abundantly was identified by comparison of the germline genes to re-arranged sequences. About 9,400 re-arranged murine VH and 2,500 Vk-sequences were extracted from a database flatfile, which was downloaded on from IgBLAST on the NCBI-Server, www.ncbi.nlm.nih.gov/igblast/. Sequence-fragments and sequences of bad quality were excluded. The remaining sequences were classified into germline families by application of filters for unique, germline specific amino acid pattern. This raw version of family-sorting was corrected by scoring the re-arranged antibodies against germline genes. Here the position-dependent amino-acid usage of each re-arranged sequence was compared to the amino-acid usage of each germline gene of various strains. By doing so, each re-arranged sequence got assigned to a nearest germline gene. If wrong assigned re-arranged sequences were identified, they were sorted to the correct germline family, leading to distribution shown in Table 4 (VH) and 5 (VL).

TABLE 4

| VH: | | |
|---|---|---|
| Germline-family | # re-arranged sequences | % distribution |
| VH1 | 5980 | 70.9 |
| VH2 | 597 | 7.1 |
| VH3 | 246 | 2.9 |
| VH5 | 762 | 9.0 |
| VH9 | 117 | 1.4 |
| others | 730 | 8.7 |
| SUM | 8432 | 100 |

TABLE 5

| | VL: | |
|---|---|---|
| Germline-family | # re-arranged sequences | % distribution |
| Vk1 | 543 | 21.6 |
| Vk3 | 232 | 9.2 |
| Vk7 | 14 | 0.6 |
| Vk8 | 187 | 7.4 |
| Vk19 | 44 | 1.8 |
| others | 1494 | 59.4 |
| SUM | 2514 | 100 |

The position-dependent amino-acid usage of the re-arranged sequence was compared with the amino-acid usage of the BLAB/c and C57BL-6-specific-germline-genes to identify the most frequent used germline genes. Each re-arranged sequence got assigned a nearest BLAB/c/C57BL-6-germline gene. If two or more germline genes were identified as nearest germline gene for a re-arranged sequence, all germline-genes were considered as nearest germline genes. For calculation of the preferably used germline-gene within a family the usage of each germline-gene was summed up. The results for the preferred germline genes within a family were surprisingly unambiguous and clear. Table 6 shows an example of the results for the usage of the four germline genes within the VH3-family:

TABLE 6

| germline-gene | absolute usage | relative usage [%] |
|---|---|---|
| D13203\|IGHV3-3*03\|BALB/c | 0 | 0.0 |
| AC073589\|IGHV3-3*01\|C57BL/6 | 5 | 1.9 |
| AJ223544\|IGHV3-6*03\|BALB/c | 14 | 5.4 |
| AC073590\|IGHV3-6*01\|C57BL/6 | 242 | 92.7 |
| SUM | 261 | 100 |
| # re-arranged sequences | 246 | |

For the example shown the sum of the absolute usage of germline-genes (261) differs from the number of re-arranged sequences (246), because 15 of the re-arranged sequences had been assigned to two or more germline-genes.

Table 7 shows the germline genes that are the most prominent in the different VH-families. Table 8 shows the most prominent germline genes for the different VL-families. Different germline-genes were identified for Vk3 of BALB/c and C56BL-6 as most prominent ones.

TABLE 7

| Germline-family | Name of prominent germline-gene | # re-arranged sequences | % of prominent germline-gene in-arranged sequences |
|---|---|---|---|
| VH1 | AC163348\|IGHV1-72*01 | 5980 | 49.7 |
| VH2 | AC090887\|IGHV2-2*01 | 597 | 87.0 |
| VH3 | AC073590\|IGHV3-6*01 | 246 | 92.7 |
| VH5 | AF120472\|IGHV5-9*04 | 762 | 49.8 |
| VH9 | AC073563_\|IGHV9-3*01 | 117 | 63.1 |

TABLE 8

| Germline-family | strain | Name of prominent germline-gene | # re-arranged sequences | % of prominent germline-gene in-arranged sequences |
|---|---|---|---|---|
| Vk1 | BALB/c | IGKV1-117*01 | 543 | 90% |
| Vk3 | BALB/c | IGKV3-12*01 | 232 | 24% |
| Vk3 | C57BL-6 | IGHV3-4*01 | 232 | 75% |
| Vk7*) | BALB/c | IGHV7-33*01 | 246 | 100% |
| Vk8 | C57BL-6 | IGHV8*21*01 | 187 | 37% |
| Vk19*) | C57BL-6 | IGHV19-93*01 | 44 | 100% |
| SUM | | | 1484 | |

*)Germline-family has one master-gene only

Example 1.2.2

Identification of the Germline-Gene, which is Most Akin to the Consensus of all Germline-Genes within One Family Consensus sequences of the germline-genes of the BALB/c C57BL-6-germline intersection were prepared. The comparison of the consensus sequences to the germline genes was done analogously as described herein above: the position-dependent amino-acid usage of the consensus sequences was compared to the amino-acid usage of the BLAB/c and C57BL-6-specific-germline-genes. By doing so, the consensus sequences got assigned a nearest BLAB/c and C57BL-6-germline gene. The result is shown in Table 9.

TABLE 9

| Germ-line-family | Name of prominent germline-gene | Germ-line-family | strain | Name of prominent germline-gene |
|---|---|---|---|---|
| VH1 | AC163348\|IGHV1-72*01 | Vk1 | BALB/c | IGKV1-117*01 |
| VH2 | AC090887\|IGHV2-2*01 | Vk3 | BALB/c | IGKV3-12*01 |
| VH3 | AC073590\|IGHV3-6*01 | Vk3 | C57BL-6 | IGHV3-4*01 |
| VH5 | AF120472\|IGHV5-9*04 | Vk7 | BALB/c | IGHV7-33*01 |
| VH9 | AC073563_\|IGHV9-3*01 | Vk8 | C57BL-6 | IGHV8*28*01 |
| | | Vk19 | C57BL-6 | IGHV19-93*01 |

The validity of this approach was confirmed by BLAST analyses of the consensus-sequences against all germline genes. Except for Vk8, the identification of the most prominent germline gene within the respective germline families, and the germline gene within the highest similarity to the consensus or BLAST search, came up with the same set of germline genes. For Vk8 IGKV8-28*01 was chosen as master gene, since is shows less deviations to the consensus-sequence than IGKV8-21*01. The usage of IGKV8-28*01 for rearranged sequences in germline-family Vk8 is 11%.

For mVH1 a second variant was included with K77R and T78V mutations, because the formation of a stabilising salt bridge between R77 and D100 might add extra high stability to this VH1-variant (Kaufmann et al., J. Mol. Biol, (2002) 318, 135-47). See FIG. 1.

The mastergenes eventually selected (see herein below) required slight modifications in order to achieve modularity of the library. The modifications made to generate restriction are summarized in Tables 10 (VH) and 11 (VL).

TABLE 10

| MG | Name of nearest germline-gene | Deviations to nearest germline-gene |
|---|---|---|
| mVH1 | AC163348\|IGHV1-72*01 | Q1E |
| mVH1_RV | AC163348\|IGHV1-72*01 | Q1E, K77R, A78V (stabilizing salt bridge) |
| mVH2 | AC090887\|IGHV2-2*01 | Q1E |
| mVH3 | AC073590\|IGHV3-6*01 | D1E, T26S (BspEI-site) |
| mVH5 | AF120472\|IGHV5-9*04 | K3Q (MfeI-site) |
| mVH9 | AC073563_\|IGHV9-3*01 | Q1E, I2V, K53E (XhoI-site) |

TABLE 11

| MG | strain | Name of nearest germline-gene | Deviations to nearest germline-gene |
|---|---|---|---|
| Vk1 = B1 | BALB/c | IGKV1-117*01 | V2I (EcoRV-site) |
| Vk3 = B3 | BALB/c | IGKV3-12*01 | — |
| Vk7 = B7 | BALB/c | IGHV7-33*01 | — |
| Vk3 = C3 | C57BL-6 | IGHV3-4*01 | — |
| Vk8 = C8 | C57BL-6 | IGHV8*28*01 | — |
| Vk19 = C19 | C57BL-6 | IGHV19-93*01 | — |

Also, to create full-length master genes from the germline genes, antibody framework 4 had to be added to the sequences. IMGT, imgt.cines.fr, provides access to murine J-regions, which form antibody framework 4 in antibody-development. FIG. 2 shows the framework regions for the heavy chains, FIG. 3 for the light chains.

J-region JH2 was selected for the VH-mastergene, since the associated 3' end of HCDR3 (FDY) is preferred in HCDR3 and JH2 provides al required RE-sites (StyI and BlpI). J-regions JK1 (=JK2 in FW4-sequence) was selected for complementation of the VL-mastergene, covering 85% of the mouse JK-usage. The last amino acid of framework 4 was changed from Ala to Thr to provide a BsiWI-site.

Example 1.3

Design of Murine CDRs

The sites of the closest contact between antibody and antigen are the complementary determining regions (CDR) of the antibody. H-CDR3 and L-CDR3 are playing major roles in antigen-binding, thus variability was mainly introduced into these two CDRs. Additional limited variability was introduced at antigen-contact-positions of the H-CDR2. Germline sequences were used for all other CDRs. For improvement of affinities of selected murine binders to obtain affinities comparable to the human lead candidate additional maturation cassettes were synthesized for H-CDR2.

Cysteine residues were generally avoided in the design of the CDRs because cysteine residues can be engaged in the formation of disulfide bonds covalently linking a binder with the panning target or in formation of antibody homodimers. Such binders are unlikely to be target-selective.

Re-arranged antibody-sequences were compiled and analysed for design of murine CDRs (see Example 1.1). Tables 4 (VH) and 5 (VL) show the data-sets used.

Example 1.3.1

Design of H-CDR3

The statistical analysis of the H-CDR3 was done for all re-arranged sequences irrespective of the germline family, since this CDR is encoded germline-independent by the D- and J-segment.

Although tyrosine, glycine and serine predominate in both, human and mouse H-CDR3 sequences, amino acid utilization differs among sequences of the same length between mouse and human variable heavy chains. These differences in overall amino acid frequencies and in the local distribution of amino acid residues within the H-CDR3-loops contribute to dramatic differences in the diversity and predicted structures of the H-CDR3 repertoires of mouse and human. (Zemlin et al., 2003, *J Mol Biol* 334, 733-749). Based on the analysis of mouse rearranged sequences some positions were identified, which deviated extremely from the composition of human H-CDR3 design. Especially Kabat position 95, 96 and 102 showed another amino acid usage than the human H-CDR3 (see Table 12). Specially designed murine H-CDR3s are therefore required.

TABLE 12

| Mouse | | | Human | | |
|---|---|---|---|---|---|
| 95 | 96 | 102 | 95 | 96 | 102 |
| 17% Y | 22% Y | 77% Y | 20% D | 10% G | 45% Y |
| 16% G | 17% G | 14% V | 20% G | 10% R | 15% I |
| 12% S | 10% D | | 8% V | 10% S | 15% V |
| 10% D | 7% R | | 8% E | 10% L | 10% P |
| 10% R | 6% L | | 8% A | 10% P | |
| 5% E | 6% S | | 8% S | | |
| | 5% N | | | | |

Illustration reduced to amino acids with an appearance of ≥5%.

In comparison to human antibodies, the length-range of H-CDR3 found in murine antibodies is restricted. While human H-CDR3 covers lengths from 2 to 28 amino acids, murine H-CDR3 uses only a set of 3 to 16 amino acids, as was found in analysis of data from Ig-BLAST. For results see Table 13. Similar results were described by Zemlin et al. (Zemlin et al., 2003, *J Mol Biol* 334, 733-749). TRIM® technology (see WO 93/21203) was used to design mouse H-CDR3s covering a length of 7-12 amino acids. This range covers about 80% of all murine H-CDR3s.

| HCDR3 length (HuCAL-numbering) | # of sequences | % |
|---|---|---|
| 1_aa | 0 | 0 |
| 2_aa | 1 | 0 |
| 3_aa | 72 | 1 |
| 4_aa | 113 | 1 |
| 5_aa | 326 | 4 |
| 6_aa | 341 | 4 |
| 7_aa | 446 | 6 |
| 8_aa | 645 | 8 |
| 9_aa | 1705 | 21 |
| 10_aa | 1311 | 17 |
| 11_aa | 1054 | 13 |
| 12_aa | 1189 | 15 |
| 13_aa | 355 | 4 |
| 14_aa | 187 | 2 |
| 15_aa | 120 | 2 |
| 16_aa | 46 | 1 |
| 17_aa | 19 | 0 |
| 18_aa | 9 | 0 |
| 19_aa | 2 | 0 |
| 20_aa | 0 | 0 |
| 21_aa | 0 | 0 |
| total # of sequences | 7941 | 100 |

The position-dependent relative amino acid distribution was determined for every single length, resulting in the natural amino acid distribution. The single amino acid distributions were aligned by grouping for the D-segment, leading to a right-centred alignment. Results are shown in FIG. 4. To summarize all lengths in one design, the weighted average of the amino acids was calculated for each position. See FIG. 5.

This calculated amino acid distribution was slightly modified to finalize the design of the H-CDR3 in the library:
Unification of the amino acids distribution to limit the set of different TRIM-mixes
Realization of amino acids with an appearance of >=10%
Supplementation of other amino acids (except cysteine) by 19 amino acid-mix, which was added to each position
Complete avoidance of cysteine
Examination for and reduction of certain restriction sites to achieve modularity
Lower usage of tryptophan, which is to be used only in the 19aa-mix
Avoidance of similar amino acids at one position (e.g. Glu OR Asp)
Avoidance of glycosylation-sites (NxS, NxT)

After considering and implementing the required modifications the H-CDR3 design shown in FIG. 6 was used.

The diversity of the H-CDR3 of the length of 12 amino acids is the product of the diversities at the single positions and is about $2.5*10^{13}$. The overall diversity is the sum of the diversities of the distinct lengths, 7-12 amino acids, and is about $2.6*10^{13}$.

Example 1.3.2

Design of L-CDR3

The statistical analysis of the L-CDR3 was done for all re-arranged sequences irrespective of the germline family, since this CDR is partly encoded germline-independent by the J-segment. Based on analysis of mouse rearranged VL-sequences, it was found, that a L-CDR3-length of 8 amino acids occurs in about 85% of the sequences (see Table 14). Thus the length of the L-CDR3 in the library was set to a length of 8 amino acids.

TABLE 14

| Length | #sequences | % |
| --- | --- | --- |
| 7aa | 173 | 9.6 |
| 8aa | 1571 | 87.6 |
| 9aa | 50 | 2.8 |
| SUM | 1794 | 100.0 |

The position dependent amino acid distribution of the 1571 re-arranged V-kappa sequences with the length of 8 amino acids was calculated. Results are shown in FIG. 7.

Reason for the variability at framework position 100 is probably the usage of different JK-segments. This calculated amino acid distribution was slightly modified to finalize the design of the L-CDR3 in the library:
Unification of the amino acids distribution to limit the set of different TRIM-mixes
Realization of amino acids with an appearance of >=10%
Supplementation of other amino acids (except cysteine) by 19 amino acid-mix, which was added to each position
Complete avoidance of cysteine
Examination for and reduction of certain restriction sites to achieve modularity
Lower usage of tryptophan, which is to be used only in the 19 amino acid-mix (especially positions 91 and 96)
Avoidance of similar amino acids at one position (e.g. Glu OR Asp)
Avoidance of glycosylation-sites (NxS, NxT, present at ~5% in nat. a distribution)
Fix position 90 to 100% Q and position 95 to 100% P After considering and implementing the required modifications the L-CDR3 design shown in FIG. 8 was used.

The diversity of the L-CDR3 of the length of 8 amino acids is the product of the diversities at the single positions and is about $4.7*10^7$, which is equal to the overall diversity.

Example 1.3.3

Design of H-CDR2

It had been described that positions 52, 52a, 54, 56, 58 (Kabat-numbering) of H-CDR2 are most responsible for antigen-contact in H-CDR2 region. See www.bioc.uzh.ch/antibody/Structures/AgContact/index.html. Variation of these positions therefore should enable the selection of antibodies with antigen-tailored binding pocket comprising HCDR2.

Figure 9:
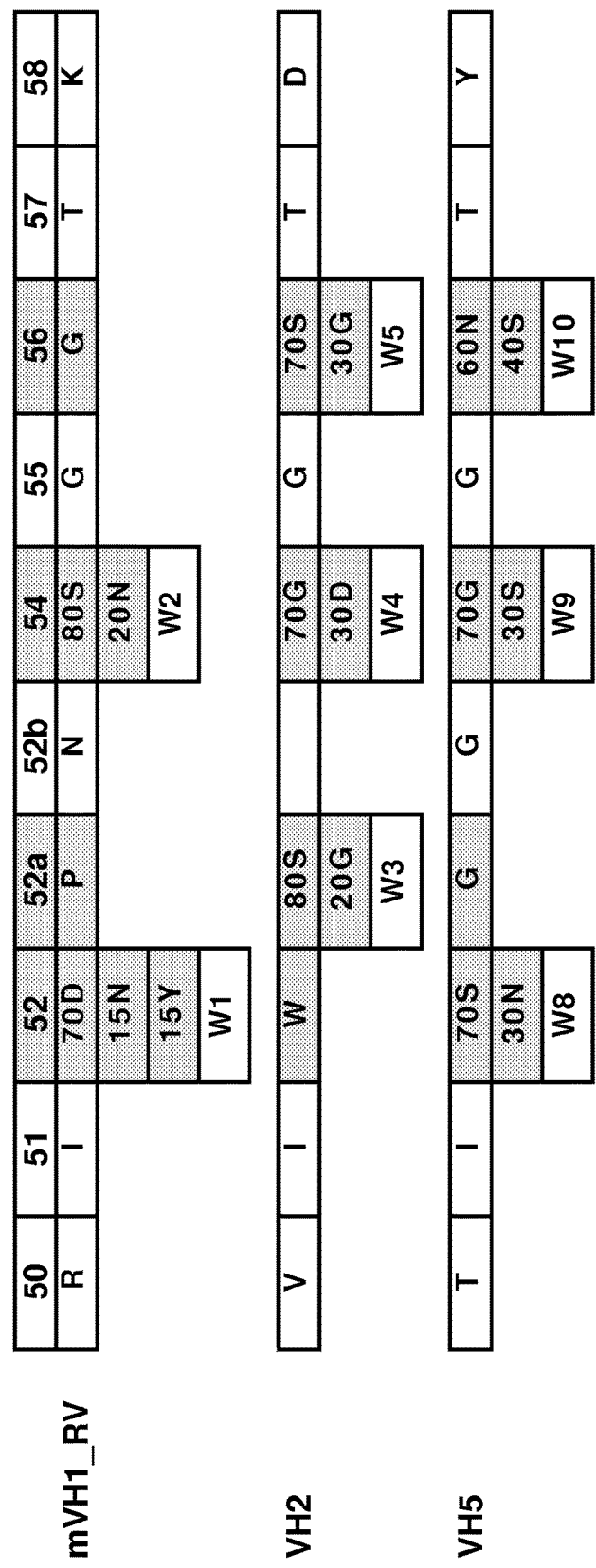
FIG. 9 shows the natural amino acid distribution of murine HCDR2 sequences for the three selected mVH mastergenes mVH1_RV (SEQ ID NO: 157) mVH2 (SEQ ID NO: 158) and mVH5 (SEQ ID NO: 159). In order to preserve prevalence of the germline sequences, the alternative residues present in the rearranged antibodies but not in the germline sequences were intentionally underrepresented in the design.

We investigated the amino acid distribution for distinct germ-line sequence families of rearranged antibodies represented by the three selected mVH master-genes (mVH1_RV, mVH2 and mVH5). A list of residues which were found frequently at particular positions of H-CDR2, was compiled. In order to preserve prevalence of the germline sequence, the alternative residues present in the rearranged antibodies but not in germ-line sequences were intentionally underrepresented in the design. The variation of the positions was introduced into the selected master-genes by wobbles. See FIG. 9.

H-CDR2 maturation cassettes were designed to improve the affinities of selected murine binders.

The position-dependent amino acid distribution of the H-CDR2 was investigated for distinct germ-line sequence families of rearranged antibodies represented by the three selected mVH master-genes (mVH1_RV, mVH2 and mVH5). Based on analysis of the rearranged mouse sequences, the amino acid distribution shown in FIG. 10 was deduced by calculation of the position-dependent amino acid distribution.

This calculated amino acid distribution was slightly modified to finalize the design of the H-CDR2 in the library:
Unification of the amino acids distribution to limit the set of different TRIM-mixes
Realization of amino acids with an appearance of >=10%
Supplementation of other amino acids (except cysteine) by 19 amino acid mix, which was added to some positions
Complete avoidance of cysteine
Avoidance of glycosylation-sites (NxS, NxT)
Examination for and reduction of certain restriction sites to achieve modularity
Enhance variability of VH2-HCDR2-cassette by addition of 19 amino acid mix at position 53 and 54.
Fix all position from position 62 onwards to an amino acid to provide a constant region for the PCR-backward-primer After considering and implementing the required modifications the H-CDR2 design shown in FIG. 11 was used.

The diversity of the H-CDR2-cassettes is the product of the diversities at the single positions and is about $1.1*10^9$ for mVH1-H-CDR2, $9.9*10^6$ for mVH2-H-CDR2 and $3.6*10^9$ for mVH5-H-CDR2.

Example 1.4

Cloning, Expression and Purification of the Murine Library

Bacterial Strains and Vectors Used for Cloning

Molecular cloning was carried out using the *E. coli* strains XL1-Blue (Stratagene) or Top10F+ (Invitrogen). Master genes were synthesized by GeneArt AG (Regensburg, Germany). The products from gene synthesis were cloned into a pGA-vector, and then re-cloned into tricistronic CysDisplay pMorph30-vector as described below. Phage display vector pMorph30 was derived from plasmid pMorph23 (Rothe et al., 2008, *J Mol Biol* 376, 1182-1200) basically as follows: hexa-His-tag (SEQ ID NO: 1) attached at the C-terminus of VH was replaced for the amino acid sequence HKHKHK (SEQ ID NO: 2), and a chi site in gIII was eliminated. Restriction endonucleases were from New England Biolabs or Fermentas, and T4 DNA ligase was from Invitrogen. Reaction conditions were carried out according to the manufacturer's recommendations.

Accession Numbers of Original Master-Genes

IMGT *Mus musculus* sub-database-/NCBI-accession numbers of germ-line sequences which were used for construction of the master-genes:
mVH1: IGHV1-72*01/AC163348, mVH2: IGHV2-2*01/AC090887, mVH3: IGHV3-6*01/AC073590, mVH5: IGHV5-9*04/AF120472, mVH9: IGHV9-3*01/AC073563, mVLB1: IGKV1-117*01/D00081, mVLB3: IGKV3-12*01/K02159, mVLB7: IGKV7-33*01/AF044198, mVLC3: IGKV3-4*01/Y15968, mVLC8: IGKV8-28*01/AJ235947, mVLC19: IGKV19-93*01/AJ235935, Jκ2: IGKJ2*01/V00777, Cκ:☐IGKC*01/V00807, JH2: IGHJ2*01/V00770, CH1+hinge: IGHG1*02/L35252

Considerations for the Synthesis of Master-Genes

Genes corresponding to the selected representative germ-line sequences were optimized on DNA level by applying following criteria: (i) rare codon usage has to be optimal for *E. coli* while human/murine rare codons were avoided whenever possible; (ii) undesirable DNA/RNA features such as internal TATA-boxes, chi-sites, ribosomal entry sites, AT-rich or GC-rich sequence stretches, sequences preventing mRNA-transport into cytoplasm (INS or CRS elements), repeat sequences, RNA secondary structures, and cryptic splice donor and acceptor sites were avoided; (iii) introduction of restriction endonuclease (RE) sites conflicting with the HuCAL® cloning-modularity were avoided; and (iv) restriction endonuclease sites required for the modular cloning were introduced. Glycosylation in variable domains is undesirable mainly because the carbohydrate-attachment is often found to affect binding of antigen due to steric hindrance, and is also responsible for heterogeneity of proteins expressed in eukaryotic hosts. Hence we ascertained that the designed VL/VH-master-genes did not encode for protein with potential sites for N-linked glycosylation.

Constant Domains in Fab Format

The constant domain of the kappa light chain is encoded by the Cκ gene (IGKC*01/V00807, see above). The N-terminal alanine residue was replaced by threonine which allowed the introduction of an BsiWI site at this position on the DNA level. A cysteine residue located in the C-terminus of wild-type Cκ was replaces by alanine.

The constant domain of the heavy chain in Fab format is encoded by CH1 gene-fragment. We have chosen gene IGHG1*02 because it represents consensus of CH1-sequences of the murine IgG1 type deposited in the IMGT database. The only mismatch was a Glu-residue in a germ-line sequence-fragment TWPSE (SEQ ID NO: 3), and therefore the Glu-residue was changed to a Gin. Addition of one alanine residue in front of the N-terminal sequence KTTPPS (SEQ ID NO: 4) allowed the introduction of a BlpI site. The first four residues of the hinge (sequence VPRD (SEQ ID NO: 5)) followed by residues Glu-Phe (necessary for the introduction of an EcoRI site) were added at the C-terminus of the CH1 domain.

Gene Assembly in Tricistronic Phage Display Plasmid pMorph31

The designed genes encoding for murine constant or variable domains were generated by PCR-assembly of a series of oligonucleotides, and cloned into a cloning pGA vector at GeneArt AG. It was convenient and faster to replace human VL, VH, Ck and CH1 genes for murine equivalents in two different interim vector molecules. Two derivatives of the pMorph30 plasmid (see above) denominated as "plasmid L" and "plasmid H", were constructed with large fragments of dummy DNA in order to facilitate cloning as follows: in "plasmid L", dummy DNA (about 3 kb) was inserted in place of light chain-coding region, whereas in "plasmid H", dummy DNA (about 2 kb) was inserted in place of heavy chain-coding region. Dummy DNA in "plasmid L" was then replaced for mCκ and mVL in two steps: mCκ gene (see above) was inserted by using BsiWI/SphI, and afterwards mVL kappa master-genes (see above) were inserted by using EcoRV/BsiWI. Dummy DNA in "plasmid H" was replaced for mCH1 and mVH also in two steps: mCH1 gene (see above) was inserted by using StyI (or Eco130I)/EcoRI, and then mVH master-genes (see above) were inserted by using MfeI/StyI. DNA fragments encoding master-genes mVH1, mVH1RV, mVH2, mVH5 or mVH9 (all linked to mCH1-region) were combined (cross-cloned) by using SphI/HindIII with master-genes mVLB1, mVLB3, mVLB7, mVLC3, mVLC8, and mVLC19 in pMorph30/mCκ plasmid resulting in 36 mVL-mVH combinations. After the cross-cloning, the display plasmid was denominated pMorph31 indicating the fact that the plasmid encodes besides of gpIII also murine variable and constant domains, and is hence suitable for display of murine Fabs.

Re-Cloning of VL-VH Master Gene Combinations into Bicistronic pMorphx9_Fab_FH Vector for Expression in *E. coli*

In order to analyze soluble expression of VL-VH framework combinations in Fab format, we have re-cloned by using XbaI and EcoRI all 36 mVL-mVH master-gene combinations (as Fab-encoding inserts) into pMorphx9_Fab_FH vector (Rauchenberger et al., 2003, *J, Biol. Chem.* 278, 38194-38205) where FH indicates that the Flag- and hexa-His-tags (SEQ ID NO: 1) were attached C-terminally to the Fab.

Conversion of VL-VH Master Gene Combinations to Murine IgG2a Format

In order to analyze expression of master-gene combinations in full-length murine IgG2a kappa format in mammalian cells, we have subcloned the 36 mVL-mVH master gene combinations into pMorph4_h/m_IgG vector which is a derivative of pMorph2_h_IgG vector (Steidl et al. 2008. *Mol Immunol* 46(1):135-44). In the pMorph4_h/m_IgG vector, the light and heavy chains were encoded in one plasmid; however, each chain was translated together with its N-terminal leader sequence from a separate transcript (transcription was driven by two CMV-promoter sites located in the plasmid).

Conversion of VL-VH Master Gene Combinations to Murine IgG1 Format

In order to analyze expression of master-gene combinations in full-length murine IgG1 kappa format in mammalian cells, we subcloned the 36 mVL-mVH master gene combinations into pMorph4_h/m_IgG vector, which is a derivative of pMorph2_h_IgG vector (Steidl et al. 2008. *Mol Immunol* 46(1):135-44). In the pMorph4_h/m_IgG vector, the light and heavy chains are encoded on one plasmid; however, each chain is translated together with its N-terminal leader sequence from a separate transcript (transcription was driven by two CMV-promoter sites located in the plasmid).

Expression and Purification of Fab

Expression in *E. coli* TG1-cells from the pMx9_Fab_FH plasmid was carried out in 500 ml of 2×YT-medium supplemented with chloramphenicol (34 µg/ml) and glucose (0.1%). After induction with IPTG (0.75 mM), the cells were grown at 30° C. for 20 h. Cell pellets were lysed during incubation with lysis buffer (25 mM Tris/HCl, pH 7.4, 0.5 M NaCl, 10 mM imidazol, 0.2% lysozyme, 2 mM $MgCl_2$, 20 U/ml benzonase and EDTA-free protease inhibitor cocktail from Roche) for 30 min at RT. Fab-purification from cleared cell lyzates (centrifugation and filtration, 0.2 µm) was carried out by 2-step purification using Äkta xpress for automated processing. First step was IMAC chromatography with $Ni^{2+}$ ions, where in case of stability evaluation an additional wash step with 30% isopropanol in PBS was carried out. After elution with high concentration of imidazol the eluted peak was reloaded on a gel filtration column, and proteins were separated by size exclusion using PBS pH 7.4. Finally, elution fractions which correspond to expected size were pooled.

Expression and Purification of IgG

Eukaryotic HKB11 (Cho et al.; J Biomed Science (2002) 9, 631-8) cells were transiently transfected with the pMorph4_h/m_IgG plasmid encoding the heavy and light chains. Cell culture supernatant was harvested from 3 to 7 days post transfection. After adjusting the pH of the supernatant to 8.0, addition of NaCl (2 M final concentration) and sterile filtration (0.45 µm), the solution was subjected to standard protein A affinity chromatography (MabSelect SURE, GE Healthcare). If not stated otherwise, buffer exchange was performed to 1× Dulbcecco's PBS (pH 7.2, Invitrogen) and samples were sterile filtered (0.2 µm). Purity of IgG was analysed under denaturing conditions by SDS-PAGE or by using Agilent BioAnalyzer and in native state by HP-SEC.

Phage Preparation

Phage amplification and purification was carried out essentially as described previously (Krebs et al., 2001, *J Immunol Methods* 254, 67-84) with a following modification. Phagemids (VL-VH framework combinations encoded in display plasmid) were propagated in *E. coli* Top10F+ cells in 2×YT/Cam/Tet/glucose (1%) medium. After helper phage infection (hyperphage from Progen, Cat. No.: PRHYPE, multiplicity of infection: 40), centrifugation and resuspension of the cell pellet in 2×YT/Cam/Kan/Tet/IPTG (0.25 mM), phages were produced during 20 h-incubation at 22° C.

Phage ELISA

Black Maxisorp microtiter plates (Nunc) were coated with anti-pIII antibody (MoBiTec, Cat. No.: PSKAN3) for determination of relative pIII-level (≈phage concentration), or with anti mouse F(ab')$_2$ antibody (Jackson ImmunoResearch Lab.; Cat. No.: 112-006-072) for determination of relative Fab-level in phage samples. Although the exact epitope of the anti mouse F(ab')$_2$ antibody is not known (it is presumed to be located in the constant domain), we reasoned that binding of the antibody to murine Fab is not likely to be strongly affected by sequence-variation in Fv-domain, and thus the antibody should be suitable for general assessment of murine Fab-display on tip of filamentous phage. TBS pH 7.4 containing Tween 20 (0.05%) and chemi-blocker (from Chemicon; diluted 1:2) was used for blocking of non-specific binding sites in the microtiter plate and on phages. After incubation with phages, wells were washed with TBS-T, and incubated sequentially with biotinylated anti-bacteriophage antibody (Sigma Cat. No. B2661) and avidin-HRP (BD Pharmingen; Cat. No.: 554058). "Quanta Blu" substrate for HRP was applied, and fluorescence signals were recorded on Tecan-Spectrafluor instrument (excitation: 320 nm, emission: 430 nm). The relative pIII- and Fab-levels in phage sample were determined by using reference phage (displaying a previously selected binder converted into Fab with murine constant domains) and the standard 2-state model applied for non-linear regression. The relative display rate was defined as a ratio of the Fab- and pIII-levels.

Example 1.5

Characterization of the Murine Antibody Library by Way of Exemplary Antibody 4D5

Good presentation on phages and high expression in cells can be achieved only for well folded and stable Fab-molecules. Thermodynamic stability of Fab-molecule depends on intrinsic stability of the individual domains (heavy and light chains) as well as on non-covalent interaction between the two domains (Ewert et al., 2003, *J Mol Biol* 325, 531-553). Tight interaction between Fd (heavy chain) and Cκ (light chain) are of particular importance because in the CysDisplay® system the two domains cannot be covalently linked via disulfide bond since cysteine residue in the C-termini of constant domains was eliminated. Therefore, instead of testing VL- and VH-frameworks individually, we analysed VL-VH combinations which could be efficiently folded and expressed in *E. coli* (Fab format) and in mammalian cells (IgG format).

As a test case we used the HCDR3 sequence of antibody 4D5 (WGGDGFYAMDY) (SEQ ID NO: 6). This sequence had already been used previously for the assessment of human master-genes prior the construction of the original HuCAL library (Knappik et al., 2000, *J Mol Biol* 296, 57-86)

Analysis of Display Efficiency

Figure 12:
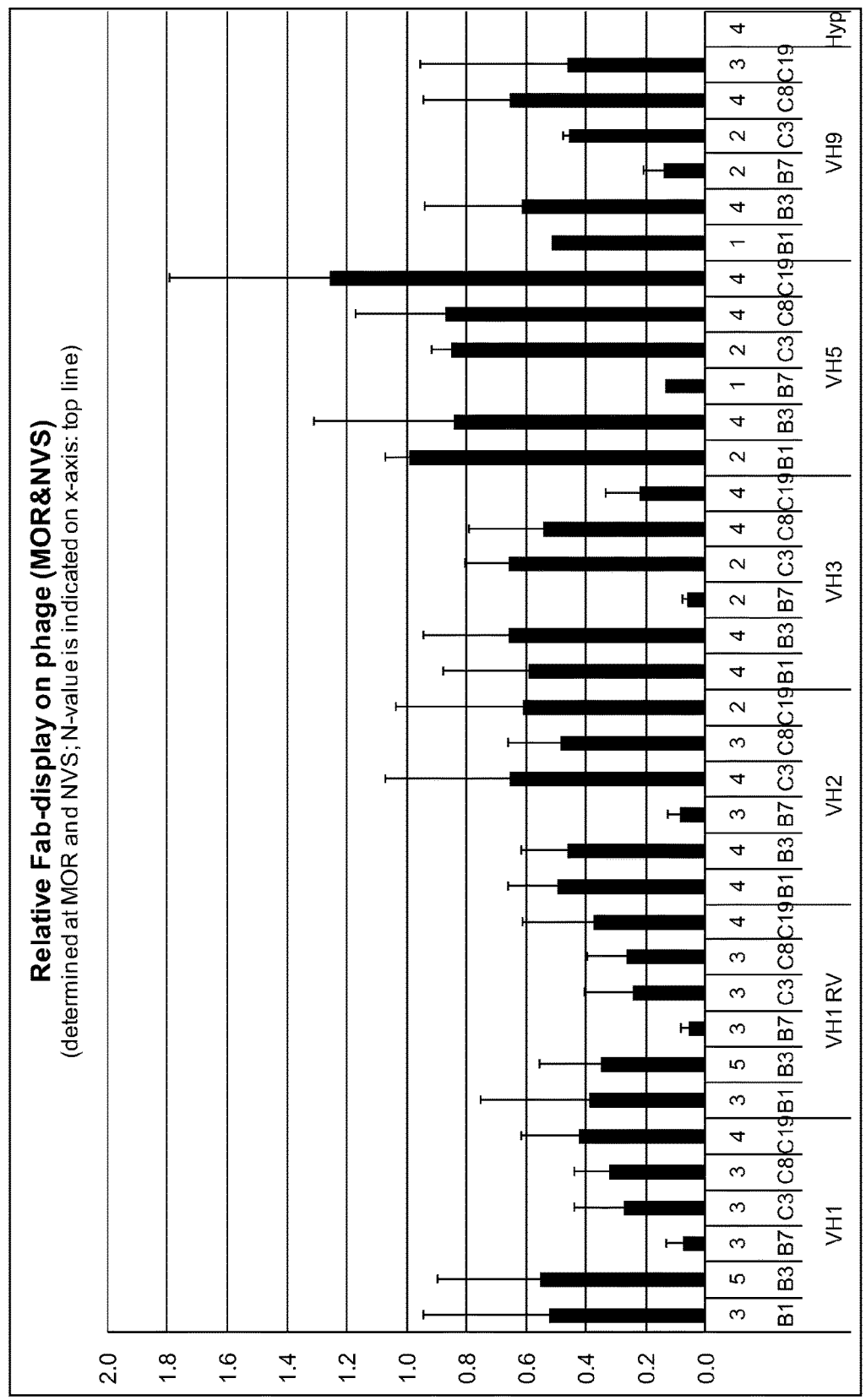
FIG. 12 depicts display of murine mastergenes in Fab-format on filamentous phage. Altogether 36 murine VL-VH combinations were tested and all combinations tested, with the exception of all mVL-B7 combinations, were well displayed on phages.

Efficient display of library members on phage particles is a prerequisite for successful phage display selections. We used sandwich phage ELISA for quantification of display of the 36 murine VL-VH combinations in Fab-format. Our data indicate that most of the tested mVL-mVH combinations, with the exception of all mVLB7-combinations, were displayed on phages. There was no significant difference in display between Fab-molecules containing mVH1- or mVH1_RV. Although statistically insignificant, there is a trend indicating that the VH5-combinations are slightly better displayed than all other murine Fabs Results are depicted in FIG. 12.

Soluble Fab Expression

Next, we investigated whether the favorable folding and expression characteristics of tested murine Fab in bacterial host can also be observed also in soluble format. In this format both heavy and light chains are directed into the periplasm of *E. coli* where they achieve their final fold and associate with each other to form a stable Fab-fragment.

Figure 13:
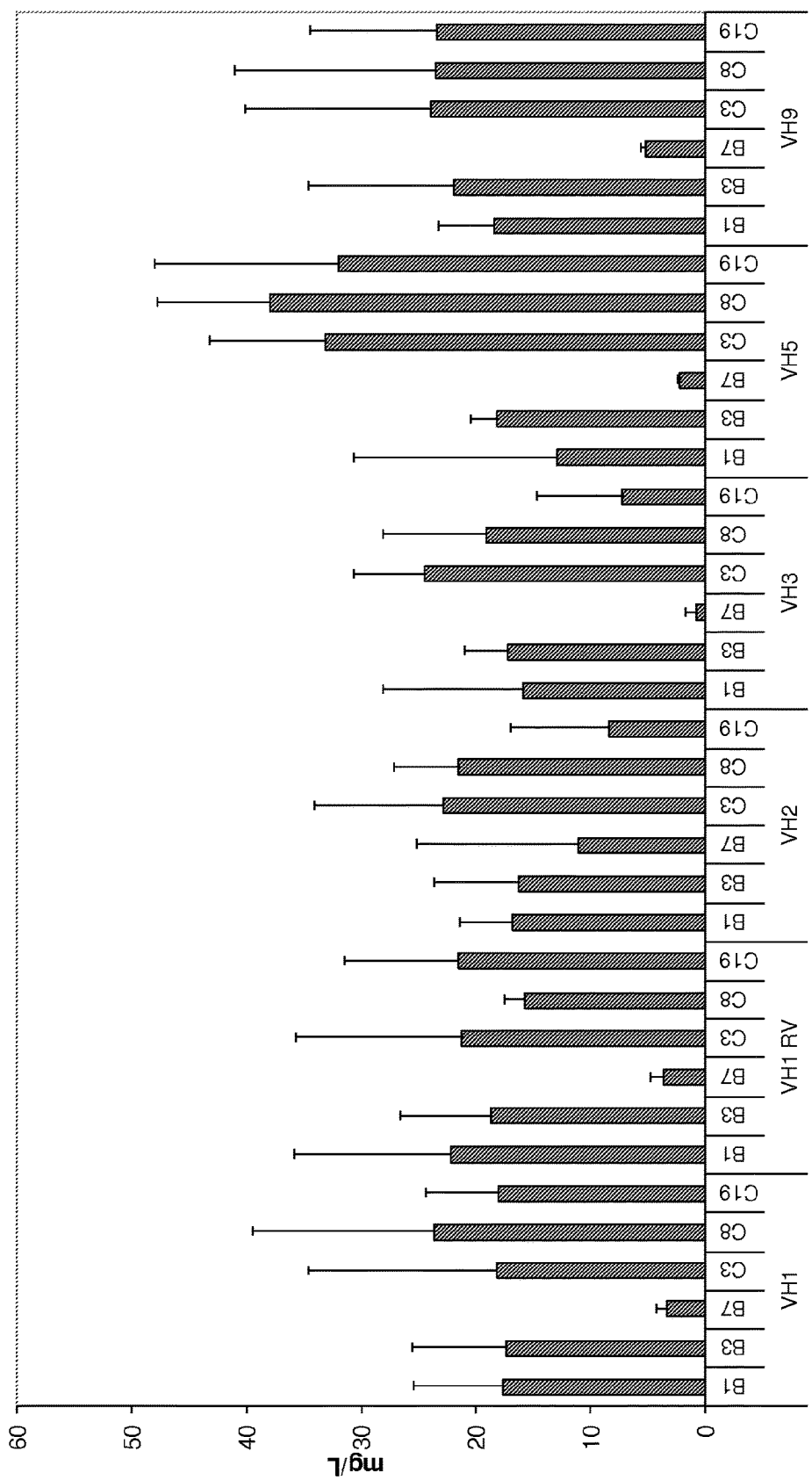
FIG. 13 depicts soluble expression of the murine mastergenes in Fab-format. All murine VL-VH combinations tested, with the exception of all mVL-B7 combinations, were well expressed in *E. coli*.
Figure 14:
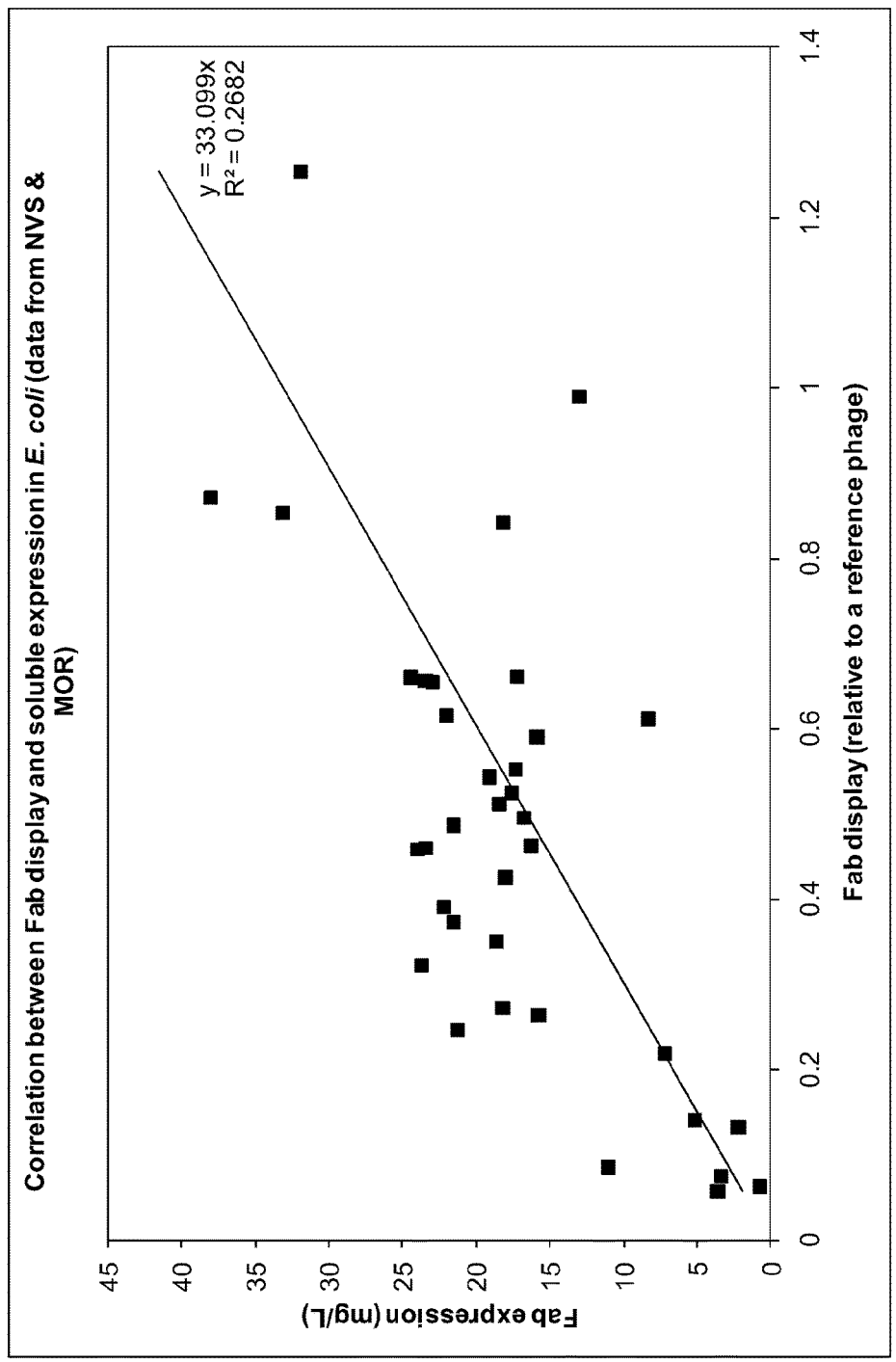
FIG. 14 shows that the soluble expression in *E. coli* and the display on filamentous phage correlates remarkably well.

As shown in FIG. 13 all tested murine VL-VH combinations, with the exception of all mVLB7-combinations, were well expressed in *E. coli* and the yield of purified Fab exceeded 5 mg/L bacterial culture. The VH5-combinations (particularly, VLC3-, VLC8-, VLC19-VH5) seem to be slightly better expressed than all other murine Fabs. There was no significant difference in expression between Fab-molecules containing mVH1- or mVH1_RV. Fab-expression in soluble- and in display-forms correlates remarkably well (see FIG. 14). Furthermore, characterization of isolated material revealed that 98-100% of purified Fab was at monomeric form. This indicates usefulness for the development of murine surrogate antibodies.

Soluble IgG-Expression

The vast majority of antibody-based therapeutic biologicals currently on the market are in IgG-format for a variety of reasons: (i) the half-life of IgG molecules in the human body is very high (about 3 weeks) due to the interaction of the IgG with the neonatal receptor (FcRn); (ii) IgG molecules are highly soluble, thermodynamically stable and relatively resistant to proteases in blood; and (iii) IgG possess ADCC (antibody-dependent cell-mediated cytotoxicity) and/or CDC (complement-dependent cytotoxicity) activity, which are required for elimination of tumor cells.

Since the expression of a particular VL/VH-combination in Fab-format not necessarily correlates with the expression of the same VL/VH-combination in IgG-format, we opted to characterize the expression of all mutual combinations of synthesized murine VL- and VH-mastergenes also in IgG format.

Two distinct mouse IgG formats, IgG1 and IgG2a, were chosen for the expression test. The murine IgG2a isotype was found in about 27% of all monoclonal IgG isolated from Balb/c mouse (Rousseaux and Bazin, 1979, *Vet Immunol Immunopathol.* 1, 61-78), and we tested all VL-VH mastergene combinations in this format. In addition, few selected VL/VH-combinations were tested also in murine IgG1 format which was found in about 40% of all monoclonal IgG isolated from Balb/c mouse (Rousseaux and Bazin, 1979, *Vet Immunol Immunopathol.* 1, 61-78).

Figure 15:
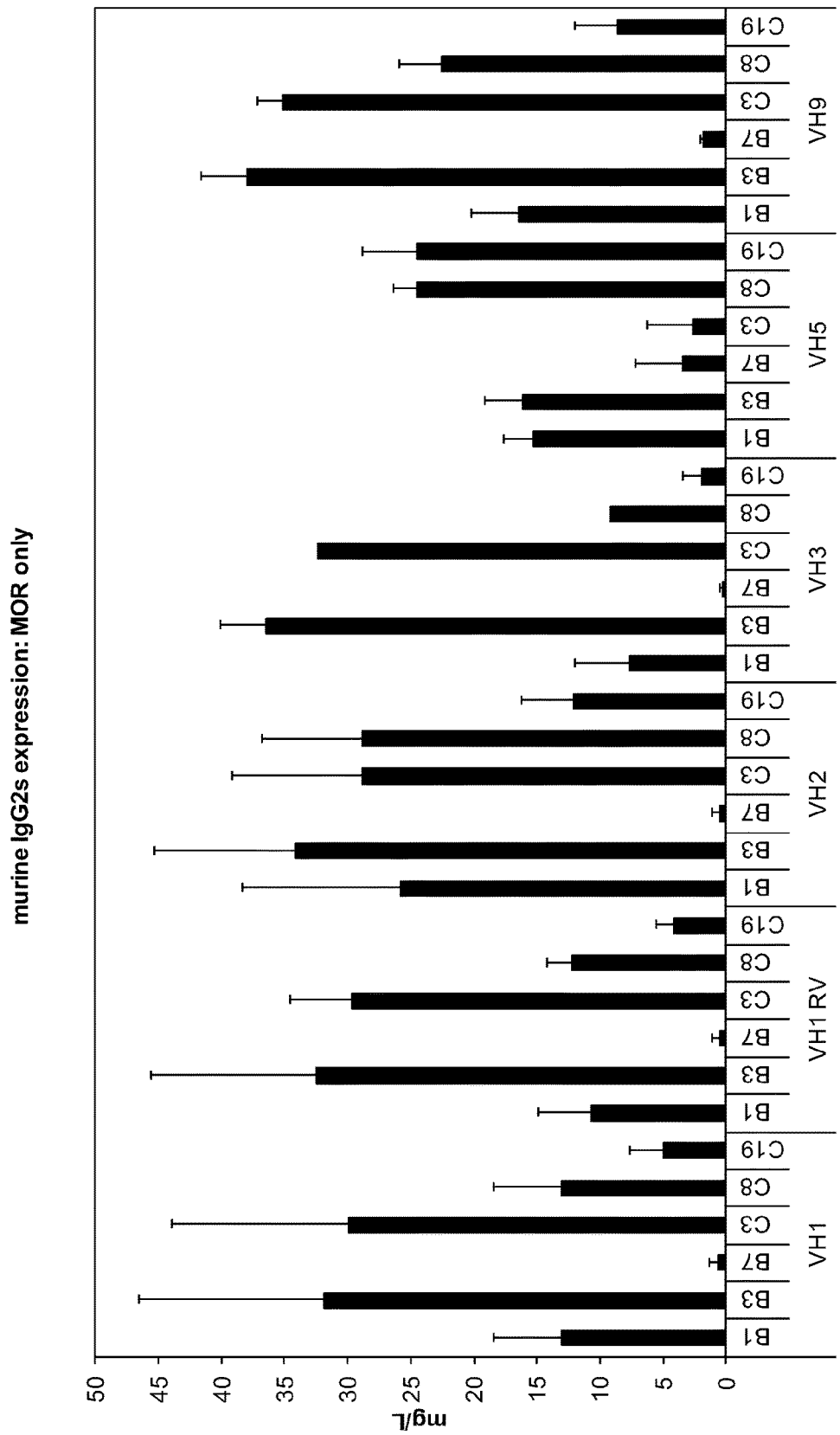
FIGS. 15 and 16 show the expression of murine IgGs (IgG1 and IgG2a). Essentially all combinations tested show expression levels of well above 10 mg/L.
Figure 16:
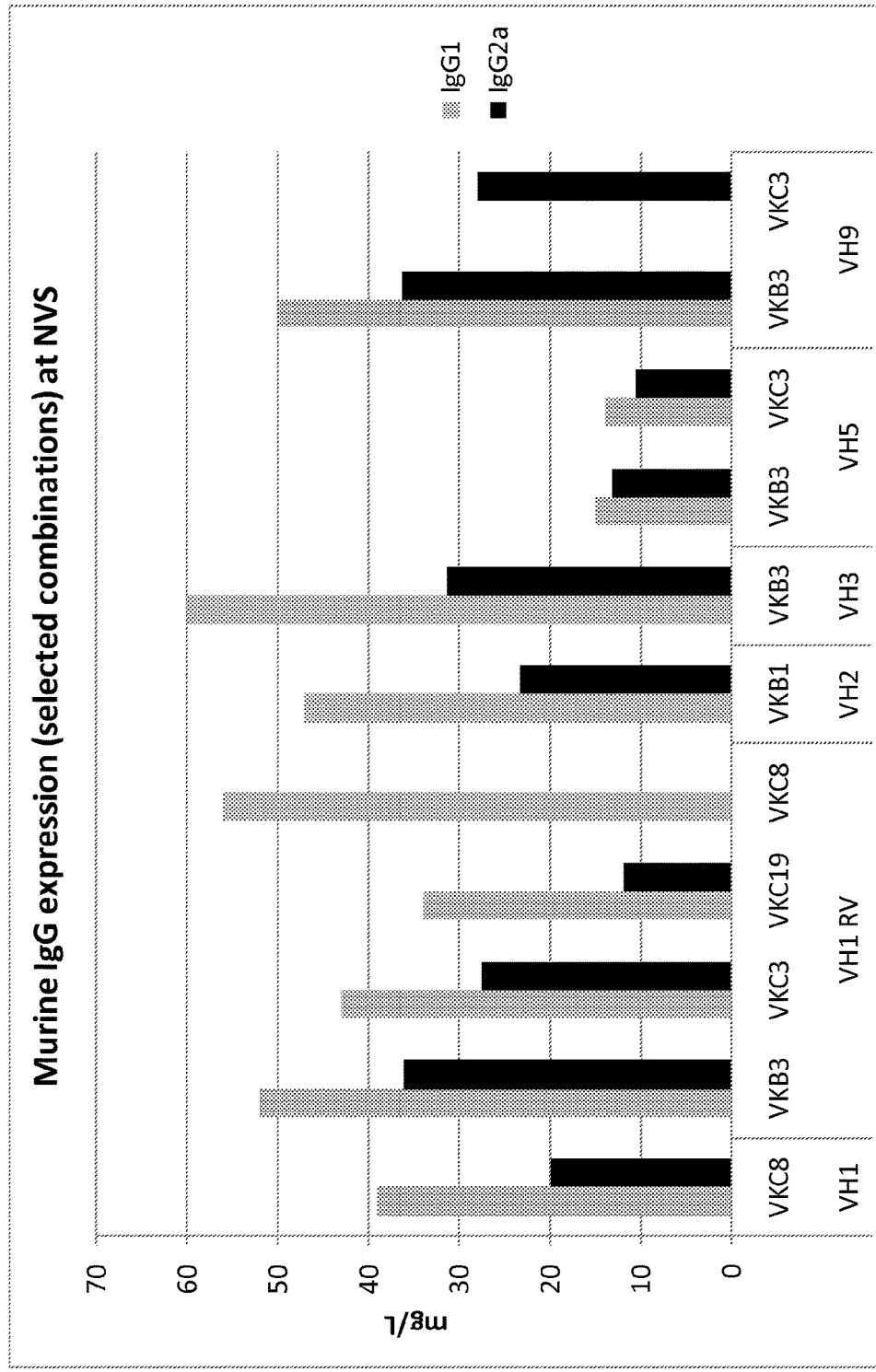

All murine VL- and VH-mastergenes were re-cloned into mammalian expression vectors, and the resulting plasmids were used for transient transfection of a mammalian suspension cell line as described herein above. Data are shown in FIGS. 15 and 16, which indicate that the expression level of almost all mVL-mVH combinations tested, in both murine IgG1 and IgG2a formats, largely exceed a value of 10 mg/L. Similar to the observations made for the Fab format, there was no difference in expression between IgG-molecules containing mVH1- or mVH1_RV. Very low expression level of mVLB7-combinations parallels the very low prokaryotic expression of the mVLB7-combinations observed in the Fab format. Altogether, against the odds, we were able to soluble express almost all of the mVL-mVH combinations tested.

All murine VL and VH-mastergene combinations were purified in a 2-step purification process using Äkta express. Expressed Fab-fragments are bound to chelated Ni2+ and washed either with 15 column volumes of 20 mM Na-Phosphatbuffer/500 mM NaCl, pH 7.4, 20 mM Imidazole or, in a separate purification, using 20 column volumes of 30% Isopropanol/20 mM Na-Phosphatbuffer pH 7.4. Second step of purification (SEC) was identical for both procedures (with or without isopropanol treatment) and is described herein above. After purification both protein preparations were compared regarding yield, concentration, purity, ratio of VH and VL and thermal stability. A wash step with 30% isopropanol while the Fab is still bound to the IMAC column was introduced in order to receive Fab fragments that are of higher purity. However for some Fab fragments this treatment was seen to be too harsh because the interface—the hydrophobic interaction between heavy and light chain—was not strong enough to endure this procedure. The heavy and light chains of such Fab fragments were eluted at different stages and therefore the ratio between the two chains did deviate from 1:1.

Thermal Stability

Protein expression level in cellular host depends on many parameters. Some of them are related to intrinsic protein folding; however, many are dependent on the metabolic status of the host, such as activity of translational and translocation machineries, or levels of secreted proteases and ubiquitin. These latter protein-extrinsic properties are difficult to control, and vary often substantially in experiments performed in different days. Due to the variations observed in the expression tests described above we characterized the intrinsic protein properties by using protein samples purified during the expression tests. Practically, measurement of thermal stability can be performed in a small volume in a standard thermo cycler for real-time PCR, and is therefore suitable for relative comparison of intrinsic stability among a large group of tested proteins. On the other hand, thermal denaturation of proteins, in contrary to chemical denaturation by chaotropic agents, is typically irreversible, and cannot be used directly for determination of absolute thermodynamical parameters, such as $\Delta G$ of the protein transition between its two conformational states.

Figure 18:
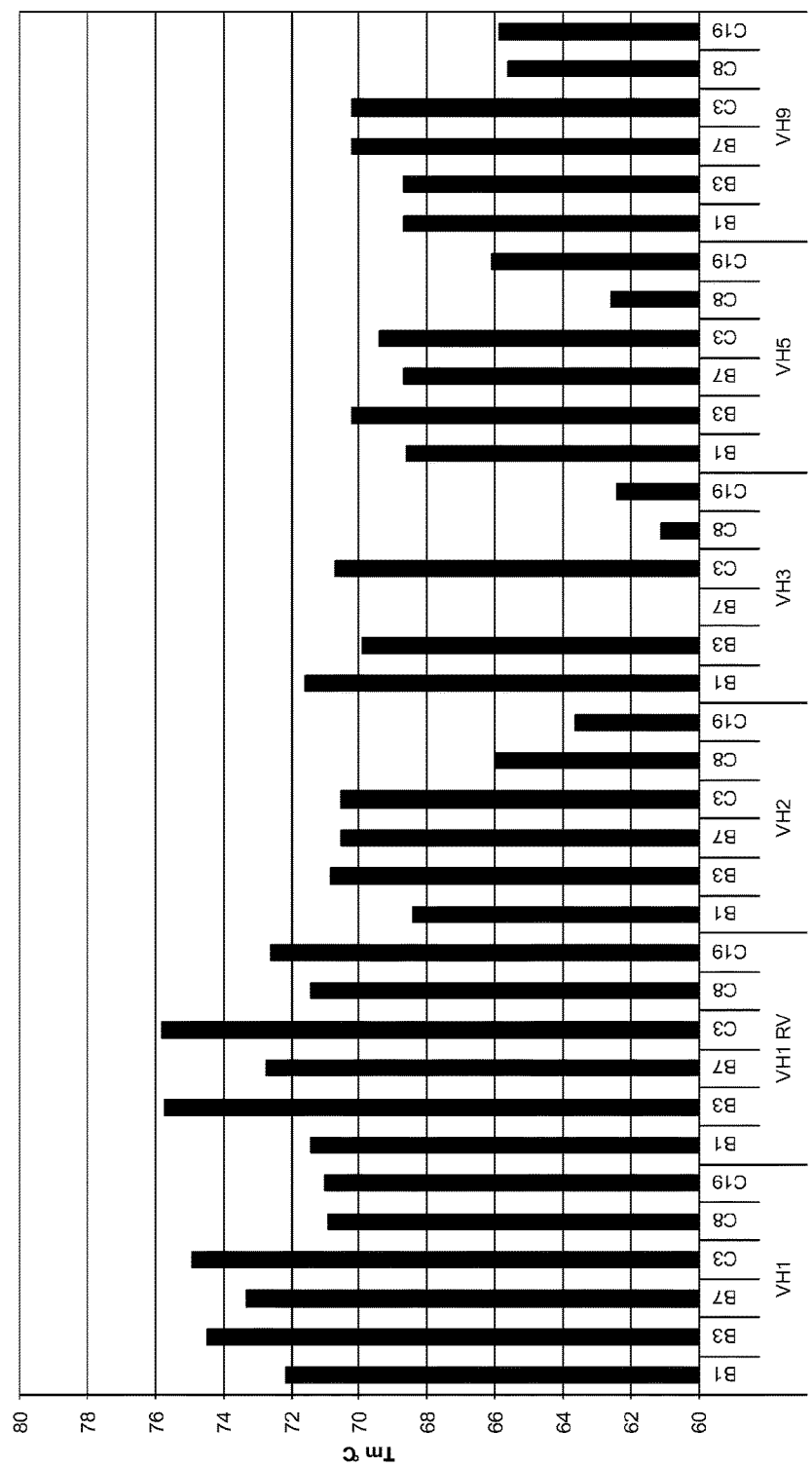
FIG. 18 illustrates thermal stability of murine mastergenes in Fab-format. The thermal stability of all tested murine VL-VH combinations, including the mVLB7 combinations, was reasonably high.

Results are shown in FIG. 18. The most thermally stable murine VL-VH combinations were are the combinations VLB3-VH1_RV and VLB3-VH1_RV. Of importance, even the thermal stability of the tested mVLB7-combinations was reasonably high. This was unexpected considering the comparably low expression levels detected for all mVLB7-combinations in Fab and IgG-formats.

Selection of Fv-Frameworks for Library Construction

During the assessment of the 36 different frameworks (combinations of 6 VL-with 6 VH master-genes) described above, we observed that basically all Fv-frameworks were expressed in Fab-format *E. coli* and in IgG-format in mammalian cells with appreciable yields exceeding usually 10 mg/L. The only exceptions were all mVLB7-combinations and several of the tested mVLC19-combinations (see above). In our selection of the most favorable Fv-frameworks we strongly emphasized thermodynamical stability of Fv-molecules. In this regard, the mVLB3-mVH1_RV and mVLC3-mVH1_RV with mid-point of thermal unfolding (Tm) at about 76° C. were clear choice (see FIG. 18). Furthermore, mVH1, mVLB3 and mVLC3 germ-line sequences are frequently found in the IMGT database (see Table 15). Two other selected Fv-frameworks comprised mVLB3 and mVLC3 in combination with mVH5. mVH5 is highly used in murine heavy chains (Table 15), mVH5-combinations were well expressed in Fab format in *E. coli* (see FIGS. 12 and 13), and mVLB3-mVH5 and mVLC3-mVH5 sequences were found in the Kabat database of re-arranged murine antibodies (Table 16).

Another favorable Fv-framework comprising distinct VH was mVLB1-mVH2 due to relatively high abundance of this Fv-framework combination in the Kabat database (Table 16), and due to high usage of mVLB1 in murine light chains (Table 15). Diversified LCDR3- and HCDR3-library cassettes were therefore subcloned into the selected Fv-frameworks resulting in five murine sublibraries (see below).

Table 15 indicates the usage of VK and VH germline families for the mouse strains BALB/c and C57BL-6.

TABLE 15

| BALB/c | | C57BL-6 | | BALB/c & C57BL-6 | |
|---|---|---|---|---|---|
| VK_B1 | 40% | VK_C3 | 49% | VH1 | 27% |
| VK_B3 | 33% | VK_C8 | 19% | VH2 | 10% |
| others | 27% | VK_C19 | 17% | VH5 | 25% |
| | | others | 5% | VH8 | 12% |
| | | | | others | 26% |

Table 16 shows the result of the statistical analysis of the combined VL-VH sequence representation in the Kabat database.

TABLE 16

| VL-VH Pair | Number of Hits in Kabat |
|---|---|
| Vk B3_VH5 | 3 |
| Vk B1_VH2 | 4 |
| Vk B3_VH9 | 0 |
| Vk B3_VH3 | 1 |
| Vk B3_VH1 RVT | 0 |
| Vk C3_VH9 | 0 |
| Vk C3_VH5 | 1 |
| Vk C8_VH1 | 0 |
| Vk C19_VH1 RVT | 0 |
| Vk C3_VH1 RVT | 0 |

Statistical Analysis of Combined VL-VH Sequence Representation in the Kabat Database To determine whether those VH-VL combinations that resulted in well expressing antibodies in the library of the present invention also exist in naturally selected antibodies, the representation of those antibodies was analysed in the Kabat database. The combined VH-VL framework sequences of the antibodies where blasted against all frameworks of the complete Kabat antibody sequences, comprising a sequence for both VH and VL.

In the Kabat database 1501 complete mouse antibody entries with complete sequence information (heavy and light chain) are present. To cover all possible heavy and light chain combinations of the BALB/c mouse strain, 101 (heavy chains)×23 (light chains)=2323 complete antibodies would be needed in the sample set. For C57BL6 the number would be even higher: 195 (heavy chains)×74 (light chains)=14430 complete antibodies. Taking into account the small sample set and the fact, that in the Kabat database these two mouse strains are not the only ones which are represented it is rather unlikely, that one of the VH-VL chain combinations of the mouse library of the present invention exists in this dataset. Any number of matches larger than one was therefore taken as an indication, that this combination might in fact be a naturally preferred one. The best represented chain combinations where chosen for final library design.

Example 1.6

Diversification of the Murine Library

Introduction of DNA-Stuffers for Insertion of Diversified CDR3-Cassettes into the Display Plasmid pMorph31

DNA regions encoding for L- or H-CDR3 are short (<40 bp). In our modular system, both original CDR3 encoded in the master-gene and diversified CDR3-cassette are flanked by a pair of unique restriction sites, which allow for the introduction of diversified CDR3-cassette in place of the original CDR3. Inefficient plasmid digest at these restriction sites can result in a substantial background comprising vector with original CDR3 because it is not technically feasible to efficiently separate by gel electrophoresis linearized plasmids (~5500 bp) in which CDR-encoding region is present or absent. In order to prevent the vector background regardless of the digest-efficacy, we decided to introduce a DNA-stuffer (fragments of dummy DNA of ~500 bp in size) in place of CDR3-encoding region. DNA stuffers were introduced into the plasmid pMorph31 at the CDR3-flanking RE-sites resulting in plasmids pMorph31_mVLj/MBP-mVHi/AP. In particular, AP-stuffer derived from alkaline phosphatase gene was inserted in place of H-CDR3 by using BssHII/StyI, and MBP-stuffer derived from maltose binding protein gene was inserted in place of L-CDR3 by using BpiI/BsiWI. Noteworthy, due to the digest mode of BpiI (type II RE), we had to prepare two variants of the MBP-stuffer (one for mVLB1 and another one for mVLB3/mVLC3) which differ in the proximity of BpiI-site depending on the master-gene sequence.

Construction of HCDR2 Mini-Library Cassette by Using Primers with Wobbled Positions The intended variability (five amino acid sequence variants per master-gene) was introduced into the selected master-genes in 10 cycles of PCR with Platinum Pfx DNA polymerase (Invitrogen), and a set of forward and reverse primers. Forward primers containing wobbled positions with defined nucleotide ratios were used as follows:

```
                                             (SEQ ID NO: 7)
GGTCGCGGCCTCGAGTGGATTGGCCGCATTG(70%)/A(15%)/T(15%)

ATCCGAACAG(80%)/A(20%)CGGCGGCACCAAATATAACGAA
for mVH1_RV, (SEQ ID NO: 8)
GGCAAAGGTCTCGAGTGGCTGGGCGTGATTTGGA(80%)/G(20%)

GCGG(70%)/A(30%)CGGCA(70%)/G(30%)GCACCGATTATAACGC

CGCC
for mVH2,
and
                                             (SEQ ID NO: 9)
GAAAAACGCCTCGAGTGGGTGGCGACCATTAG(70%)/A(30%)CGGT

GGCA(70%)/G(30%)GTGGCAA(60%)/G(40%)CACCTATTATCCAG

ATAGC
for mVH5.
```

The H-CDR2-regions were completed by constant flanking regions, representing a part of antibody framework 2 and framework 3. Thus it was possible to PCR-amplify and clone the cassettes at a later stage. Since the flanking regions of the VH-mastergenes are different, separate oligos had to be synthesised for the different mastergenes:

Sequence analysis of about 30 randomly picked clones per framework indicated that the desired variants (five per framework) were represented in the HCDR2 with a frequency similar to our design. Only about 10% of randomly picked clones carried unintended nucleotide deletions mainly in the positions which were wobbled in the PCR-primers. In order to ensure low abundance of frame-shifted clones in the library we decided to dilute the plasmid pool encoding variations in HCDR2 with plasmid encoding wild-type VH-framework. Hence in the final library the minor variants in HCDR2 are about 10-fold less abundant than in our initially HCDR2-design.

After this quality control, the PCR products were digested with XhoI/BssHII, and cloned into the respective pMorph31_mVj/MBP-mVHi/AP plasmids (see the paragraphs on the introduction of the DNA stuffers above). Plasmid pool containing the introduced variety in master-genes was mixed 1:10 with plasmid encoding the original master-gene, and used for introduction of the LCDR3-library cassette.

Synthesis of Trinucleotide-Containing Oligonucleotides and CDR3 Library Cassette Preparation Trinucleotide-containing oligonucleotides were synthesized as described previously (Knappik et al., 2000). Diversified trinucleotide-containing ("TRIM") oligonucleotide was mixed with "overlapping" oligonucleotide corresponding to the complementary strand overlapping with the tri-nucleotide-containing oligonucleotide in nondiversified positions. Both oligonucleotides (at concentrations 0.1-0.2 µM) were assembled and amplified in 10 PCR cycles by using end primers (at concentration 1 µM) and Platinum Pfx DNA polymerase (Invitrogen). The forward and reverse end primers annealed to the 5' and 3' ends of the CDR cassette, respectively, and facilitated introduction of restriction sites necessary for cassette cloning. Sequences of all oligonucleotides used for preparation of CDR3 cassettes are listed in Tables 17 (L-CDR3) and 28 (H-CDR3). The amplified CDR3 cassettes were purified on agarose gels and isolated as described elsewhere (Rothe et al., 2008, *J Mol Biol* 376, 1182-1200). Noteworthy, four LCDR3 cassettes (one specific for mVκB3 and mVκC3, others for mVκB1, VκB7 and VκC8) had to be synthesized for each selected VL-framework differing in the proximity of the BpiI site (type II RE) which was necessary for the LCDR3-subcloning.

TABLE 17

LCDR3 specific forward primer mouse and rat

| Name | Sequence |
|---|---|
| mVκB3 Lib63 | GTGGAAGAAGAAGACGCCGCCACCTATTATTGC (SEQ ID NO: 10) |
| mVκB1 Lib64 | GTGGAAGCCGAAGACCTGGGCGTGTATTATTGC (SEQ ID NO: 11) |
| mVκB7 Lib65 | GTGCAGGTGGAAGACCTGACCCATTATTACTGC (SEQ ID NO: 12) |
| mVκC8 Lib66 | GTGCAGGCCGAAGACCTGGCCGTGTATTACTGC (SEQ ID NO: 13) |

Overlapping oligos

| | | |
|---|---|---|
| mouse | Lib71 | CGGCCACGTACGTTTCAGTTCCAGTTTGGTGCC CGCACCAAAGG (SEQ ID NO: 14) |

Vk rev primer

| | | |
|---|---|---|
| mouse | Lib69 | CGGCCACGTACGTTTCAGTTC (SEQ ID NO: 15) |

TABLE 18

HCDR3 specific forward primer mouse and rat

| name | sequence |
|---|---|
| mouse/rat BHU402 | CGCGTGGAAGACTGCGCGC (SEQ ID NO: 16) |

TABLE 18-continued

HCDR3 specific forward primer mouse and rat

| name | sequence |
|---|---|

Overlapping oligos

| | | |
|---|---|---|
| mouse/rat | BHU401 | cataacgaagacgcctTggcccca (SEQ ID NO: 17) |

HCDR3 rev primer

| | | |
|---|---|---|
| mouse/rat | BHU403 | CATAACGAAGACGCCTTG (SEQ ID NO: 18) |

Sub-Cloning of CDR3 Library Cassettes into Master-Genes in Phagemid Format

The amplified LCDR3-library cassettes were inserted in place of the MBP DNA stuffer in pMorph31_mVLj-mVHi/AP plasmids with diversified HCDR2 by using BpiI/BsiWI. We used typically ~2 µg vector for ligation with 2-molar excess of the LCDR3-cassette. The vector-insert mixture was pre-incubated 10 minutes at 56° C. prior addition of T4 DNA ligase and buffer, and after the overnight incubation at 16° C., the ligation mixture was incubated 10 minutes at 65° C. in order to inactivate the ligase. Ligated DNA was then purified by 2-butanol/glycogen precipitation, and electroporated into Top10F' competent cells (Invitrogen). After transformation and outgrowth for 1 h at 37° C. in SOB medium, the number of transformed cells was determined by titration on LB/cam/glucose (1%) agar plates. Amplification of the transformed clones was performed in liquid medium (LB/cam/glucose (1%)) overnight at 22° C. and then at 30° C. until $OD_{600nm}$ 2.0 was reached. An aliquot of the liquid culture was used for glycerol frozen stock, and the rest was used for DNA maxiprep by using Qiagen kit.

The highly variable L-CDR3-cassette was completed by constant flanking regions, representing a part of antibody framework 3 and the terminal VL-antibody framework 4. Thus it was possible to PCR-amplify and clone the cassette at a later stage. Since the flanking regions of the VL-mastergenes were different, separate oligos had to be synthesised for the different mastergenes:

```
                                            (SEQ ID NO: 19)
mVkB3 = mVkC3
5' GAAGACGCCGCCACCTATTATTGC-T8-CAG-T9-T10-T11-
T12-CCG-T13-ACCTTTGGCGGTGGCACCA (SEQ ID NO: 20)
mVkB1
5' GAAGACCIGGGCGTGTATTATTGC-T8-CAG-T9-T10-T11-
T12-CCG-T13-ACCTTTGGCGGTGGCACCA (SEQ ID NO: 21)
mVkB7
5' GAAGACCTGACCCATTATTACTGC-T8-CAG-T9-T10-T11-
T12-CCG-T13-ACCTTTGGCGGTGGCACCA (SEQ ID NO: 22)
mVkC8
5' GAAGACCTGGCCGTGTATTACTGC-T8-CAG-T9-T10-T11-
T12-CCG-T13-ACCTTTGGCGGTGGCACCA
``` wherein T8-T13 are TRIM-mixes.

Figure 19:
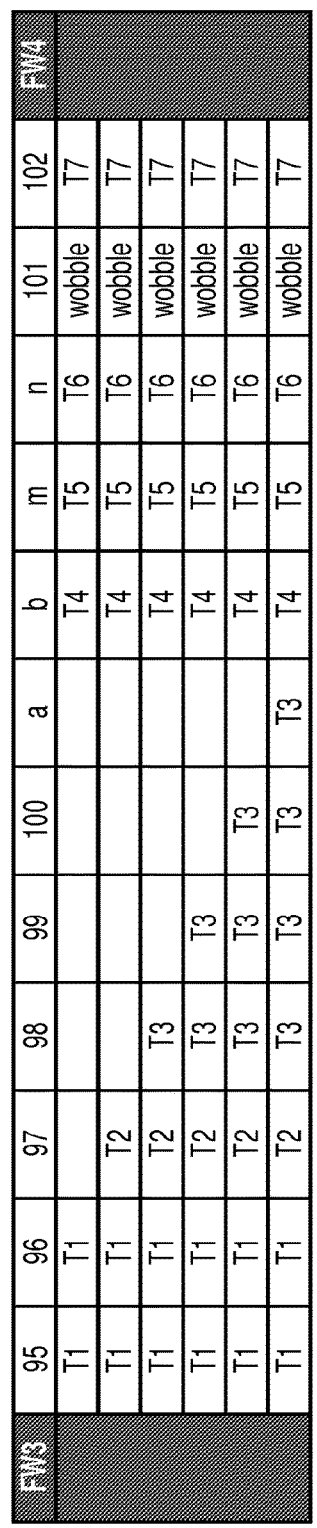
FIG. 19 shows the design of the separate HCDR3 cassettes for the HCDR3 sequences of the lengths of 7, 8, 9, 10, 11 and 12 amino acids.

For H-CDR3 construction, a separate CDR cassette was generated for each H-CDR3 length. The composition of the separate cassettes is shown in FIG. 19.

The highly variable H-CDR3-cassette was completed by constant flanking regions, representing a part of antibody framework 3 and the terminal VH-antibody framework 4. Thus it was possible to PCR-amplify and clone the cassettes at a later stage. Since the flanking frameworks of the different VH-mastergenes are identical, one oligo could be used for all mastergenes:

(SEQ ID NO: 23)
5' GTGGAAGACTGCGCGCGG-T1-T1-(T2)-(T3)-(T3)-(T3)-
(T3)-T4-T5-T6-W-T7-TGGGGCCAAGGCGTCT, wherein T1-T7 are TRIM-mixes and W are wobble as described herein above.

Amplified diversified HCDR3 library cassettes of various lengths (7, 8, 9, 10, 11, and 12 residues) were mixed together at molar ratios reflecting the planned HCDR3 length distribution, and subcloned into the pMorph31_mVLj-mVHi/AP plasmids with diversified HCDR2 and LCDR3 by using BssHII/StyI. Typically, 15-20 μg vector were ligated with 2-molar excess of the HCDR3-cassette mixture. The ligation-, transformation-, and clone propagation-conditions used for subcloning of the HCDR3 cassette-mixture did not vary from the conditions used for subcloning of the LCDR3 cassettes. VL- and VH-sequence analysis of ~70 clones and restriction analysis of 24 randomly picked clones and of pool DNA-maxiprep from each sublibrary were performed in order to assess the library quality.

The theoretical diversity of $2.4 \cdot 10^8$ individual clones per sublibrary was readily covered after the transformation of plasmid pool into *E. coli* (Table 19).

TABLE 19

|  | Framework | LCDR3/HCDR2 | | LCDR3/HCDR2/HCDR3 | | |
|---|---|---|---|---|---|---|
|  |  | theoretical diversity | library size | theoretical diversity | library size | Percentage of correct clones [%] |
| Mouse | VκB3-VH1 RV | 2.4E+08 | 5.1E+08 | 6.1E+21 | 4.3E+09 | 83% |
|  | VκC3-VH1 RV | 2.4E+08 | 5.5E+08 | 6.1E+21 | 3.2E+09 | 91% |
|  | VκB3-VH5 | 2.4E+08 | 2.3E+08 | 6.1E+21 | 1.1E+09 | 89% |
|  | VκC3-VH5 | 2.4E+08 | 2.6E+08 | 6.1E+21 | 2.6E+09 | 85% |
|  | VκB1-VH2 | 2.4E+08 | 2.6E+08 | 6.1E+21 | 2.2E+09 | 89% |
|  | All 5 mouse libraries | 1.2E+09 |  | 3.1E+22 | 1.3E+10 | 87% |
| Rat | Vκ1-VH5 | 2.4E+08 | 3.8E+08 | 6.1E+21 | 1.5E+09 | 88% |

Figure 26:
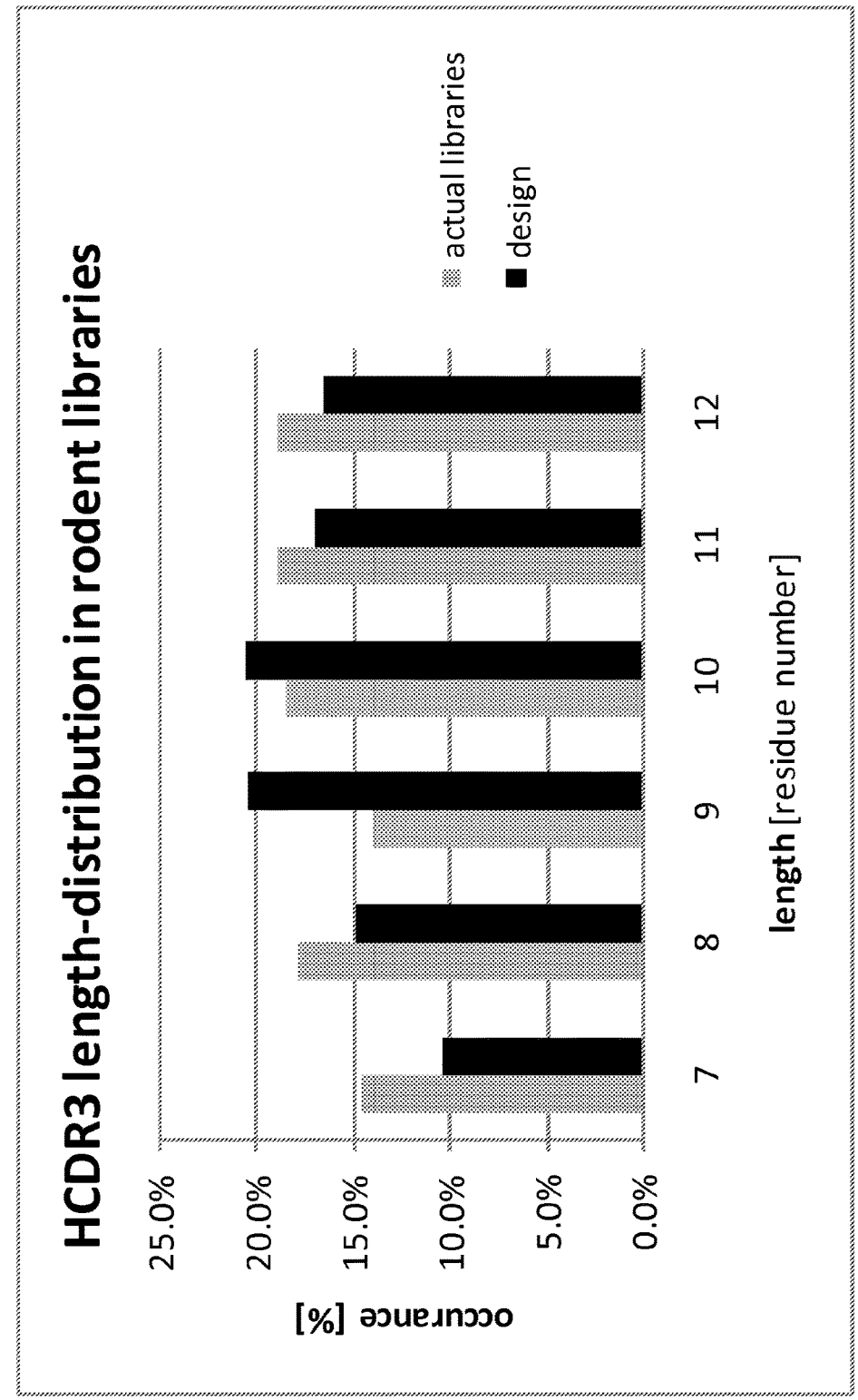
FIG. 26 depicts the planned HCDR3 length distribution as compared to the HCDR3 length distribution actually found in the murine library of the present invention.
Figure 27D:
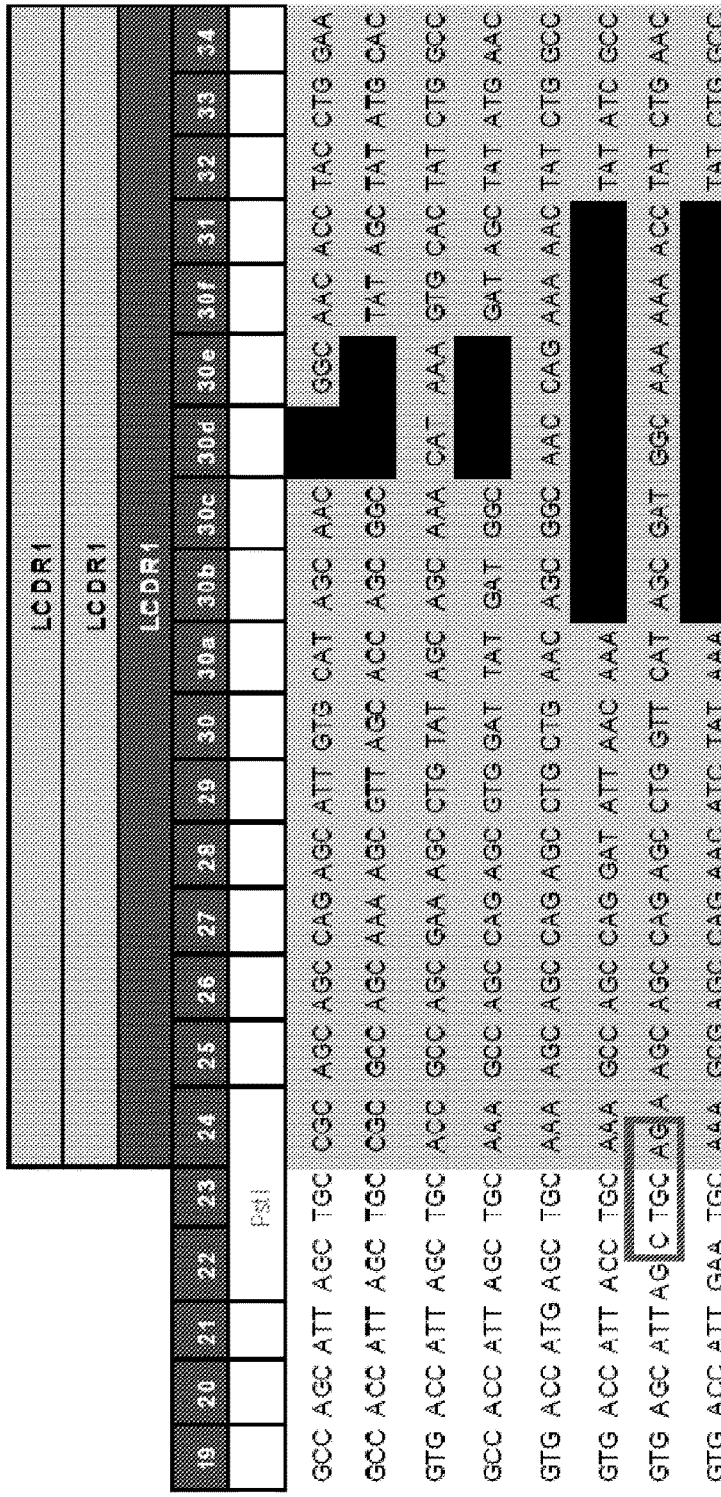
FIGS. 27 a-d, 28 a-d, 29 a-d, 30 a-d, and 31 a-d depict an overview of the all synthesized master genes of the murine library of the present invention. Kabat indicates the position of amino acid residue in VL- or VH-sequences. mVL denotes murine variable domain in the light chain (exclusively of the type kappa), and mVH denotes murine variable domain in the heavy chain. Murine Vk germ-line genes encode mVL starting from position 1 (at the N-terminus of framework 1) to 95 (at the C-terminus of L-CDR3), and murine Jk germ-line genes encode for the very C-terminal residue in L-CDR3 (constant position 96) and whole framework 4 in mVL (positions 97-108). We have chosen murine Jk2, since Tyr is the most frequent residue in position 96 of rearranged antibodies found in the IMGT database.
Figure 28A:
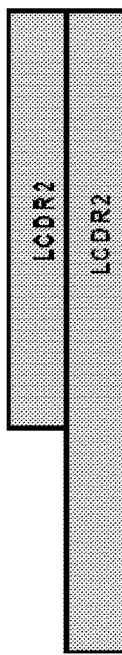
Figure 28C:
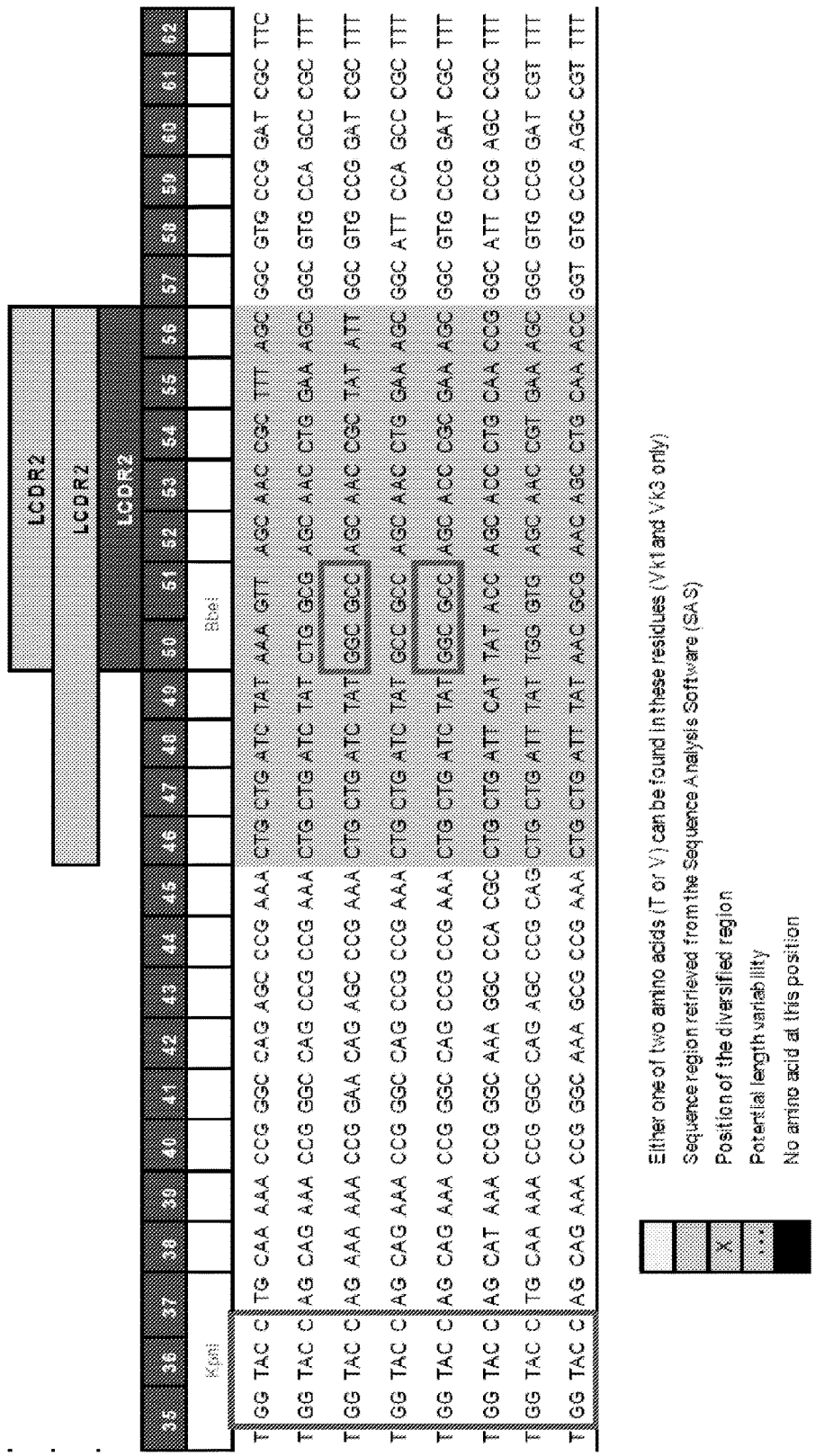
Figure 28D:
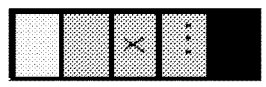
Figure 29D:
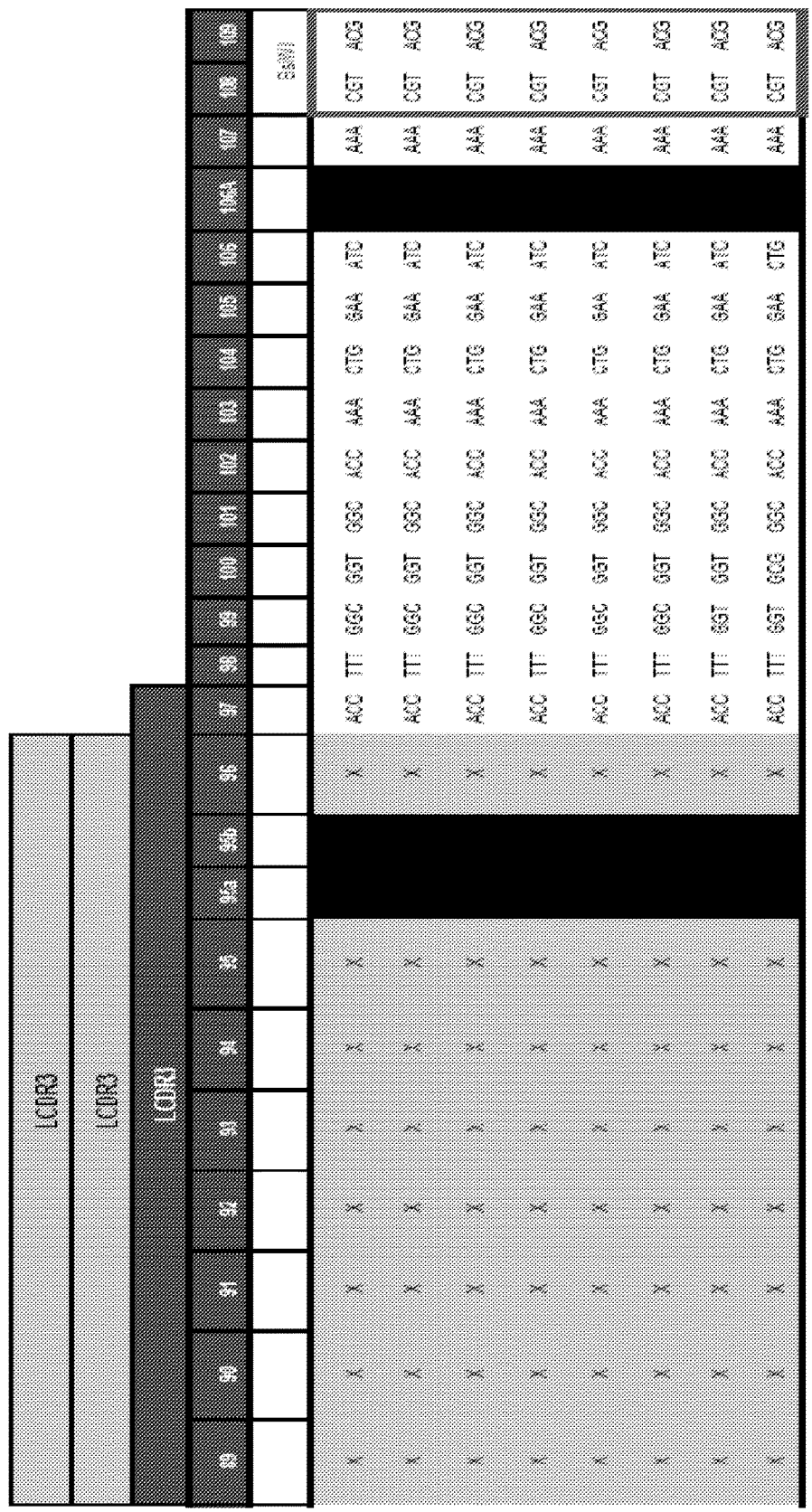
Figure 30C:
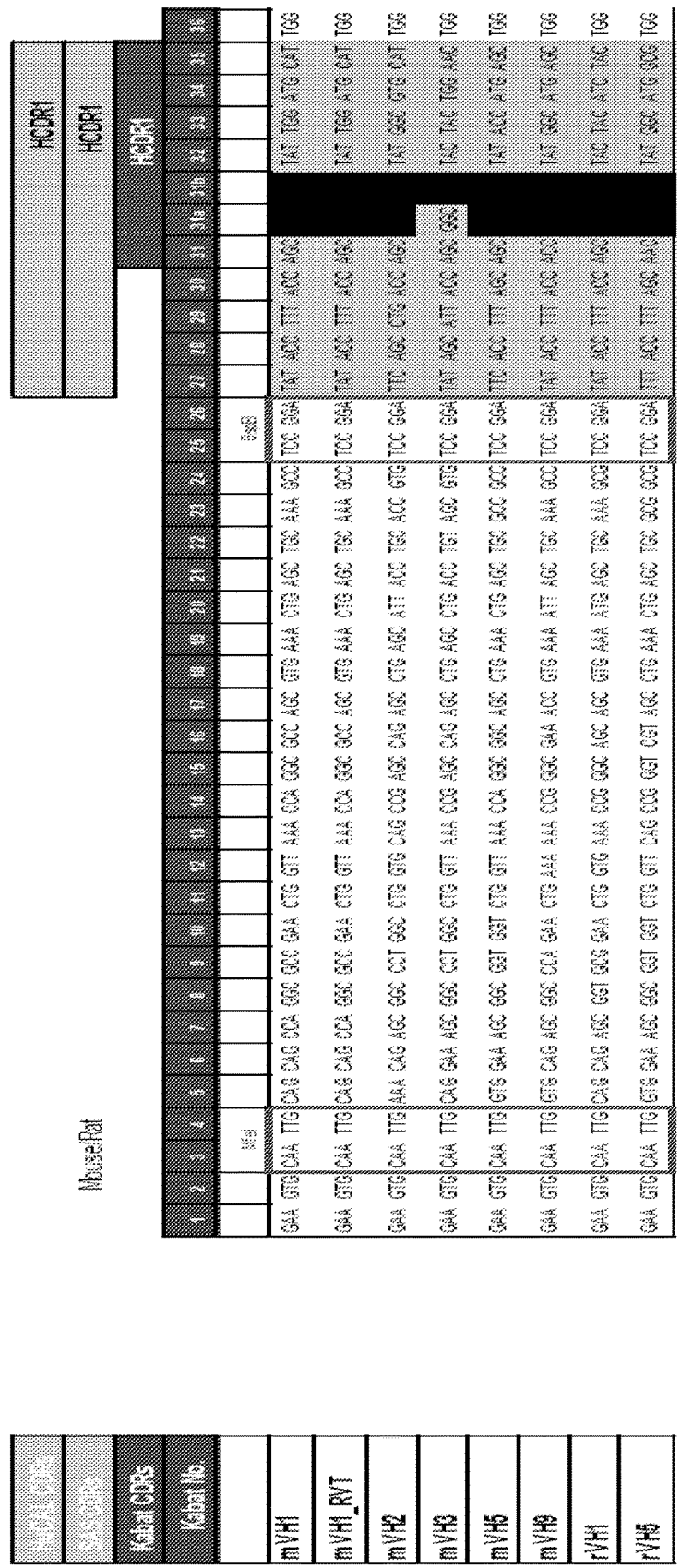

We obtained about $2.7 \cdot 10^9$ individual clones per sublibrary, or $1.3 \cdot 10^{10}$ individual clones for the entire HuCAL MOUSE library comprising all five diversified murine Fv-frameworks (FIGS. 19-24). The achieved diversity of the HuCAL Mouse antibody library is 2 orders of magnitude larger than B cell population of an immunologically mature mouse (Rajewsky et al., 1987, *Science* 238, 1088-1094), and the quality of the library was very high—about 87% of analyzed sequences were in-frame and did not contain undesirable amino acid mutations (see Table 19). Sequence analysis of randomly picked clones indicated that amino acid distribution in LCDR3 and HCDR3 did not vary substantially from our design (FIGS. 20-25), and also the actual HCDR3 length-distribution was well in accordance with the design (FIG. 26).

Sub-Cloning of LCDR3 Library Cassette into Auxiliary Cloning Vector for Affinity Maturation The amplified LCDR3-library cassettes were inserted in place of a DNA stuffer in pGA18 cloning vector by using BpiI/BsiWI. This vector does not possess any promoter and replicates in bacteria with a high copy number. The ligation-, transformation-, and clone propagation-conditions used for subcloning of the LCDR3 cassettes into the plasmid pMorph31_mVLj-mVHi/AP or into the cloning vector pGA18 were basically the same.

The diversity of the LCDR3 maturation cassettes is shown in Table 20

TABLE 20

|  |  | LCDR3 maturation cassette | | |
|---|---|---|---|---|
|  | framework | theoretical diversity | library size | percentage of correct clones [%] |
| Mouse | VκB1 | 4.7E+07 | 2.4E+09 | 89 |
|  | VκB3 | 4.7E+07 | 2.0E+09 | 96 |
|  | VκC3 | 4.7E+07 | 2.0E+09 | 96 |
| Rat | Vκ1 | 4.7E+07 | 4.3E+09 | 95 |

Amplification of HCDR2 Maturation Cassettes

The insert comprising HCDR2 maturation-cassettes for mVH was prepared in two steps. In the first step, diversified trinucleotide-containing ("TRIM") oligonucleotide was mixed with "overlapping" oligonucleotide corresponding to the complementary strand overlapping with the trinucleotide-containing oligonucleotide in nondiversified positions. Both oligonucleotides (at concentrations 0.1-0.2 μM) were assembled and amplified in 10 PCR cycles by using forward and reverse "mat" primers (at concentration 1 μM) and Platinum Pfx DNA polymerase (Invitrogen) resulting in PCR product Ai. In parallel, the framework 3 of mVHi was amplified from pMorph31_mVLj/MBP-mVHi/AP template (see above) in 10 PCR cycles by using forward and reverse "FW3" primers (at concentration 1 μM) resulting in PCR product Bi. In a next step, the corresponding PCR products Ai and Bi (each at concentration ~20 nM) were assembled and amplified in 10 PCR cycles by using corresponding forward "mat" and reverse "FW3" primers resulting in PCR products encoding diversified HCDR2/FW31 and flanked by XhoI and BssHII RE-sites and 5' and 3', respectively. Sequences of all oligonucleotides used for preparation of maturation HCDR2 cassette are listed in Table 21.

TABLE 21

| | | |
|---|---|---|
| mLib74 | mu VH1-RVT_HCDR2mat for | GGTCGCGGCCTCGAGTGG (SEQ ID NO: 24) |
| mLib75 | mu VH1-RVT HCDR2mat_overlap | GTTTATCCACGGTCAGGGTCACCCGGCTTTTGAA (SEQ ID NO: 25) |
| mLib76 | mu VH1-RVT_HCDR2mat rev | GTTTATCCACGGTCAGGGTCACC (SEQ ID NO: 26) |
| mLib77 | mu VH1RVT FW3 for | GGTGACCCTGACCGTGGATAAAC (SEQ ID NO: 27) |
| mLib78 | mu VH2_HCDR2mat for | GGCAAAGGTCTCGAGTGG (SEQ ID NO: 28) |
| mLib79 | mu VH2_HCDR2mat_overlap | GCTGTTATCTTTGCTGATGCTCAGGCGGCTAATAAA (SEQ ID NO: 29) |
| mLib80 | mu VH2_HCDR2mat rev | GCTGTTATCTTTGCTGATGC (SEQ ID NO: 30) |
| mLib81 | mu VH2 FW3 for | GCATCAGCAAAGATAACAGC (SEQ ID NO: 31) |
| mLib82 | mu VH5_HCDR2mat for | GAAAAACGCCTCGAGTGG (SEQ ID NO: 32) |
| mLib83 | mu VH5_HCDR2mat_overlap | CGCGGCTAATGGTAAAGCGGCCTTTCACGCT (SEQ ID NO: 33) |
| mLib84 | mu VH5_HCDR2mat rev | CGCGGCTAATGGTAAAGC (SEQ ID NO: 34) |
| mLib85 | mu VH5 FW3 for | GCTTTACCATTAGCCGCG (SEQ ID NO: 35) |
| mLib86 | mu VH1/2/5 AP FW3 rev | CGACGCCCAGCGCGCAATAATA (SEQ ID NO: 36) |
| ratLib88 | rat VH1_HCDR2mat for | GGCCAGGGCCTCGAGTGG (SEQ ID NO: 37) |
| ratLib89 | at VH1_HCDR2mat_overlap | CCACGGTAAAGGTCGCTTTGCCTTTGAATTT (SEQ ID NO: 38) |
| ratLib90 | rat VH1_HCDR2mat rev | CCACGGTAAAGGTCGCTTTG (SEQ ID NO: 39) |
| ratLib91 | rat VH1 FW3 for | CAAAGCGACCTTTACCGTGG (SEQ ID NO: 40) |
| ratLib92 | rat VH1 FW3-AP rev | CGACGCCCAGCGCGCAGTAATACACC (SEQ ID NO: 41) |
| ratLib93 | rat VH5_HCDR2mat for | ACCAAAGGTCTCGAGTGG (SEQ ID NO: 42) |
| ratLib94 | rat VH5_HCDR2mat_overlap | CACGGCTAATGGTAAAACGGCCTTTCACGCT (SEQ ID NO: 43) |
| ratLib95 | rat VH5_HCDR2mat rev | CACGGCTAATGGTAAAACGG (SEQ ID NO: 44) |
| ratLib96 | rat VH5 FW3 for | CCGTTTTACCATTAGCCGTG (SEQ ID NO: 45) |
| ratLib97 | rat VH5 FW3-AP rev | CGACGCCCAGCGCGCAATAATAGGTC (SEQ ID NO: 46) |

The H-CDR2-cassettes were completed by constant flanking regions, representing a part of antibody framework 2 and framework 3. Thus it was possible to PCR-amplify and clone the cassettes at a later stage. Since the flanking regions of the VH-mastergenes are different, separate oligos had to be synthesised for the different mastergenes.

(SEQ ID NO: 47)
mVH1_RV_HCDR2mat
5' GGTCGCGGCCTCGAGTGGATTGGC-MMT1-ATT-MMT2-CCG-

MMT1-MMT3-MMT4-MMT1-MMT5-MMT1-TAT-AAC-W1-AAATTCA

AAAGCCGGGTGACC (SEQ ID NO: 48)
mVH2_HCDR2mat
5' GGCAAAGGTCTCGAGTGGCTGGGC-W2-ATT-MMT6-MMT7-MMT8-

GGC-MMT9-ACC-MMT1-TAT-AAC-MMT10-GCCTTTATTAGCCGCC

TGAGCATC (SEQ ID NO: 49)
mVH5_HCDR2mat
5' GAAAAACGCCTCGAGTGGGTGGCG-MMT1-ATT-MMT11-MMT12-

MMT13-W3-MMT12-MMT14-MMT15-TATTATW4GATAGCGTGAAAGG

CCGCTTTACC, wherein MMT1-MMT15 are TRIM-mixes and W are wobbles as described herein above The diversity of the HCDR2 maturation cassette is shown in Table 22:

TABLE 22

| | framework | theoretical diversity | library size | percentage of correct clones [%] |
|---|---|---|---|---|
| Mouse | VH1 RV | 1.1E+09 | 4.0E+09 | 83% |
| | VH2 | 9.9E+06 | 2.3E+09 | 86% |
| | VH5 | 3.6E+09 | 6.0E+09 | 74% |
| Rat | VH5 | 1.2E+08 | 4.0E+09 | 88% |

HCDR2 maturation cassette

Sub-Cloning of HCDR2 Maturation Cassettes into Auxiliary Cloning Vector

First, we sub-cloned the three selected murine VH-master-genes mVH1 RV, mVH2 or mVH5 (fragments encoding residues 1-94, i.e. ORF starting from the N-terminus of FW1 till very C-terminus of FW3) from pMorph31 phage-display vector (see above) into an auxiliary cloning vector pGA18 by using MfeI/BssHII. In next step, the master-gene region between Xho I and BssHII RE-sites was replaced by a DNA stuffer (about 600 bp). We inserted the DNA stuffer in order to facilitate sub-cloning of the amplified HCDR2 maturation diversified cassette into the cloning vectors pGA18_mVHi by using XhoI/BssHII in a subsequent step. Then, we sub-cloned the amplified diversified HCDR2 (see the chapter above) into the cloning vector pGA18_mVHi in place of the DNA stuffer by using XhoI/BssHII. Typically, 15-20 µg vector were ligated with 2-molar excess of the HCDR2-cassette. The ligation-, transformation-, and clone propagation-conditions used for subcloning of the HCDR2 cassette did not vary from the conditions used for subcloning of the LCDR3 cassettes.

Summary

The mouse antibody library generated in the presented study comprises diversified LCDR3 and HCDR3 regions. CDR3 library cassettes were generated from mixed trinucleotides (TRIM) which encode only desirable residues in the CDR3-cassettes preventing introduction of cysteine- and stop-codons. Since it has been recognized that antigen-antibody interaction involves also framework residues and therefore it might be beneficial to screen for binders from a conformation-space broader than one offered by a variety of distinct sequences in CDRs only, we selected five different murine Fv-frameworks. Hence five distinct libraries with diversified LCDR3 and HCDR3 were generated in parallel. Sequencing of unselected clones indicated that overall incidence of undesirable DNA mutations, deletions and insertions introduced by PCR amplification of the LCDR3 and HCDR3 cassettes was low (~10%). In order to comply with the essential requirements of the HuCAL® cloning-modularity, following mutations were introduced into germ-line sequences: V2I in mVLB1, T25S in mVH3, K46E in mVH9 and K66R/A67V in mVH1_RV. The amino acid sequence corresponding to positions 1-4 in all mVHs was changed into EVQL (SEQ ID NO: 50).

An overview of the all synthesized master genes encoding variable domain is presented in FIGS. 27-31. Kabat indicates the position of amino acid residue in VL- or VH-sequences. mVL denotes murine variable domain in the light chain (exclusively of the type kappa), and mVH denotes murine variable domain in the heavy chain. Murine Vκ germ-line genes encode mVL starting from position 1 (at the N-terminus of framework 1) to 95 (at the C-terminus of L-CDR3), and murine Jκ germ-line genes encode for the very C-terminal residue in L-CDR3 (constant position 96) and whole framework 4 in mVL (positions 97-108). We have chosen murine Jκ2, since Tyr is the most frequent residue in position 96 of rearranged antibodies found in the IMGT database.

Murine VH germ-line genes encode mVH starting from position 1 (at the N-terminus of framework 1) to 94 (at the very C-terminus of framework 3). HCDR3 sequence is encoded by the D germ-line genes. We reasoned that biochemical and biophysical properties of the VH-domain depend also on its HCDR3 sequence, and therefore we decided to introduce one particular HCDR3 sequence into all mVH master-genes for the purpose of the master-gene comparison. The HCDR3 sequence (WGGDGFYAMDY) (SEQ ID NO: 51) was derived from antibody 4D5, and had been used previously for the assessment of human master-genes prior the construction of the original HuCAL library (Knappik et al., 2000, *J Mol Biol* 296, 57-86). Murine JH germ-line genes encode for a C-terminal part of HCDR3 and whole framework 4 (positions 103-113). We have chosen murine JH2 (sequence WGQGTTLTVSS) (SEQ ID NO: 52) for the design of framework 4 because JH2 was frequently found in rearranged antibodies deposited in the IMGT database, and allowed us to introduce two restriction endonuclease sites (StyI and BlpI) indispensable for the HuCAL cloning modularity.

Example 1.7

Test Panning with the Murine Library

Murine M-CSF (macrophage colony stimulation factor) was used as antigen for test panning. Here we handled each sub-library separately and in addition used a pooled full library consisting of all sub-libraries.

Panning mM-CSF was diluted in PBS to coat with the standard concentration of 50 µg/ml. For each sublibrary 2 wells of a microtiter plate were coated with antigen using 300 ul antigen solution per well. The plate was stored O/N at 4° C. Then the antigen solution was removed from the coated wells by rapidly inverting the plate over a plastic tray. The coated wells were washed twice with 400 µl PBS and blocked with for 2 h at RT on a microtiter plate shaker.

Meanwhile the phage blocking mixtures were incubated in 2 ml reaction tubes for 2 h at RT shaking gently. After the blocking procedure the wells were washed 2× with 400 µl PBS and the 300 µl of the pre-blocked phage mix transferred into each blocked well. It was incubated for 2 h at RT on a microtiter plate shaker. After that the phage solution from the antigen coated wells were removed by rapidly inverting the plate over a plastic tray and plates were washed with the following washing conditions (Table 23):

TABLE 23

| 1st round | 2nd round | 3rd round |
|---|---|---|
| 3 × PBST quick | 1 × PBST quick | 10 × PBST quick |
| 2 × PBST for 5 min | 4 × PBST for 5 min | 5 × PBST for 5 min |
| 3 × PBS quick | 1 × PBS quick | 10 × PBS quick |
| 2 × PBS for 5 min | 4 × PBS for 5 min | 5 × PBS for 5 min |

All washing steps were done at RT. After the washing steps all traces of the wash solution were removed by carefully tapping the microtiter plate on a new stack of paper towels.

For the elution of specifically bound phage, we added 300 µl 20 mM DTT in 10 mM Tris/HCl, pH8.0, to each selection well and incubated at RT for 10 min without shaking. The DTT eluates of each selection were collected. E. coli TG1 with an OD600 nm of 0.6-0.8 was added to the phage eluates of each selection and were incubated in an incubator without shaking. After infection bacteria were plated out evenly on two large LB/Cm/Glu agar plates for each selection and incubated O/N at 37° C.

For the following panning rounds bacterial suspensions of each pool were collected and used to propagate phages for an additional panning round as described above.

After each round of panning against mM-CSF the phage titer was determined. The expected range goes from $1\times10^{10}$-$1\times10^{12}$ phage/mL for the input and $10^4$-$10^6$ phage/mL for the output. Table 24 shows the input and the output after each round of panning and all values are in the expected range.

TABLE 24

| Pool | 1st round | | 2nd round | | 3rd round | |
|---|---|---|---|---|---|---|
| | INPUT | OUTPUT | INPUT | OUTPUT | INPUT | OUTPUT |
| VH1 VkB3 | $1 \times 10^{12}$ | $2.6 \times 10^5$ | $3.4 \times 10^{10}$ | $8 \times 10^4$ | $2 \times 10^{10}$ | $2.6 \times 10^6$ |
| VH2 VkB1 | $1 \times 10^{12}$ | $8 \times 10^4$ | $4.6 \times 10^9$ | $4.1 \times 10^4$ | $3.6 \times 10^9$ | $3.2 \times 10^6$ |
| VH5 VkB3 | $1 \times 10^{12}$ | $3.7 \times 10^4$ | $2.6 \times 10^{10}$ | $5.2 \times 10^4$ | $4 \times 10^9$ | $1.8 \times 10^5$ |
| VH1 VkC3 | $1 \times 10^{12}$ | $1.6 \times 10^5$ | $2 \times 10^{10}$ | $1.8 \times 10^4$ | $5.8 \times 10^9$ | $4 \times 10^5$ |
| VH5 VkC3 | $1 \times 10^{12}$ | $8 \times 10^4$ | $2.8 \times 10^{10}$ | $1.2 \times 10^3$ | $1.8 \times 10^{10}$ | $1.2 \times 10^6$ |
| Full library | $1 \times 10^{12}$ | $2.4 \times 10^5$ | $2.4 \times 10^{10}$ | $2.88 \times 10^3$ | $1.4 \times 10^{10}$ | $2 \times 10^6$ |

Sub-Cloning of Selected Pools

DNA was prepared and with digested with EcoRI, XbaI and BmtI. Nucleic acids were separated on a preparative 1% DNA agarose gel and the band referring to the Fab encoding DNA (~1470 bp) was extracted, ligated into pMorphx9_FH vector and electroprated into competent TG1 F-cells. Single colonies were picked and incubated in round bottom 96-well microtiter plates in 100 μl 2×YT/Cm/1% Glu medium O/N at 30° C. The next morning, 100 μl sterile 30% glycerol in 2×YT to each well of the O/N master plate were added and stored at −80° C.

Micro-Expression of Fab Protein

For the preparation of expression plates 5 μl per well was replicated from the master plate to the corresponding well of 96-well microtiter plate containing 100 μl 2×YT/Cm/0.1% Glu medium per well. Thereafter the microtiter plates were shaken at 30° C. and 400 rpm until the cultures are slightly turbid (~2-4 h) with an OD600 nm of ~0.5 following induction by addition of 20 μl 2×YT/Cm containing 3 mM IPTG. Each plate was sealed with gas-permeable tape and covered with a lid and incubated O/N at 30° C. shaking at 400 rpm.

Primary ELISA Screening 384-well Maxisorp microtiter plates were coated with 20 μl antigen solution (mM-CSF) per well at a concentration of 1 μg/ml diluted in PBS and incubated at 4° C., O/N. Controls were applied as described below. The antigen solution as removed from the coated ELISA plate by rapidly inverting them over the sink and washing the wells once with TBST. ELISA plate was blocked with 100 μl 5% MTBST for 2 h at RT, shaking gently. To each well of the expression plate, 40 μl BEL buffer containing 2.5 mg/ml Lysozyme was added and shaked for 1 h at 22° C. at 400 rpm. After lysis of bacteria 40 μl 12.5% MTBS was added per well and incubated for an additional 30 min at 400 rpm and 22° C. for blocking. The blocked ELISA screening plate was rinsed once with TBST and tapped it on a stack of paper towels. Afterwards 20 μl of the blocked BEL extracts was transferred from the expression plate to the corresponding well of the blocked ELISA plate. Likewise 20 μl of the expression positive control extract was transferred to well of the ELISA plate. The ELISA plate was incubated for 1.5 h at RT on a microtiter plate shaker, shaking gently. The ELISA plates was washed 5× quickly with TBST. Then 20 μl goat anti-mouse F(ab')2 antibody-AP conjugate diluted 1:5000 in TBST was added and incubated 1 h at RT. After 1 h incubation the ELISA plates were 5× washed quickly with TBST and 20 μl AttoPhos™ substrate was added to each well (diluted 1:5 in TBST). Fluorescence readings at excitation of 440±25 nM and emission of 550±35 nM was taken.

Controls:
well E12=>positive control for expression and extraction
well F12=>background control of goat anti-mouse F(ab)2 antibody-AP conjugate
well G12=>background control of the AttoPhos™ substrate
well H12=>background of ELISA plate For selecting the best binders an ELISA screening was performed after three rounds of solid-phase panning. 184 for each sublibrary and 2×184 for the full library of the transformed clones were picked and transferred in 96-well microtiter plate for the masterplates. Then a periplasmatic expression was induced and an ELISA screening was performed with mM-CSF as coating antigen. Table 25 shows as example of the fluorescence ELISA readings of one plate of the full library screening. Only the hits with intensity signals of 5-10 (**) and over 10 ($^a$) fold over the background were selected. Hits with intensity signals of 2-5 fold over the background are indicated by $^{bb}$.

TABLE 25

| | 1 | 2 | 3 | 4 | 5 | 6 | 7 | 8 | 9 | 10 | 11 | 12 |
|---|---|---|---|---|---|---|---|---|---|---|---|---|
| A | 1379** | 6959$^a$ | 579$^{bb}$ | 954* | 1573* | 506$^{bb}$ | 368 | 353 | 262 | 346 | 631$^{bb}$ | 2045$^a$ |
| B | 970** | 720$^{bb}$ | 723$^{bb}$ | 583$^{bb}$ | 362 | 411$^{bb}$ | 2898$^a$ | 294 | 232 | 373$^{bb}$ | 263 | 303 |
| C | 586$^{bb}$ | 4922$^a$ | 919$^{bb}$ | 6965$^a$ | 1151* | 341 | 291 | 433$^{bb}$ | 322 | 747$^{bb}$ | 248 | 284 |
| D | 2970$^a$ | 3118$^a$ | 520$^{bb}$ | 527$^{bb}$ | 427$^{bb}$ | 388$^{bb}$ | 323 | 220 | 317 | 455$^{bb}$ | 241 | 570$^{bb}$ |
| E | 1026** | 1419** | 696$^{bb}$ | 662$^{bb}$ | 475$^{bb}$ | 307 | 319 | 8265$^a$ | 301 | 276 | 285 | 12819 |
| F | 709$^{bb}$ | 3998$^a$ | 1126** | 563$^{bb}$ | 544$^{bb}$ | 1962$^a$ | 561$^{bb}$ | 298 | 741$^{bb}$ | 261 | 310 | 251 |
| G | 818$^{bb}$ | 1472** | 1303** | 2730$^a$ | 562$^{bb}$ | 328 | 321 | 291 | 896$^{bb}$ | 244 | 550$^{bb}$ | 150 |
| H | 9040$^a$ | 853$^{bb}$ | 1583** | 788$^{bb}$ | 941* | 375$^{bb}$ | 555$^{bb}$ | 314 | 397$^{bb}$ | 291 | 2065$^a$ | 298 |

Sequencing of ELISA Positive Fabs

The heavy and the light chain of primary hits were sequenced. Tables 26 (VH1VkC3), 27 (VH5VkC3), 28 (full library), 29 (VH1VkB3), 30 (VH2VkB1) and 31 (VH5VkB3) show CDR regions of some unique binders. The binders isolated from the same sublibraries comprise the same CDR1 and CDR2 regions.

TABLE 26

(selected binders from the sublibrary VH1VkC3):

Heavy chain

| Clone | HCDR1 (SEQ ID NOS 53, 53, 53, 53, 53, 53, and 53) | HCDR2 (SEQ ID NOS 54, 54, 54, 54, 54, 54, and 54) | HCDR3 (SEQ ID NOS 55-61) |
|---|---|---|---|
| mM-CSF1.3.7C4 | YTFTSYWMH | RIDPNSGGTKYNEKFKS | APYYAFAY |
| mM-CSF1.3.7E5 | YTFTSYWMH | RIDPNSGGTKYNEKFKS | SDYRGAFAY |
| mM-CSF1.3.7G2 | YTFTSYWMH | RIDPNSGGTKYNEKFKS | SYYYAFDV |
| mM-CSF1.3.7G7 | YTFTSYWMH | RIDPNSGGTKYNEKFKS | DAGVDDFDV |
| mM-CSF1.3.8A3 | YTFTSYWMH | RIDPNSGGTKYNEKFKS | SRAYAGYVFDY |
| mM-CSF1.3.8B9 | YTFTSYWMH | RIDPNSGGTKYNEKFKS | SYSYYEAFDY |
| mM-CSF1.3.7G5 | YTFTSYWMH | RIDPNSGGTKYNEKFKS | SYTSRFDY |

Light chain

| Clone | LCDR1 (SEQ ID NOS 62, 62, 62, 62, 62, 62, and 62) | LCDR2 (SEQ ID NOS 63, 63, 63, 63, 63, 63, and 63) | LCDR3 (SEQ ID NOS 64-70) |
|---|---|---|---|
| mM-CSF1.3.7C4 | KASQSVDYDGDSYMN | YAASNLESGIPARFSGS | QQYNSYPL |
| mM-CSF1.3.7E5 | KASQSVDYDGDSYMN | YAASNLESGIPARFSGS | QQYWSRPY |
| mM-CSF1.3.7G2 | KASQSVDYDGDSYMN | YAASNLESGIPARFSGS | SQYWSYPF |
| mM-CSF1.3.7G7 | KASQSVDYDGDSYMN | YAASNLESGIPARFSGS | QQSSHYPL |
| mM-CSF1.3.8A3 | KASQSVDYDGDSYMN | YAASNLESGIPARFSGS | QQSNAYPR |
| mM-CSF1.3.8B9 | KASQSVDYDGDSYMN | YAASNLESGIPARFSGS | SQKIQRPY |
| mM-CSF1.3.7G5 | KASQSVDYDGDSYMN | YAASNLESGIPARFSGS | QQDYEKPY |

TABLE 27

(selected binders from the sublibrary VH5VkC3):

Heavy chain

| Clone | HCDR1 (SEQ ID NOS 71, 71, and 71) | HCDR2 (SEQ ID NOS 72, 72, and 72) | HCDR3 (SEQ ID NOS 73-75) |
|---|---|---|---|
| mM-CSF1.3.9C8 | FTFSSYTMSWVRQTPEKRLE | TISGGGGNTYYPDSVKG | RWYYAFDY |
| mM-CSF1.3.10G5 | FTFSSYTMSWVRQTPEKRLE | TISGGGGNTYYPDSVKG | RYYHYFSDFDY |
| mM-CSF1.3.10H5 | FTFSSYTMSWVRQTPEKRLE | TISGGGGNTYYPDSVKG | WIYYAFDY |

Light chain

| Clone | LCDR1 (SEQ ID NOS 62, 62, and 62) | LCDR2 (SEQ ID NOS 63, 63, 63) | LCDR3 SEQ ID NOS 76-78) |
|---|---|---|---|
| mM-CSF1.3.9C8 | KASQSVDYDGDSYMN | YAASNLESGIPARFSGS | QLGQEKPY |
| mM-CSF1.3.10G5 | KASQSVDYDGDSYMN | YAASNLESGIPARFSGS | QQGNHFPA |
| mM-CSF1.3.10H5 | KASQSVDYDGDSYMN | YAASNLESGIPARFSGS | QQGTSKPY |

TABLE 28

(selected binders from the full library):

Heavy chain

| Clone | Framework | HCDR1 (SEQ ID NOS 53, 53, 53, 53, 53, 53, and 53) | HCDR2 (SEQ ID NOS 54, 54, 54, 54, 54, 54, 54, and 54) | HCDR3 (SEQ ID NOS 79-86) |
|---|---|---|---|---|
| mM-CSF1.3.12D6 | VH1 | YTFTSYWMH | RIDPNSGGTKYNEKFKS | SDGSTYAFAY |
| mM-CSF1.3.13A8 | VH1 | YTFTSYWMH | RIYPNSGGTKYNEKFKS | SSSYTYAFDY |
| mM-CSF1.3.13D4 | VH1 | YTFTSYWMH | RIDPNSGGTKYNEKFKS | SDSYTYAFAY |
| mM-CSF1.3.13G11 | VH1 | YTFTSYWMH | RIDPNSGGTKYNEKFKS | SYYYAFDY |
| mM-CSF1.3.14C2 | VH1 | YTFTSYWMH | RIDPNSGGTKYNEKFKS | TYYYAFDY |
| mM-CSF1.3.14D1 | VH1 | YTFTSYWMH | RIDPNSGGTKYNEKFKS | TYKYAFDY |
| mM-CSF1.3.13E10 | VH1 | YTFTSYWMH | RIDPNSGGTKYNEKFKS | STAYGYRYYFDY |
| mM-CSF1.3.14G10 | VH1 | YTFTSYWMH | RIDPNSGGTKYNEKFKS | SYKYAFDY |

Light chain

| Clone | Framework | LCDR1 (SEQ ID NOS 87, 87, 87, 87, 87, 87, and 87) | LCDR2 (SEQ ID NOS 88, 88, 88, 88, 88, 88, 88, and 88) | LCDR3 (SEQ ID NOS 89-96) |
|---|---|---|---|---|
| mM-CSF1.3.12D6 | VkB3 | RASKSVSTSGYSYMH | YLASNLESGVPARFSGS | QQYSEYPF |
| mM-CSF1.3.13A8 | VkB3 | RASKSVSTSGYSYMH | YLASNLESGVPARFSGS | QQYSSYPF |
| mM-CSF1.3.13D4 | VkB3 | RASKSVSTSGYSYMH | YLASNLESGVPARFSGS | FQYYERPH |
| mM-CSF1.3.13E10 | VkB3 | RASKSVSTSGYSYMH | YLASNLESGVPARFSGS | EQIYSFPL |
| mM-CSF1.3.13G11 | VkB3 | RASKSVSTSGYSYMH | YLASNLESGVPARFSGS | QQYYSYPF |
| mM-CSF1.3.14C2 | VkB3 | RASKSVSTSGYSYMH | YLASNLESGVPARFSGS | QQHKYPF |
| mM-CSF1.3.14D1 | VkB3 | RASKSVSTSGYSYMH | YLASNLESGVPARFSGS | QQYYEKPY |
| mM-CSF1.3.14G10 | VkB3 | RASKSVSTSGYSYMH | YLASNLESGVPARFSGS | QQYNHVPF |

TABLE 29

(selected binders from the sublibrary VH1VkB3):

Heavy chain

| Clone | HCDR1 (SEQ ID NOS 53, 53, and 53) | HCDR2 (SEQ ID NOS 54, 54, and 54) | HCDR3 (SEQ ID NOS 97-99) |
|---|---|---|---|
| mM-CSF1.3.15B8 | YTFTSYWMH | RIDPNSGGTKYNEKFKS | SYRSYMDY |
| mM-CSF1.3.15G8 | YTFTSYWMH | RIDPNSGGTKYNEKFKS | SYRSYFDY |
| mM-CSF1.3.15A10 | YTFTSYWMH | RIDPNSGGTKYNEKFKS | SYRSYFDV |

Light chain

| Clone | LCDR1 (SEQ ID NOS 87, 87, and 87) | LCDR2 (SEQ ID NOS 88, 88, and 88) | LCDR3 SEQ ID NOS 100-102) |
|---|---|---|---|
| mM-CSF1.3.15B8 | RASKSVSTSGYSYMH | YLASNLESGVPARFSGS | QQHWEYPH |
| mM-CSF1.3.15G8 | RASKSVSTSGYSYMH | YLASNLESGVPARFSGS | QQYWQYPF |
| mM-CSF1.3.15A10 | RASKSVSTSGYSYMH | YLASNLESGVPARFSGS | SQYWSYPF |

TABLE 30

(selected binders from the sublibrary VH2VkB1):

Heavy chain

| Clone | HCDR1 (SEQ ID NOS 71, 71, and 71) | HCDR2 (SEQ ID NOS 72, 72, and 72) | HCDR3 (SEQ ID NOS 103-105) |
|---|---|---|---|
| mM-CSF1.3.17F6 | FTFSSYTMSWVRQTPEKRLE | TISGGGGNTYYPDSVKG | SYYGSKYPFDY |
| mM-CSF1.3.18D8 | FTFSSYTMSWVRQTPEKRLE | TISGGGGNTYYPDSVKG | SYYGIFDY |
| mM-CSF1.3.18H4 | FTFSSYTMSWVRQTPEKRLE | TISGGGGNTYYPDSVKG | WIYYAFDY |

Light chain

| Clone | LCDR1 (SEQ ID NOS 106, 87, and 87) | LCDR2 (SEQ ID NOS 107, 88, and 88) | LCDR3 SEQ ID NOS 108-110) |
|---|---|---|---|
| mM-CSF1.3.17F6 | RSSQSIVHSNGNTYLE | YKVSNRFSGVPDRFSGS | AQRSHYPL |
| mM-CSF1.3.18D8 | RASKSVSTSGYSYMH | YLASNLESGVPARFSGS | QQEEHVPL |
| mM-CSF1.3.18H4 | RASKSVSTSGYSYMH | YLASNLESGVPARFSGS | QQYSSYPF |

TABLE 31

(selected binders from the sublibrary VH5VkB3):

Heavy chain

| Clone | HCDR1 (SEQ ID NOS 71, 71, 71, 71, 71, 71, and 71) | HCDR2 (SEQ ID NOS 72, 72, 72, 72, 72, 72, and 72) | HCDR3 (SEQ ID NOS 111-117) |
|---|---|---|---|
| mM-CSF1.3.19C9 | FTFSSYTMSWVRQTPEKRLE | TISGGGGNTYYPDSVKG | MYYSYGMTFDY |
| mM-CSF1.3.20C3 | FTFSSYTMSWVRQTPEKRLE | TISGGGGNTYYPDSVKG | MYYASGMAFDY |
| mM-CSF1.3.20D7 | FTFSSYTMSWVRQTPEKRLE | TISGGGGNTYYPDSVKG | YRYGSGYYFDY |
| mM-CSF1.3.20F1 | FTFSSYTMSWVRQTPEKRLE | TISGGGGNTYYPDSVKG | YTYSMGYYFDY |
| mM-CSF1.3.20F9 | FTFSSYTMSWVRQTPEKRLE | TISGGGGNTYYPDSVKG | RYYDNLTFAV |
| mM-CSF1.3.20A6 | FTFSSYTMSWVRQTPEKRLE | TISGGGGNTYYPDSVKG | SGYGYYFAY |
| mM-CSF1.3.20A12 | FTFSSYTMSWVRQTPEKRLE | TISGGGGNTYYPDSVKG | TSSSFWYAFDY |

Light chain

| Clone | LCDR1 (SEQ ID NOS 87, 87, 87, 87, 87, 62, and 62) | LCDR2 (SEQ ID NOS 88, 88, 88, 88, 88, 63, and 63) | LCDR3 (SEQ ID NOS 118-124) |
|---|---|---|---|
| mM-CSF1.3.19C9 | RASKSVSTSGYSYMH | YLASNLESGVPARFSGS | QQDDHYPY |
| mM-CSF1.3.20C3 | RASKSVSTSGYSYMH | YLASNLESGVPARFSGS | QQDNEYPY |
| mM-CSF1.3.20D7 | RASKSVSTSGYSYMH | YLASNLESGVPARFSGS | QQGSHYPR |
| mM-CSF1.3.20F1 | RASKSVSTSGYSYMH | YLASNLESGVPARFSGS | QQGSHYPR |
| mM-CSF1.3.20F9 | RASKSVSTSGYSYMH | YLASNLESGVPARFSGS | QQEEEWPD |
| mM-CSF1.3.20A6 | KASQSVDYDGDSYMN | YAASNLESGIPARFSGS | SQRSHYPQ |
| mM-CSF1.3.20A12 | KASQSVDYDGDSYMN | YAASNLESGIPARFSGS | QQLYSYPK |

Figure 32:
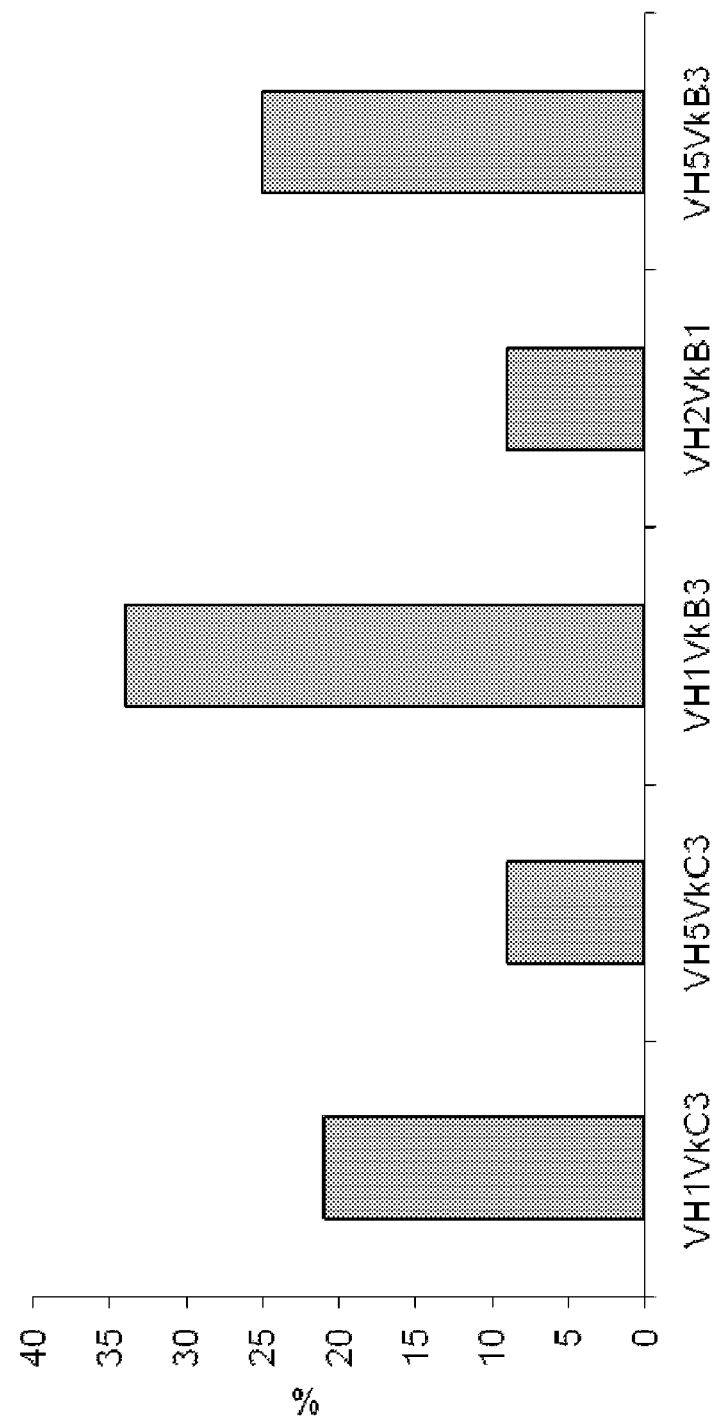
FIG. 32 shows diversity and abundance of different frameworks combinations isolated from a test panning with the murine library of the present invention.

A diversity of different frameworks combinations was isolated from the panning with the full library, with the most abundant binders comprising a VH1VkB3 combination. FIG. 32 shows an overview of the combinations identified.

Expression of Fab Antibody Fragment

First, a preculture (10 ml) of fresh transformed binders in *E. coli* TG1 F– in expression vector pMORPHx9_FH was inoculated in 2×YT/Cm/1% Glu medium and incubated for 3-5 h at 30° C. After that, 500 ml 2×TY/Cm/0.1% Glu medium with the whole volume of preculture was inoculated and incubated at 30° C. in a shaker at 200 rpm until an OD600 nm of 0.5 was reached. IPTG (1 M) was added to a final concentration of 0.75 mM for the induction of expression (375 µl/500 ml culture). The Fabs were expressed at 30° C., O/N shaking at 200 rpm. The next day, the bacteria were spun down at ~4000 g for 30 min at 4° C. and the pellets were frozen at 20° C. for at least O/N.

Purification Using IMAC and SEC

Figure 33:
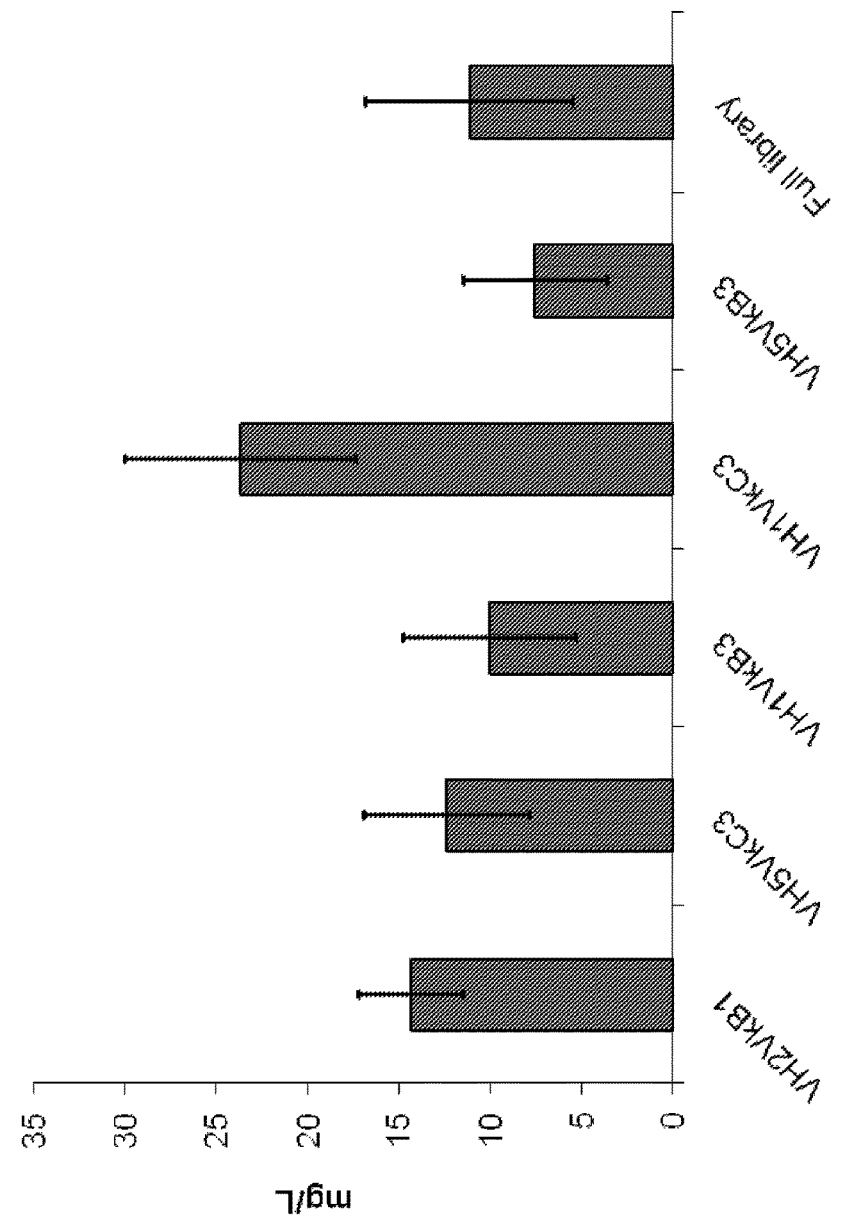
FIG. 33 shows an overview of the obtained yields of mM-CSF specific Fab fragments after expression and purification from bacterial cells.

Bacterial pellets were resuspended in Lysis Buffer comprising 25 mM Tris pH8.0, 0.5 M NaCl, 0.1% Lysozyme, 2 mM MgCl$_2$ and 10 U/ml Benzonase. After incubation the supernatant was filtered through a 0.2 µm filter. IMAC Purification of Fab with His6-Tag (SEQ ID NO: 1) using Aekta Express was applied for fully automated purification at room temperature 20° C.: filtered samples were loaded on an IMAC column (HiTrap 1 ml Chelating HP), washed with 20 mM Na-Phosphatbuffer pH7.4, 500 mM NaC, 20 mM Imidazole, and eluted with 250 mM Imidazol/20 mM Na-Phosphatbuffer/500 mM NaCl, pH7.4. The eluted peaks were applied on a gel filtration column (HiLoad 16/60 Superdex 75) and the purified protein were eluted into a deepwell plate in PBS. FIG. 33 shows an overview of the obtained expression yields of mM-CSF specific Fab fragments.

Affinity Constants Determination by ELISA

Wells of a microtiter plate were coated with 1 µg/ml mM-CSF in PBS, 50 µL/well, o/n at 4° C. After washing the wells were blocked with 350-400 µL 5% MTBST for 2 h at RT. In the meantime dilutions of each purified Fab for test were prepared: 1000/100/10/1/0.1/0.01 nM concentration (in duplicates). The blocked ELISA microtiter plates was washed once with TBST. After that 50 µL of the prepared dilutions of purified Fabs were transferred in the corresponding wells of the ELISA plates.

Figure 34:
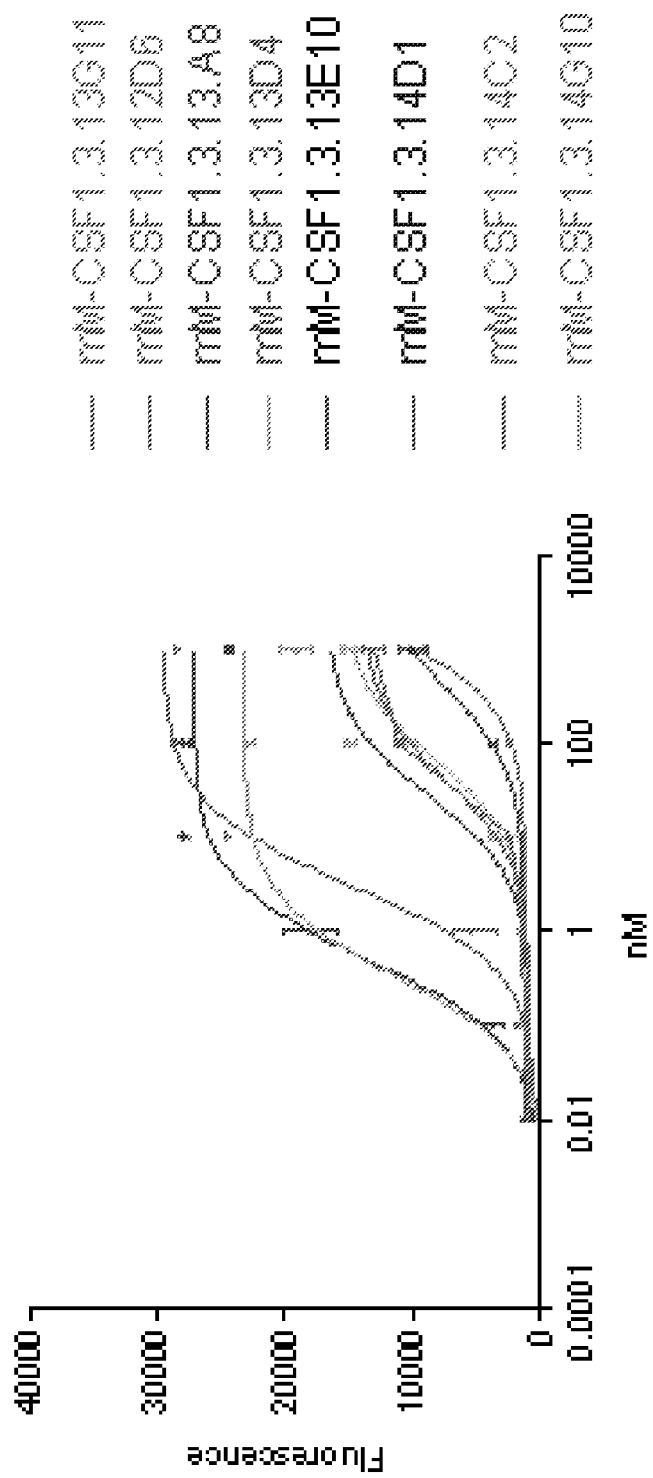
FIG. 34 shows the results of the determination of the affinity constants for some mM-CSF specific Fab fragments as determined in an ELISA assay.

NK1: Coating with selection antigen, +blocking, +PBS, –secondary conjugated antibody +substrate NK2: Coating with PBS, +blocking, +PBS, +PBS, +secondary conjugated antibody, +substrate NK3: Coating with selection antigen, +blocking, +PBS, +secondary conjugated antibody, +substrate The ELISA plates were incubated with protein dilutions for 2 h at RT on a microtiter plate shaker, washed 3× quickly with TBST and 100 µL goat anti-mouse Fab antibody-AP conjugate (diluted 1:5000 in MTBST) was added and incubated for 1 h at RT shaking gently. The plate was washed 3× quickly with TBST and add 100 µL AttoPhos substrate (1:5) was added to each well and measurement of Fluorescence (ELISA Reader) was taken. Data were analysed using a 4-parameter fit. FIG. 34 shows the results for some mM-CSF specific Fab fragments. Over 30% of the Fabs isolated have an EC50 value in the range of 1-10 nM, 17% of the Fabs in the range of 100-1000 nM, 15% in the range of 10-100 nM and 7% in the picomolar range.

Fab Conversion and Expression and Purification of a mIgG2

One of the Fab antibody fragments which bound to murine M-CSF and which showed binding activity in an ELISA was converted into murine IgG2a format by cloning of the respective VH and VL sequences into an appropriate eukaryotic expression vector harboring the respective constant light chain and murine gamma 2a chain. This expression vector was used for transfection of HEK-293 cells. IgG2a antibodies were subsequently purified from HEK293 cell culture supernatants by Protein A affinity chromatography on an Äkta system.

Affinity Determination of a Murine IgG2a Antibody by BiaCore

Binding of mouse anti-mM-CSF antibody as mIgG2a sub-type was measured towards immobilized mM-CSF. For this HBS-EP as running buffer at 30 µl/min was used at 20° C. and antibody was diluted in running buffer to following concentrations: 10, 5, 2.5, 1, 0.5 nM. Following cycle set-up was chosen: association for 180 sec, dissociation of 900 sec, regeneration of 30 sec using 10 mM glycine pH 2.0 at 30 µl/min and a final stabilization of 60 sec. All concentrations were measured in duplicates and reference subtracted (blank channel 1). Sensograms were fitted using a "bivalent ligand" binding model and constants are shown in table 32.

TABLE 32

| Ligand | ka (1/Ms) | SE (ka) | kd (1/s) | SE (kd) | Rmax (RU) | KD (M) | tc | SE (tc) | Chi$^2$ (RU$^2$) |
|---|---|---|---|---|---|---|---|---|---|
| mM-CSF | 2.83E+05 | 1.3E+03 | <E−06 | <E−08 | local | <E−12 | 1.41E+09 | 1.5E+07 | 4.5 |

Example 1.8

Test Panning with the Murine Library

Murine GM-CSF (granulocyte macrophage colony stimulation factor) was used as antigen for an another test panning. Panning, selection and characterization of the binder was essentially identical to Example 1.7 herein above, except that GM-CSF was used instead of M-CSF.

One of the Fab antibody fragments which bound to murine GM-CSF and which exhibited activity in an FDCP-1 proliferation assay was converted into murine IgG2a format by cloning of the respective VH and VL sequences into an appropriate eukaryotic expression vector harboring the respective constant light chain and murine gamma 2a chain. This expression vector was used for transfection of HKB11 cells. IgG2a antibodies were subsequently purified from HKB11 cell culture supernatants by Protein A affinity chromatography. The Fab fragment and the murine IgG2a antibody were then comparatively tested in a FDCP-1 proliferation assay. Briefly murine cell line FDCP-1 proliferates in the presence of murine GM-CSF. Different dilutions of the anti-murine-GM-CSF IgG2a or Fab were added to wells containing FDCP-1 cells and murine GM-CSF. After and incubation for 72 h (37° C.; 5% CO2) cell viability was measured by adding XTT reagent (Roche) according to the manufacturer's recommendation.

Figure 46:
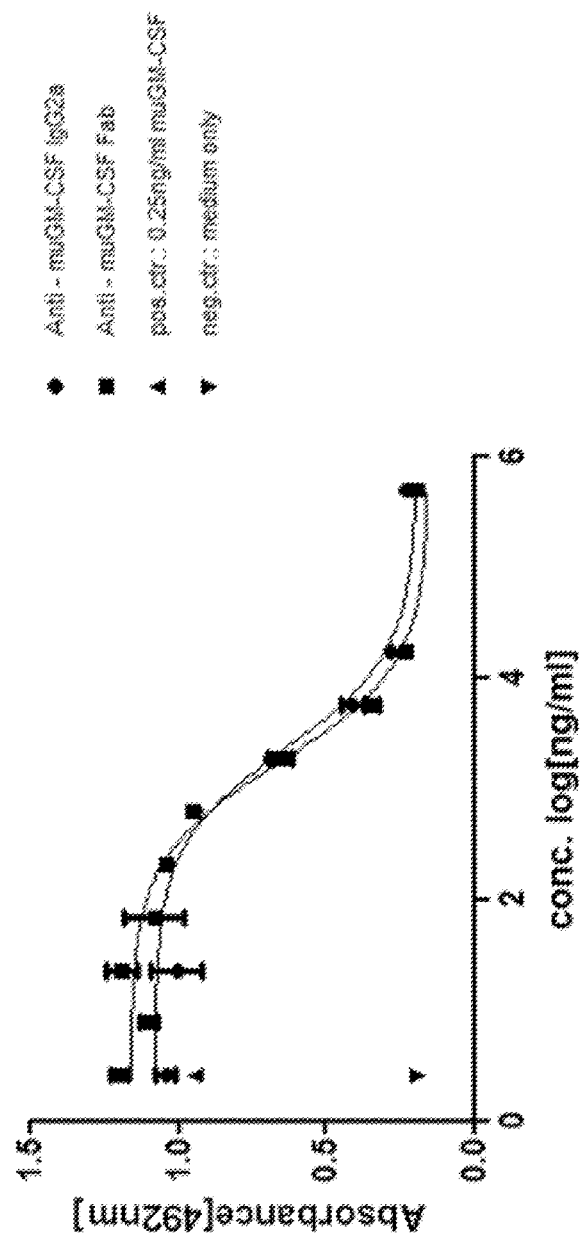
FIG. 46 demonstrates that binders isolated from the murine library of the present invention maintain their functional activity after conversion from Fab format into full length immunoglobulin format.

Results are shown in FIG. 46. Both binders were active in the assay with comparable efficacy, thereby demonstrating that functional binders can be isolated from the library, which also preserve their activity after conversion into full length immunoglobulin format.

Example 2

Generation of a Rat Antibody Library (HuCAL RAT)

Example 2.1

Design of the Rat Antibody Master Genes

Since no data were published about the usage of rat VH- or VL germline-families, all public available rat antibody sequences (498 sequences in total) were subjected to analysis. Sequences were classified into germline families by comparison of the re-arranged sequences to the germline genes. In total 498 re-arranged rat VH sequences were compared to 119 rat germline genes extracted from IMGT. The position-dependent amino-acid usage of each re-arranged sequence was compared to the amino-acid usage of each germline gene of the strain Rattus norvegicus. By doing so, each re-arranged sequence got assigned a nearest germline gene, leading to following distribution (Table 33):

TABLE 33

| | |
|---|---|
| VH1 | 48 |
| VH2 | 25 |
| VH3 | |
| VH4 | |
| VH5 | 415 |
| VH6 | 3 |
| VH7 | 4 |
| VH8 | |
| VH9 | |
| VH10 | 1 |
| VH11 | 2 |
| SUM | 498 |

Further analysis for the identification of the VH master-genes within the germline genes was done exclusively for the VH germline-families which include an reasonable amount of re-arranged sequences of VH1 and VH5.

Two approaches were taken for selection of the most frequent used germline genes, which are to be used as master genes:

a) Identification of the most prominent germline gene within the respective germline families b) Identification of the germline gene, which is most akin to the consensus of all germline-genes within one family.

Ideally, both approaches would result in the same germline gene.

Example 2.1.1

Identification of the Most Prominent VH Germline Gene within the Respective Germline Families The position-dependent amino acid present in each re-arranged sequence was compared with the amino acid present in the rat germline genes in order to identify the most frequent used germline genes. Each of the re-arranged sequences got assigned a nearest rat germline-gene. If two or more germline genes were identified as nearest germline gene for a re-arranged sequence, all germline-genes were considered as nearest germline genes. For calculation of the preferably used germline gene within a family the usage of each germline gene was summed up.

The results for the preferred germline genes within a family were not as clear as for the selection of the mouse germline-gene. The following germline genes are the two most prominent ones in the different VH-families (Table 34):

TABLE 34

| Germ-line-family | Name of prominent germline-gene | # re-arranged se-quences | % of prominent germline-gene in-arranged sequences |
|---|---|---|---|
| VH1 | AABR03048898\|IGHV1S15*01 | 48 | 10 |
| VH1 | >AABR03050300\|IGHV1S23*01 | 48 | 10 |
| VH5 | AABR03048730\|IGHV5S45*01 | 415 | 16 |
| VH5 | AABR03048499\|IGHV5S23*01 | 415 | 14 |

Example 2.1.2

Identification of the Germline Gene, which is Most Similar to the Consensus of all Germline Genes within One Family The consensus germline sequences of 25 single VH1 and 21 single VH5 germline genes were prepared.

Consensus_of All VH1 Germline-Genes:

(SEQ ID NOS 125-127)
QVQLQQSGAELVKPGASVKISCKASGYTFTSYYMH . . .

WVKQRPGQGLEWIGYIYPGS . . . GGTNYNEKF

KGKATLTVDKSSSTAYMQLSSLTSEDSAVYYCAR

Consensus_of All VH5 Germline-Genes:

(SEQ IS NOS 128-130)
EVQLVESGGGLVQPGRSLKLSCAASGFTFSNYGMA . . .

WVRQAPTKGLEWVASISTDG . . . SSTYYRDSV

KGRFTISRDNAKSTLYLQMDSLRSEDTATYYCAR

These consensus sequences were compared against each individual germline gene of the VH1 family and the VH5 family, respectively, and the individual germline genes were evaluated in respect of identity to the consensus sequence (Table 35).

TABLE 35

| Germline-family | Name of prominent germline-gene | # deviations to consensus [aa] |
|---|---|---|
| VH1 | >AABR03050300\|IGHV1S23*01 | 11 (of 98 aa) |
| VH5 | AABR03048730\|IGHV5S45*01 | 2 (of 98 aa) |

This result was confirmed by BLAST analyses of the consensus sequences against all germline genes.

Example 2.1.3

Compilation of a Rat VL Mastergene

Kappa light chains constitute a majority of rat light chains, being found in 90% of pooled light chains isolated from laboratory rats (Frank and Gutman, 1988, *Mol Immunol* 25, 953-960). Since no VL germline sequences, and only a limited set of re-arranged sequences, were available a different approach was taken for the development of a rat VL mastergene. The 44 sequences available were grouped according to the length of the LCDR1, followed by formation of consensus sequences.

Figure 35:
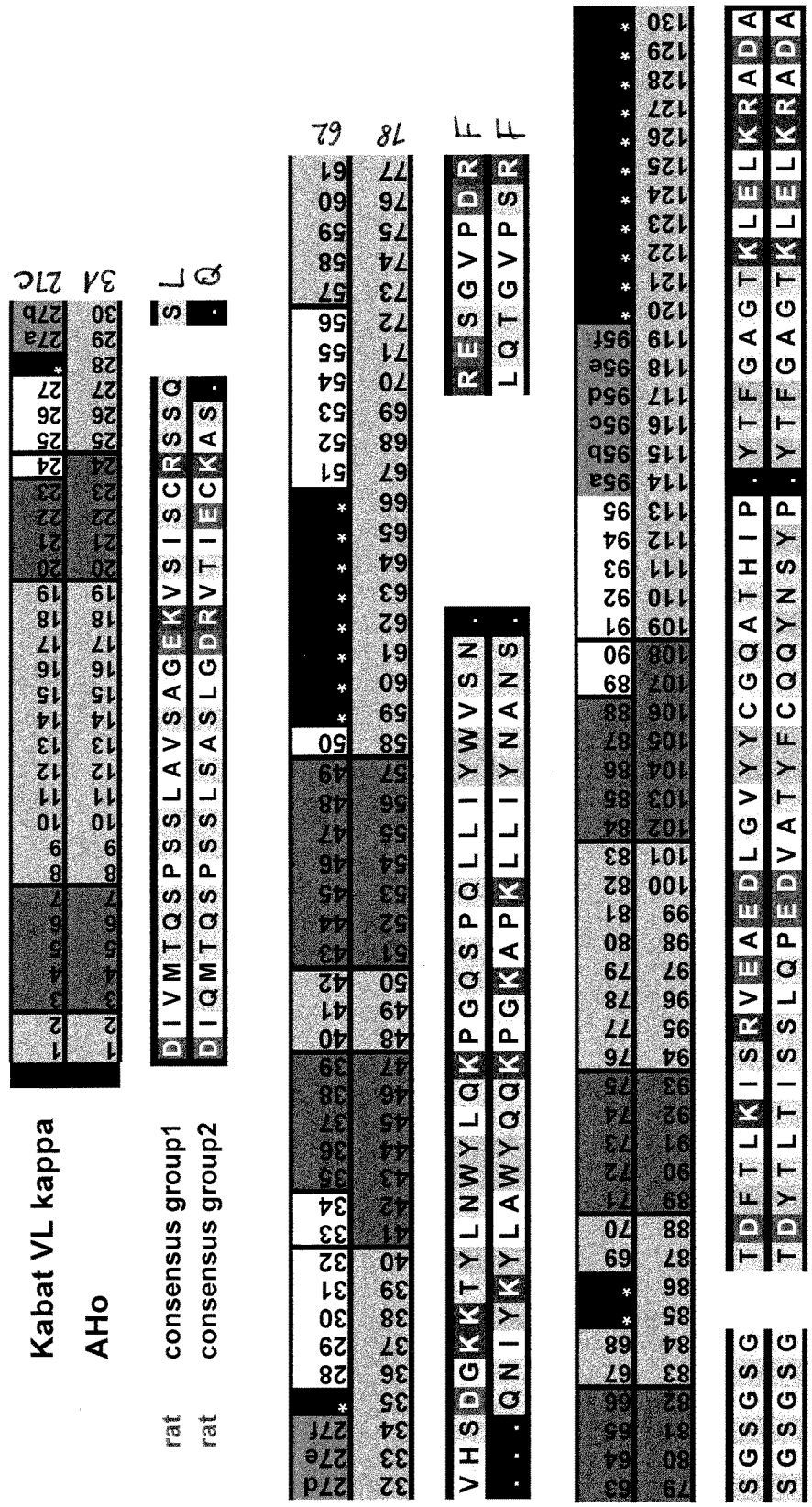
FIG. 35 shows the design of the two groups of rat VL mastergenes (SEQ ID NOS 195-196, respectively, in order of appearance)
Figure 37:
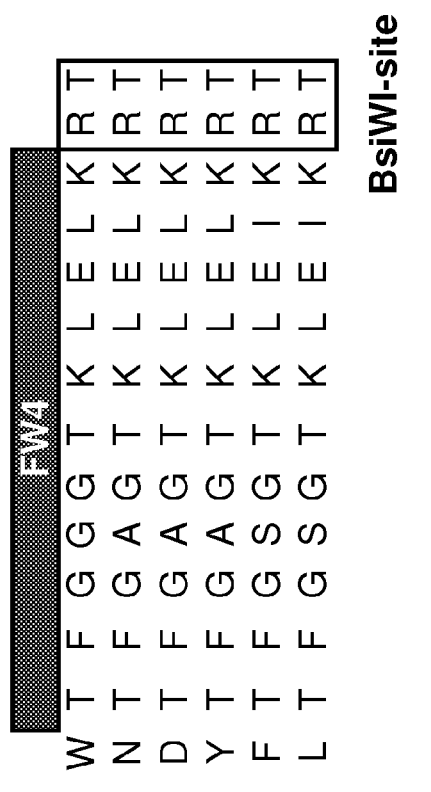
FIG. 37 shows framework 4 region of the rat VL mastergene (SEQ ID NOS 201-206, respectively, in order of appearance)

The consensus sequences of a first group (LCDR1-length=17aa, number of sequences=11) and of a second group (LCDR1-length=11aa, number of sequences=33) were used as rat VL mastergenes in the library. See FIG. 35.

Example 2.1.4

Summary

No modifications of the germline genes (for VH) or the consensus-sequence (for VL) were required for modularity reasons, since all required restriction sites were already present in the selected genes. Table 36 summarizes the nearest germline genes for the mastergenes selected:

TABLE 36

| MG | Name of nearest germline-gene |
|---|---|
| rVH1 | IGHV1S23*01 |
| rVH5 | IGHV5S45*01 |
| rVL1 | consensus-sequence1 |
| rVL2 | consensus-sequence2 |

For completion of the rVH germline genes to full length mastergenes, antibody framework 4 was added to the sequences. IMGT provides access to rat J-regions, which form antibody framework 4 in antibody-development. J-region JH2 (sequence WGQGVMVTVSS) (SEQ ID NO: 131) was selected for complementation of the VH-mastergene, since it was frequently found in rearranged antibodies deposited in the IMGT database. In addition JH2 provides al required RE-sites (StyI and BlpI). See FIG. 36.

For completion of the rVL to a full length mastergene, J-regions Jκ2-3 was selected, since Tyr was found most frequently in the set of re-arranged sequences, which were used for analysis. The last amino acids of framework 4 (RT) were added to include a BsiWI-site. See FIG. 27.

Example 2.2

Design of Rat CDRs

Design of L-CDR3 and H-CDR3 Library Cassettes
Design of H-CDR2 Maturation Cassette Overview of the synthesized master genes encoding variable domain is presented in FIG. 21. Kabat numbering indicates position of an amino acid residue in a VL- or VH-sequences. rVL denotes rat variable domain in the light chain (exclusively of the type kappa), and rVH denotes rat variable domain in the heavy chain. The two rat Vκ consensus sequences rVL1 and VL2 encode VL starting from position 1 (at the N-terminus of framework 1) to 95 (at the C-terminus of L-CDR3). Rat Jκ germ-line genes encode for the very C-terminal residue in L-CDR3 (constant position 96) and whole framework 4 in rVL (positions 97-108). We have chosen rat Jκ2 (Burstein et al., 1982, Proc Natl Acad Sci U.S.A. 79, 5993-5997), since Tyr is the most frequent residue in position 96 of rearranged antibodies found in the IMGT database.

Rat VH germ-line genes encode rVH starting from position 1 (at the N-terminus of framework 1) to 94 (at the very C-terminus of framework 3). H-CDR3 sequence is encoded by the D germ-line genes. We reasoned that biochemical and biophysical properties of the VH-domain depend also on its HCDR3 sequence, and therefore for the purpose of the master-gene comparison we decided introducing a particular HCDR3 sequence derived from antibody 4D5 into the both rVH master-genes (see below). Rat JH germ-line genes encode for a C-terminal part of HCDR3 and whole framework 4 (positions 103-113). We have chosen rat JH2 (sequence WGQGVMVTVSS) (SEQ ID NO: 131) for the design of framework 4 because JH2 was frequently found in rearranged antibodies deposited in the IMGT database, and it allowed us to introduce two restriction endonuclease sites (StyI and BlpI) indispensable for the HuCAL cloning modularity.

In order to comply with the essential requirements of the HuCAL® cloning-modularity, the amino acid sequence corresponding to positions 1-4 in both rVHs was fixed to EVQL (SEQ ID NO: 50).

Example 2.3

Cloning, Expression and Purification of the Rat Library

Bacterial Strains and Vectors Used for Cloning

As described above for the murine library, molecular cloning was carried out using the *E. coli* strains XL1-Blue (Stratagene) or Top10F+ (Invitrogen). The products from gene synthesis (master-genes) were first cloned into a pGA-vector at GeneArt AG, and then re-cloned into tricistronic CysDisplay pMorph30-vector as described below. Phage display vector pMorph30 was derived from plasmid pMorph23 (Rothe et al., 2008, *J Mol Biol* 376, 1182-1200) basically as follows: hexa-His-tag (SEQ ID NO: 1) attached at the C-terminus of VH was replaced for AA-sequence HKHKHK (SEQ ID NO: 2), and a chi site in gIII was eliminated. Restriction endonucleases were from New England Biolabs or Fermentas, and T4 DNA ligase was from Invitrogen. Reaction conditions were carried out according to the manufacturer's recommendations.

Gene Construction

IMGT *Rattus norvegicus* sub-database-/NCBI-accession numbers of germ-line sequences which were used for construction of the master-genes:
rVH1: IGHV1S23*01/AABR03050300, rVH5: IGHV5S45*01/AABR03048730, Jκ2: IGKJ2-3*01/J00746, JH2: IGHJ2*01/X56791, Cκ:☐IGKC*01/V01241, CH1+hinge: IGHG1*01/AABR03048905.

Considerations for the Synthesis of Master-Genes

As described above, genes corresponding to the selected representative germ-line sequences (accession numbers are given below) were optimized on DNA level by applying following criteria: (i) rare codon usage preferably is optimal for *E. coli* while human/murine rare codons should be avoided whenever possible; (ii) undesirable DNA/RNA features such as internal TATA-boxes, chi-sites, ribosomal entry sites, AT-rich or GC-rich sequence stretches, sequences preventing mRNA-transport into cytoplasm (INS or CRS elements), repeat sequences, RNA secondary structures, and cryptic splice donor and acceptor sites preferably are avoided; (iii) introduction of restriction endonuclease (RE) sites conflicting with the HuCAL® cloning-modularity were avoided; and (iv) restriction endonuclease sites required for the modular cloning were introduced. Glycosylation in variable domains is undesirable mainly because the carbohydrate-attachment is often found to affect binding of antigen due to steric hindrance, and is also responsible for heterogeneity of proteins expressed in eukaryotic hosts. Hence we ascertained that the designed VL/VH-master-genes did not encode for protein with potential sites for N-linked glycosylation.

Constant Domains in Fab Format

Constant domain of the kappa light chain is encoded by Cκ gene. N-terminal Ala-residue was replaced by Thr which allows introduction of the BsiWI site at this position on the DNA level. A cysteine residue which is located in the C-terminus of Cκ and is normally involved in formation of the disulfide bond linking the light and heavy chains in natural Fab- or IgG-molecules was replaces for Ala. Since the C-terminal "free" Cys-residue was removed, the light and heavy chains are no longer covalently linked together in our modified Fab format. This modification is the main feature of the CysDisplay® which allows for selective elution of bound phages (Rothe et al., 2008, *J Mol Biol* 376, 1182-1200).

Constant domain of the heavy chain in Fab format is encoded by CH1 gene-fragment. We have chosen germ-line gene IGHG1*01 which more resembles CH1-sequence in a successful rat therapeutic anti-CD52 antibody CAMPATH-1 (Cheetham et al., 1998, *J Mol Biol* 284, 85-99). Addition of one Ala-residue in front of the N-terminal sequence ETTAPS (SEQ ID NO: 132) allowed us introduction of the BlpI site. First three residues of the hinge (sequence PRD) followed by residues Glu-Phe needed for introduction of EcoRI site were added at the C-terminus of the CH1 domain.

Gene Assembly in Tricistronic Phage Display Plasmid

The designed genes encoding for rat constant or variable domains were generated by PCR-assembly of a series of synthesized oligonucleotides, and cloned into an interim pGA vector at GeneArt AG. It was convenient and faster to replace human VL, VH, Ck and CH1 genes for rat equivalents in two different interim vector molecules. Derivatives of the pMorph30 plasmid (Rothe et al., 2008, *J Mol Biol* 376, 1182-1200), designated as "plasmid L" and "plasmid H", were constructed with relatively large fragment of dummy DNA in order to facilitate cloning as follows: in "plasmid L", dummy DNA (~3 kb) was incorporated in place of light chain-coding region, whereas in "plasmid H", dummy DNA (about 2 kb) was present in place of heavy chain-coding region. Dummy DNA in "plasmid L" was replaced in two steps: rCκ gene (see above) was inserted into the vector by using BsiWI/SphI, and then rVL kappa master-genes (see above) were inserted into the vector by using EcoRV/BsiWI. Dummy DNA in "plasmid H" was also replaced in two steps: rCH1 gene (see above) was inserted into the vector by using StyI (or Eco130I)/EcoRI, and then rVH master-genes (see above) were inserted into the vector by using MfeI/StyI. Two DNA fragments encoding master-genes rVH1 or rVH5 (both linked to mCH1-region) were excised from the "plasmid H", and inserted by using SphI/HindIII into a panel of "plasmid L" plasmids encoding a variety of rVL master-genes resulting in 4 rVL-rVH combinations. The tricistronic "plasmid L" encoding for gpIII, rVL/rCκ□ also and rVH/rCH1 was denominated as pMorph32 indicating the fact that the plasmid encodes rat variable and constant domains.

Re-Cloning of Rat VL-VH Master Gene Combinations into Bicistronic pMorphx9_Fab_FH Vector for Expression in *E. coli*

As described above, in order to analyze soluble expression of VL-VH framework combinations in Fab format, we have re-cloned by using XbaI and EcoRI all four VL-VH master-gene combinations (as Fab-encoding inserts) into pMorphx9_Fab_FH vector (Rauchenberger et al., 2003, *J. Biol. Chem.* 278, 38194-38205) where FH indicates that the Flag– and hexa-His-tags (SEQ ID NO: 1) were attached C-terminally to the Fab.

Conversion of rVL-rVH Master Gene Combinations to Rat IgG2b and 2c Formats

In order to analyze expression of master-gene combinations in full-length rat kappa IgG2b and 2c formats in mammalian cells, we have subcloned the four rVL-rVH master gene combinations into pMorph2_h/r_IgG vector which is a derivative of pMorph2_h_IgG vector (Steidl et al. 2008. *Mol Immunol* 46(1):135-44). Transcription is driven in this plasmid by CMV-promoter.

Expression and Purification of Fab

As described in the case of mouse, expression in *E. coli* TG1-cells from the pMx9_Fab_FH plasmid was carried out in 500 ml of 2×YT-medium supplemented with chloramphenicol (34 μg/ml) and glucose (0.1%). After induction with IPTG (0.75 mM), the cells were grown at 30° C. for 20 h. Cell pellets were lysed during incubation with lysis buffer (200 mM sodium phosphate, pH 7.4, 0.5 M NaCl, 10 mM imidazol, 0.2% lysozyme, 2 mM $MgCl_2$, 20 U/ml benzonase and EDTA-free protease inhibitor cocktail from Roche) for 30 min at RT. Fab-purification from cleared cell lyzates was carried out by IMAC with $Ni^{2+}$ ions. After elution, imidazol-containing buffer was replaced for PBS on the PD10 desalting columns (Amersham Pharmacia Biotech).

Expression and Purification of IgG

Also, as described above, eukaryotic HKB11 cells were transiently transfected with the pMorph4_h/m_IgG plasmid encoding the heavy and light chains. Cell culture supernatant was harvested from 3 to 7 days post transfection. After adjusting the pH of the supernatant to 8.0, addition of NaCl (2 M final concentration) and sterile filtration (0.45 μm), the solution was subjected to standard protein A affinity chromatography (MabSelect SURE, GE Healthcare). If not stated otherwise, buffer exchange was performed to 1× Dulbcecco's PBS (pH 7.2, Invitrogen) and samples were sterile filtered (0.2 μm). Purity of IgG was analysed under denaturing conditions by SDS-PAGE or by using Agilent BioAnalyzer and in native state by HP-SEC.

Phage Preparation

Phage amplification and purification was carried out essentially as described previously (Krebs et al., 2001, *J Immunol Methods* 254, 67-84) with a following modification. Phagemids (VL-VH framework combinations encoded in display plasmid) were propagated in *E. coli* Top10F+ cells in 2×YT/Cam/Tet/glucose (1%) medium. After helper phage infection (hyperphage from Progen, Cat. No.: PRHYPE, multiplicity of infection: 40), centrifugation and resuspension of the cell pellet in 2×YT/Cam/Kan/Tet/IPTG (0.25 mM), phages were produced during 20 h incubation at 22° C.

Phage Display Sandwich ELISA

Black Maxisorp microtiter plates (Nunc) were coated with anti-pIII antibody (MoBiTec, Cat. No.: PSKAN3) for determination of relative pIII-level (≈phage concentration), or with anti rat F(ab')$_2$ antibody (Jackson ImmunoResearch Lab.; Cat. No.: 112-006-072) for determination of relative Fab-level in phage samples. Although the exact epitope of the anti rat F(ab')$_2$ antibody is not known (it is presumed to be located in the constant domain), we reasoned that binding of the antibody to rat Fab is not likely to be strongly affected by sequence-variation in Fv-domain, and thus the antibody should be suitable for general assessment of rat Fab-display on tip of filamentous phage. TBS pH 7.4 with Tween 20 (0.05%) and chemi-blocker (from Chemicon; diluted 1:2) was used for blocking of non-specific binding sites in the plate and on phages. After incubation with phages, wells were washed with TBS-T, and incubated sequentially with biotinylated anti-bacteriophage antibody (Sigma Cat. No. B2661) and avidin-HRP (BD Pharmingen; Cat. No.: 554058). "Quanta Blu" substrate for HRP was applied, and fluorescence signals were recorded on Tecan-Spectrafluor instrument (excitation: 320 nm, emission: 430 nm). The relative pill- and Fab-levels in phage sample were determined by using reference phage (displaying a previously selected HuCAL Fab converted into rat format) and the standard 2-state model applied for non-linear regression. The relative display rate was defined as a ratio of the Fab- and pill-levels.

Example 2.4

Characterization of the Rat Antibody Library by Way of Exemplary Antibody 4D5

We reasoned that good presentation on phages and high expression in cells can be achieved only for well folded and stable Fab-molecules. It is known that thermodynamic stability of Fab-molecule depends on intrinsic stability of the individual domains (heavy and light chains) as well as on non-covalent interaction between the two domains (Ewert et al., 2003, *J Mol Biol* 325, 531-553). Tight interaction between Fd (heavy chain) and Cκ (light chain) are of particular importance because in the CysDisplay® system the two domains cannot be covalently linked via disulfide bond since cysteine residue in the C-termini of constant domains was eliminated. Therefore, instead of testing VL- and VH-frameworks individually, we sought to identify VL-VH combinations which could be efficiently folded and expressed in *E. coli* (Fab format) and in mammalian cells (IgG format).

As a test case we used the HCDR3 sequence of antibody 4D5 (WGGDGFYAMDY) (SEQ ID NO: 6). This sequence had already been used previously for the assessment of human master-genes prior the construction of the original HuCAL library (Knappik et al., 2000, *J Mol Biol* 296, 57-86).

Analysis of Display Efficiency

Figure 38:
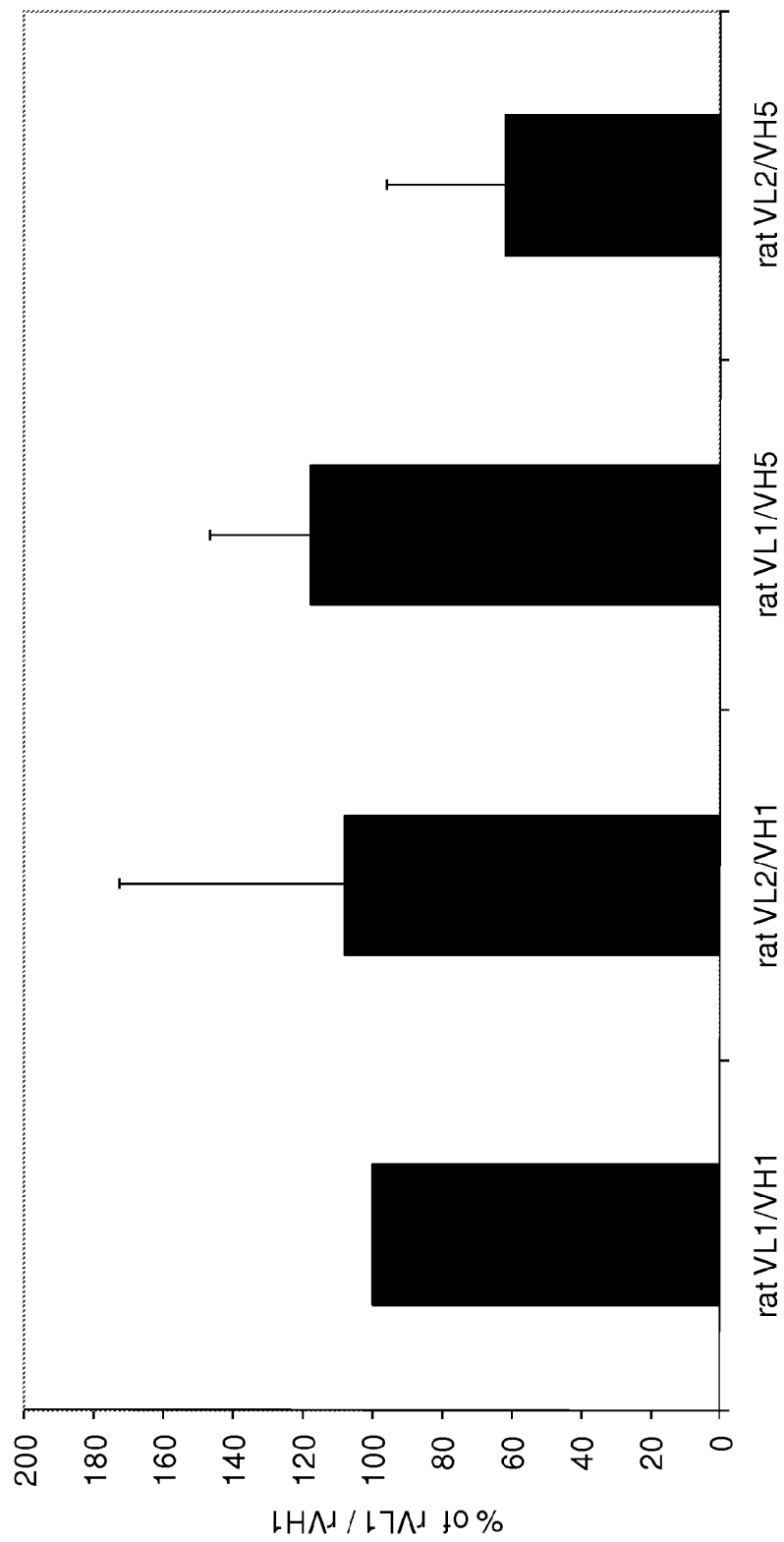
FIG. 38 shows display of rat mastergenes in Fab-format on filamentous phage. All four tested rVL-rVH framework combinations were clearly displayed on phages.

Since efficient display of library members on phage particles is a prerequisite for successful outcome from phage display selections, we decided to use sandwich phage ELISA quantification of display for four rat VL-VH combinations in Fab-format. Our data indicate that all four tested rVL-rVH framework combinations were clearly displayed on phages (FIG. 38).

Soluble Fab Expression

Figure 39:
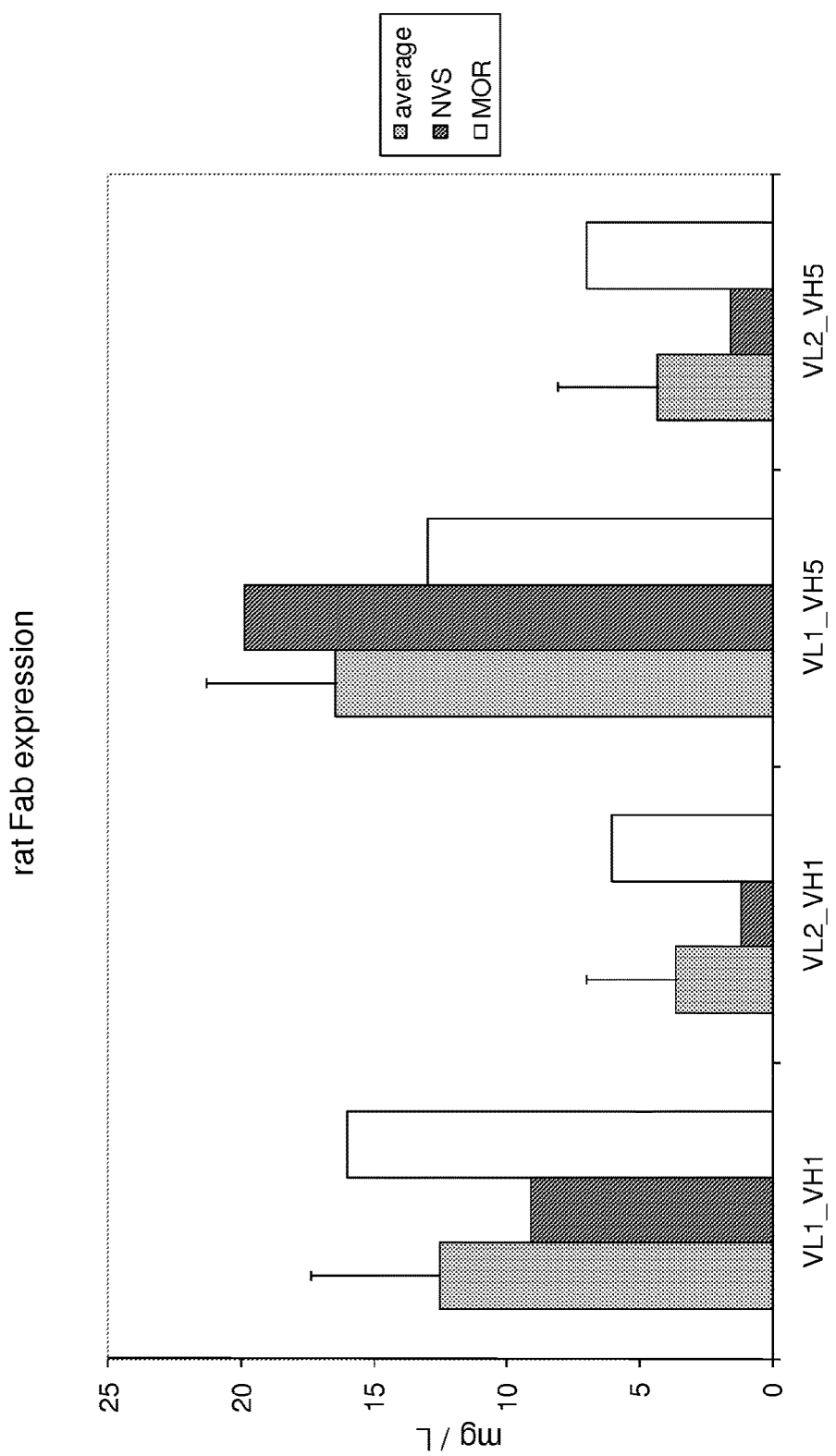
FIG. 39 depicts soluble expression of the rat mastergenes in Fab-format. The rVL1-combinations expressed particularly well. Shown are results from two individual experiments (labeled as "NVS" and "MOR"), as well as the average of these two experiments.

Also soluble expression of the four rat VL-VH combinations in Fab format was tested in *E. coli*. We found that the VL1-combinations with VH1 or VH5 were expressed surprisingly at 3-4-fold higher levels than the VL2-combinations (FIG. 39). The expression level of VL1-VH5 was remarkably high (about 15 mg/L), and led finally to our decision to choose this Fv as the framework for the construction of the rat library.

Soluble IgG-Expression

Due to the fact that at present the most successful antibody format approved for human therapy is IgG we decided to characterize expression of the four rat VL-VH mastergene combinations also in IgG format. Two distinct rat IgG formats, IgG2b and 2c, were chosen for the expression test. Whereas rat gamma heavy chain γ1 and γ2a share 94% sequence homology, and best resemble mouse γ1, rat γ2b is equivalent to the mouse γ2a/γ2b pair as regards both nucleotide sequence and antibody effector functions (strong complement activation and binding to FcγR) whilst rat γ2c resembles mouse γ3 (high sequence homology) and weakly activates complement (Bruggemann, 1988, *Gene* 74, 473-482). Rat IgG2b binds poorly to proteins A and G under low (physiological) ionic strength. In contrary, rat IgG2c binds strongly to proteins A and G; nevertheless is poorly soluble in solutions of low ionic strength (Rousseaux and Bazin, 1979, *Vet Immunol Immunopathol.* 1, 61-78).

Figure 40:
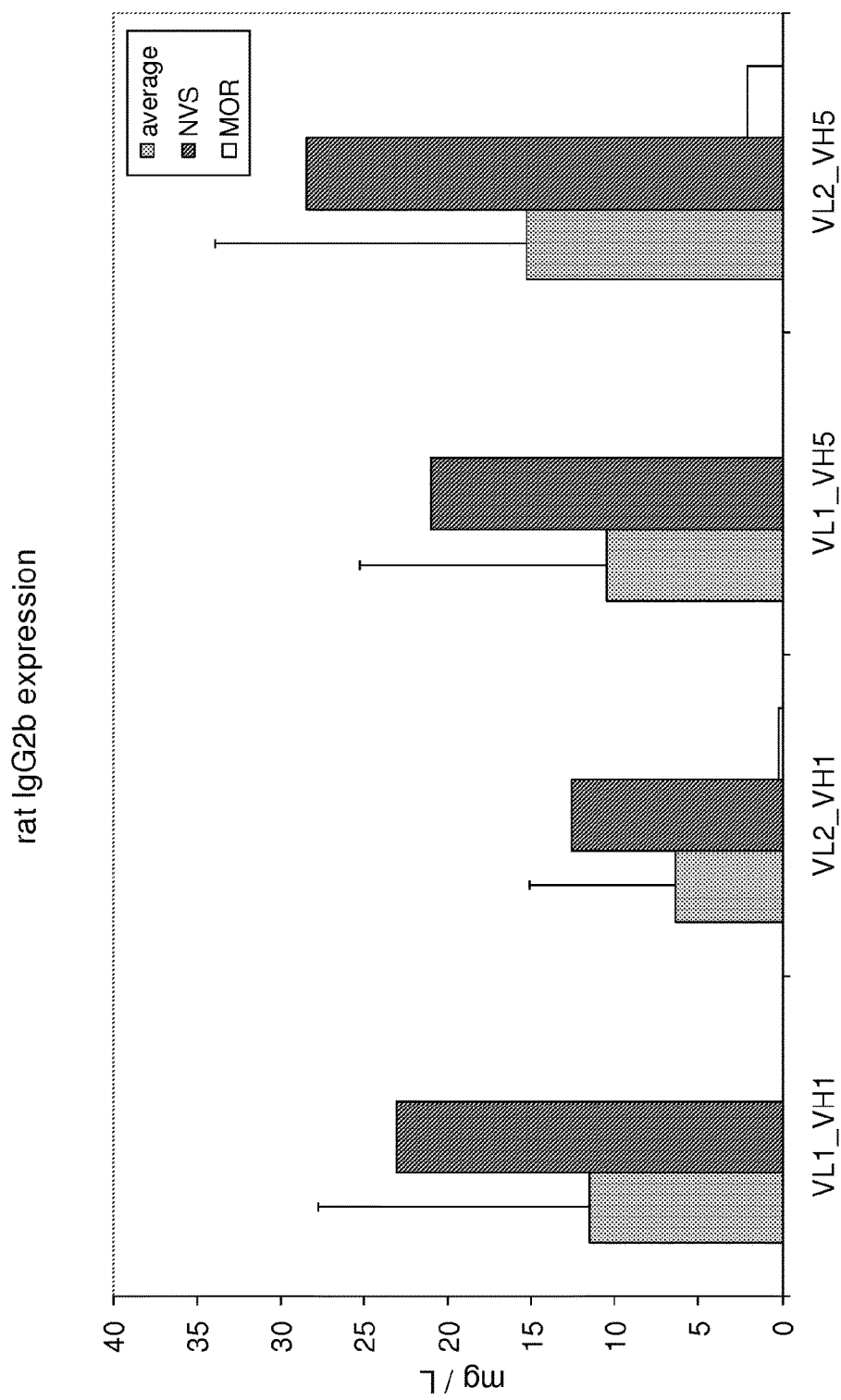
FIG. 40 shows the expression of rat IgG2b. There is not much difference among the four rat combinations tested.

In practice, the rat VL- and VH-mastergenes were re-cloned into mammalian expression vectors, and the resulting plasmids were used for transient transfection of a mammalian suspension cell line as described in Materials and Methods. We have not observed dramatic differences in expression level of the four rat combinations in rat IgG2b format; however, VH5-combinations seemed to be expressed about 5-fold better than VH1-combinations in rat IgG2c format where VL2-VH5 was slightly better expressed than VL1-VH5. Results for IgG2b are shown in FIG. 40, results for IgG2c in FIG. 41. The expression levels of the tested rat VL-VH-combinations in Fab and IgG formats did not correlate.

All rat VL and VH-mastergene combinations were purified in a 2-step purification process using Äkta express. Expressed Fab-fragments were bound to chelated Ni2+ and washed either with 15 column volumes of 20 mM Na-Phosphatbuffer/500 mM NaCl, pH 7.4, 20 mM Imidazole or, in a separate purification, using 20 column volumes of 30% Isopropanol/20 mM Na-Phosphatbuffer pH 7.4. Second step of purification (SEC) was identical for both procedures (with or without isopropanol treatment) and is described above. After purification, both protein preparations were compared regarding yield, concentration, purity, ratio of VH and VL and thermal stability. A wash step with 30% isopropanol while the Fab is still bound to the IMAC column was introduced in order to receive Fab fragments that are of higher purity. However for some Fab fragments this treatment was seen to be too harsh because the interface—the hydrophobic interaction between heavy and light chain—was not strong enough to endure this procedure. The heavy and light chains of such Fab fragments were eluted at different stages and therefore the ratio between the two chains did deviate from 1:1. FIG. 42 shows an overview of expression yields of all tested Fab rat framework combinations after washing on IMAC with and without isopropanol in a color code for selection criteria.

Thermal Stability

Figure 43:
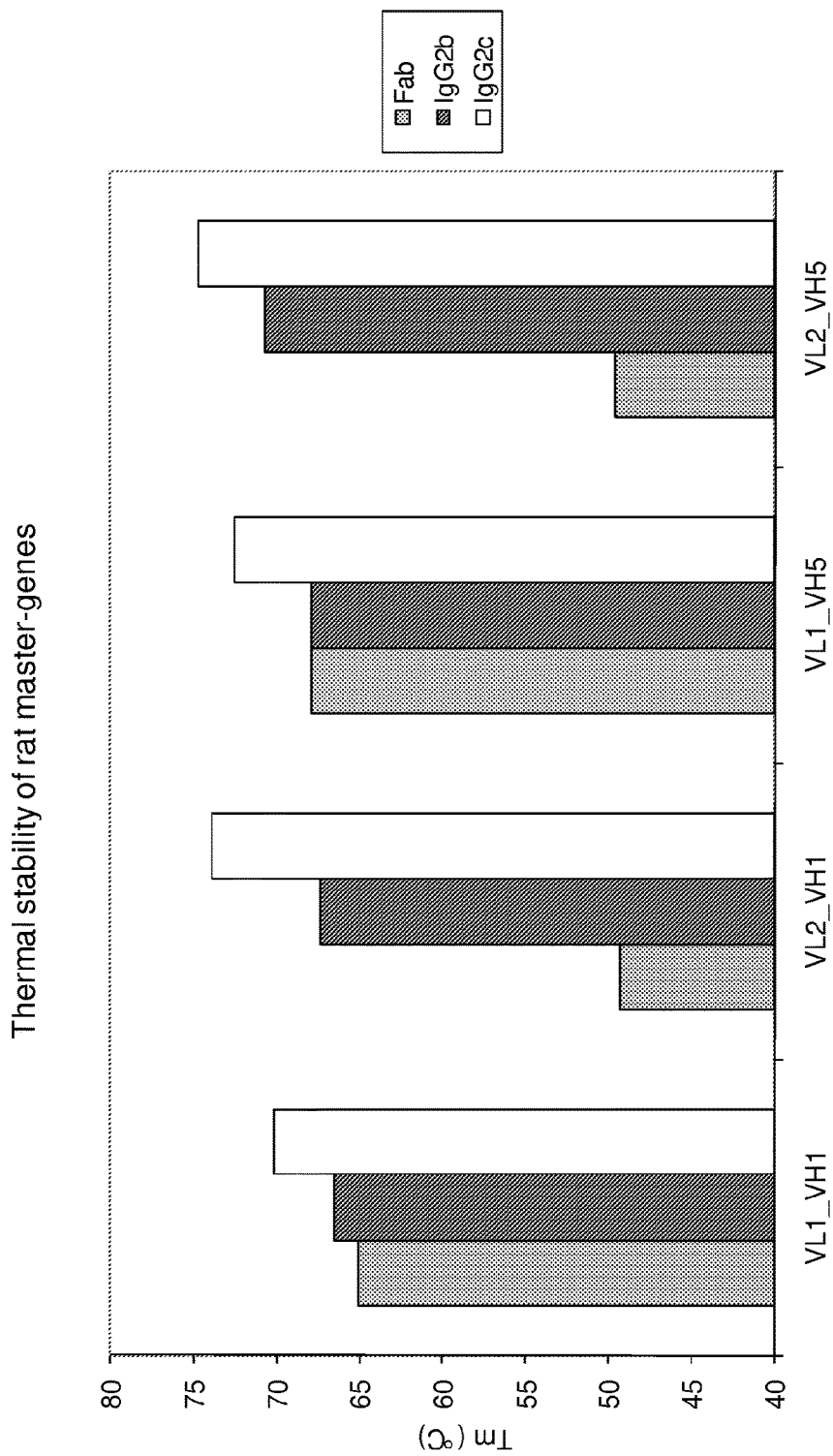
FIG. 43 illustrates thermal stability of murine mastergenes in Fab- and IgG format. The thermal stability of all tested rat VL-VH combinations was reasonably high.
Figure 45:
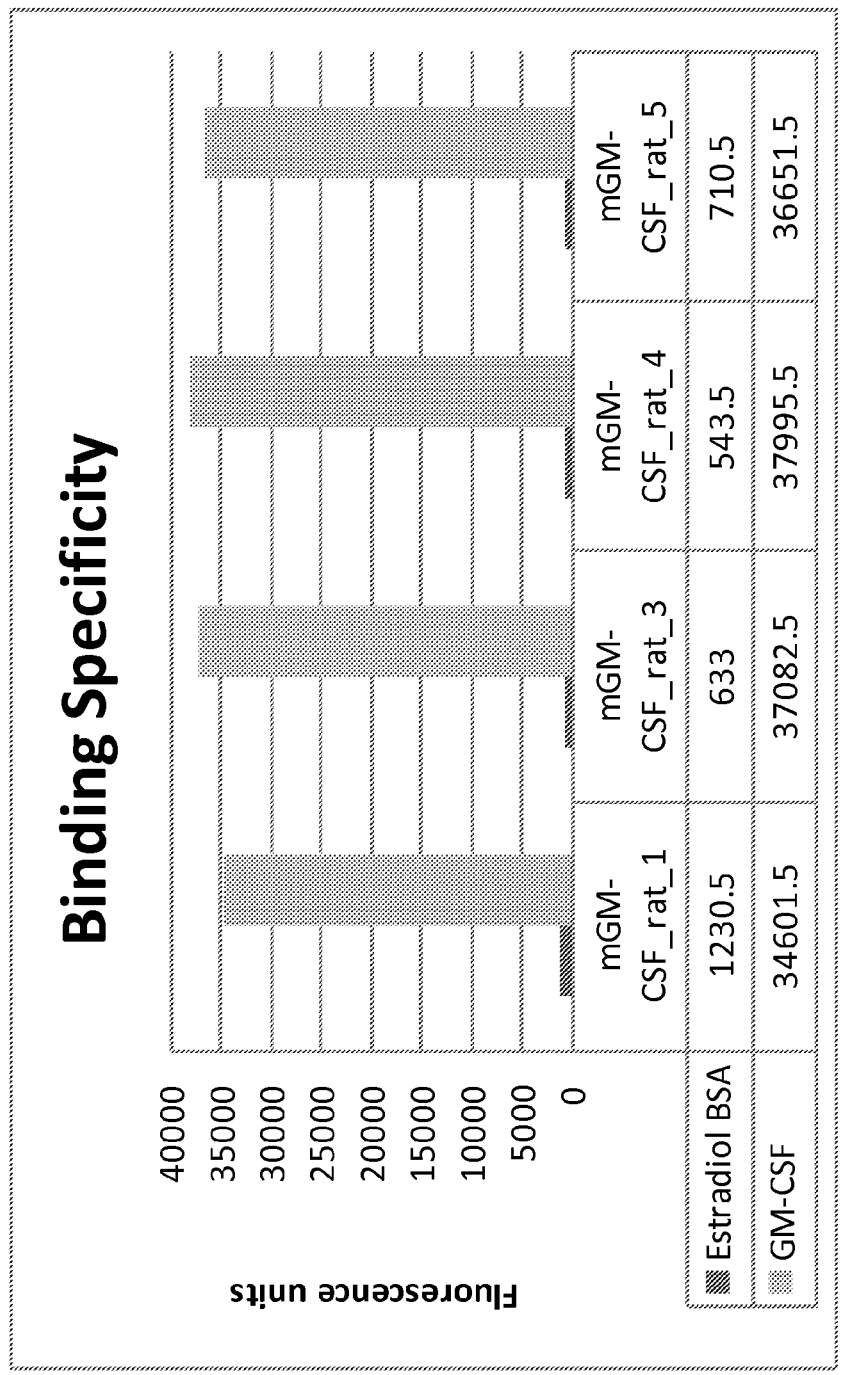
FIG. 45 demonstrates specificity of four rat Fab fragments for GM-CSF. All four Fab fragments were highly specific.

As described for the murine library, protein stability and resistance to environmental stress (such as proteases, heat or chaotropic agents) are an intrinsic property of protein and are typically independent of the expression conditions. Tm values (all within the range 67-75° C.) shown in FIG. 43 indicate that thermal stability of four rat VL-VH variants tested in IgG2b and IgG2c formats did not vary; however, stability of the rat VL2-combinations in Fab-format (Tm about 48° C.) was lower than the stability of the rat VL1-combinations (Tm about 65° C.).

Selection of Fv-Frameworks for Library Construction

Considering scarcity of available sequences of re-arranged rat antibodies in databases making solid statistical assessment of germ-line sequence-prevalence difficult, we opted to construct rat combinatorial phagemid library using a single robust Fv-framework. We selected the VL1-VH5 combination because: (i) it had the highest display in the Fab-format on the tip of filamentous phage (see FIG. 35); (ii) it was clearly best expressed in the soluble Fab-format in *E. coli* (about 17 mg/L); (iii) its expression level in tested IgG-formats was good (>10 mg/L); and (iv) its thermal stability was high (Tm at about 70° C.). Diversified LCDR3- and HCDR3-library cassettes were cloned into this selected Fv-framework as described herein below.

Example 2.5

Diversification of the Rat Library

Construction of HCDR2 Mini-Library Cassette by Using Primers with Wobbled Positions It had been observed, www.bioc.uzh.ch/antibody/Structures/AgContact/index.html that the most important residues in HCDR2 involved in the antigen-contact are located in positions 52, 52a, 54, 56, and 58 (Kabat numbering). Variation at these positions allows natural in vivo selection of antibodies with antigen-tailored binding pocket comprising HCDR2. We investigated the amino acid distribution for germline sequence families of rearranged antibodies represented by our three selected rVH master-genes (rVH1_RV, rVH2 and rVH5), compiled a list of residues which are frequently found in particular positions of HCDR2, and introduced these variations into the selected master-genes. In order to preserve prevalence of the germ-line sequence, the alternative residues found in the rearranged antibodies but not in germ-line sequences were intentionally underrepresented in the design (see FIG. 44). Sequence analysis for about 30 randomly picked clones per framework indicated that desired variants (five per framework) were represented in the HCDR2 with a frequency similar to our design; however, about 10% of randomly picked clones carried unintended nucleotide deletions mainly in the positions which were wobbled in the PCR-primers (data not shown). In order to ensure low abundance of frame-shifted clones in the library we decided to dilute the plasmid pool encoding variations in HCDR2 with plasmid encoding wild-type VH-framework. Hence in the final library the minor variants in HCDR2 are about 10-fold less abundant than in our initially HCDR2-design.

The intended variability (five amino acid sequence variants in master-gene) was introduced by DNA amplification in 10 cycles of PCR with Platinum Pfx DNA polymerase (Invitrogen) and a set of forward and reverse primers. The variability in rVH5 was introduced by using forward primer containing wobbled positions with defined nucleotide ratio:

(SEQ ID NO: 133)
ACCAAAGGTCTCGAGTGGGTGGCGACCATTAG(70%)/

C(30%)CTATGATGGCAGCAG(60%)/

A(20%)/C(20%)CACCTATTATCGTGATAGC.

The resulting PCR product was digested with XhoI/BssHII, and cloned into the rVH5 master-gene in pMorph32 plasmid. Plasmid pool containing the introduced variety in the master-gene was diluted 1:10 with plasmid encoding the original master-gene, and used for introduction of the LCDR3-library cassette.

Construction of LCDR3 Library Cassette

MBP-stuffer for rat VL1 is identical as mVLB1, and LCDR3 library-cassettes for mVLB1 and rVL1 are identical. LCDR3 library cassette was constructed as described above in the case of mouse library cassette. The design itself was identical to the murine LCDR3, while the flanking regions differed, to reflect the natural framework of the LCDR3:

These flanking regions, represent a part of antibody framework 3 and the terminal VL-antibody framework 4. Thus it was possible to PCR-amplify and clone the cassette at a later stage.

(SEQ ID NO: 134)
rVk1
5' GAAGACGTGGCGACCTATTTTTGC-T8-CAG-T9-T10-

T11-T12-CCG-T13

ACCTTTGGTGCGGGCACCA wherein T8-T13 are TRIM-mixes.

Sequences of all oligonucleotides used for preparation of LCDR3 cassette are listed in Table 37.

TABLE 37

| name | sequence |
|---|---|
| LCDR3 specific forward primer rat | |
| rVk2 | Lib67CTGCAACCGGAAGACGTGGCGACCTATTTTTGC (SEQ ID NO: 135) |
| | Overlapping oligos |
| rat | Lib70CGGCCACGTACGTTTGATTTCCAGTTTGGTGCCACCGCC AAAGG (SEQ ID NO: 136) |
| | Vk rev primer |
| rat | Lib68CGGCCACGTACGTTTGATTTC (SEQ ID NO: 137) |

Construction of HCDR3 Library Cassette

HCDR3 library cassette also was constructed exactly as described above in the case of mouse library cassette. The design of the HCDR3-cassette is identical to the design developed for the murine HCDR3. Thus, all information about the HCDR3-TRIM and the PCR amplification-oligos can be found in the respective chapter for the murine library.

Example 2.6

Test Panning with the Rat Library

The rat library consisting of one framework combination rVL1_rVH5 with diversifications in L-CDR3, H-CDR3 and H-CDR2 was used to generate antibodies specific for mouse GM-CSF.

Phages from the rat library were subjected to three rounds of selection on murine GM-CSF (AbD Sereotec, Germany). GM-CSF was biotinylated according to manufacturer's instruction (Amersham, GE Healthcare). Biotinylated murine GM-CSF is hereinafter referred to as "Bio-GM-CSF". Phages were pre-blocked with 2× ChemiBLOCKER containing 0.1% Tween for two hours and subsequently pre-adsorbed to uncoated NeutrAvidin™ plates for one additional hour at room temperature. This step is included to remove phages specific to the non-target NeutrAvidin. The pre-cleared rat library phage supernatant, obtained as described above, was incubated with 200 nM Bio-GM-CSF for 1 hour at room temperature on a rotator. Phages bound to Bio-GM-CSF were captured on Neutravidin coated wells (NeutrAvidin strips; Pierce) for 30 min and subsequent unbound phage were washed away as outlined in Table 38. Specific bound phages were eluted by adding 100 µl of 25 mM DTT in 10 mM Tris HCl, pH 8.0 to each well and incubating for 10-15 min at RT shaking. The DTT eluates of each selection were collected. E. coli TG1 with an OD600 nm of 0.6-0.8 were added to the phage eluates of each selection and incubated for 30 min in a water bath. After infection bacteria were plated out evenly on two large LB/Cm/Glu agar plates for each selection and incubated over night at 37° C. For the following panning rounds bacterial suspensions of each pool were collected and used to propagate phages for an additional panning round as described above. In total three subsequent rounds of phage selection were performed with increasing stringency of washing (see Table 38)

TABLE 38

Washing conditions applied in phage panning

| 1st Round | 2nd Round | 3rd Round |
|---|---|---|
| 3 × PBS 0.05% Tween, quick | 1 × PBS 0.05% Tween, quick | 10 × PBS 0.05% Tween, quick |
| 2 × PBS 0.05% Tween, 5 min shaking | 4 × PBS 0.05% Tween, 5 min shaking | 5 × PBS 0.05% Tween, 5 min shaking |
| 3 × PBS, quick | 1 × PBS, quick | 10 × PBS, quick |
| 2 × PBS, 5 min shaking | 4 × PBS, 5 min shaking | 5 × PBS, 5 min shaking |

Sub-cloning of selected phage, micro-expression of Fab fragments were performed as outlined for the mouse library herein above. Primary screening in ELISA was performed in solution with biotinylated antigen in capture mode. Essentially 20 µl anti-rat antibody (goat anti Rat IgG, F(ab')2, Jackson ImmunoResearch Laboratories, Inc) was immobilized to maxisorb plates at a concentration of 1.5 µg/ml in PBS incubated o/n at 4° C.

Blocking of rat BEL lysates was done in 3% BSA/TBST 30-60 min at 22° C. Rat Fab fragments were captured from bacterial crude lysate (BEL) by incubation for 1 hour at RT. After washing 5 times with TBST 20 µl biotinylated mGM_CSF (diluted to 0.75 µg/ml in 0.5% BSA TBST) was added to the plates and incubated for 0.5 h. After washing 5 times with TBST, the biotinylated mGM_CSF captured via specific rat Fab was detected by adding 20 µl avidin-HRP diluted 1:5000 in 0.5% BSA TBST at RT for 1 h. After additional washing 5 times with TBST 20 µl quanta blue substrate to the screening plates using a MultiDrop384. After 5-10 min, fluorescence was measure with the GENios Pro (Tecan). Signals 5-10 fold over background were considered as mGM-CSF specific binding of Fab fragments.

Table 39 summarizes the screening result of the mGM-CSF panning. 262 clones were screened in ELISA on captured bio-mGM-CSF as described above. 52 clones show 5-fold clear signal over background were subjected to sequencing of VH to identify unique Fab fragments. Out of those 51 sequenced clones five unique Fab sequences were identified, which show sequence diversity in H-CDR3 sequence. The H-CDR1 and the H-CDR2 show no sequence variation and are identical to rat VH5 germline sequence.

TABLE 39

Overview Selection rat HuCAL library against mouse GM-CSF

| Sublibrary | # Screened | Primary hits | Hit rate | # Sequenced | Unique Sequence |
|---|---|---|---|---|---|
| rVH5-Vk1 | 262 | 51 | 19% | 51 | 5 |

These five specific Fab fragments were expressed and purified as described in mouse sections described herein above. Heavy chain CDR sequences are shown in Table 40. Expression and biophysical features are summarized in Table 41. All five clones are well expressed in E. coli with expression yield in a range from 5-15 mg/L. On a size exclusion chromatography column all five Fab fragments showed a monomer elution profile, indicating that rat Fragment have no tendency towards misfolding or antibody aggregation. Thermal stability was assessed using the method described in section "Thermal stability" of the mouse library herein above. Except clone mGM-CSF_rat2, all other four rat Fab fragments show an apparent temperature unfolding Tm in the range of 68.5° C. up to 72° C., which reflects the unfolding temperature of the library rVL1_VH5 framework.

TABLE 40

Heavy chain complementarity-determining region sequence of mouse GM-CSF specific antibodies

| Cone | H-CDR1 | H-CDR2 | H-CDR3 |
|---|---|---|---|
| mGM-CSF_rat_1 | FTFSNYGMA | WVRQAPTKGLETISYDGSSTYYRDSVKG | DSWGYYRRKFDY |
| mGM-CSF_rat_2 | FTFSNYGMA | WVRQAPTKGLETISYDGSSTYYRDSVKG | GYYTGSFD |
| mGM-CSF_rat_3 | FTFSNYGMA | WVRQAPTKGLETISYDGSSTYYRDSVKG | NDYGGWRYKFDY |
| mGM-CSF_rat_4 | FTFSNYGMA | WVRQAPTKGLETISYDGSSTYYRDSVKG | SDWGGMRYKMDY |
| mGM-CSF_rat_5 | FTFSNYGMA | WVRQAPTKGLETISYDGSSTYYRDSVKG | YGWYKGRYKFDY |

(Table 39 discloses the "H-CDR1" sequences as SEQ ID NOS 138, 138, 138, 138 and 138, the "H-CDR2" sequences as SEQ ID NOS 139, 139, 139, 139 and 139 and the "H-CDR3" sequences as SEQ ID NOS 140-144, respectively, in order of appearance)

TABLE 41

Expression and thermal denaturation data mGM-CSF specific rat antibodies Expression and Stability

| Clone | Frame work combination | Expression rate mg/l | Monomer portion [%] | Tm [° C.] |
|---|---|---|---|---|
| mGM-CSF_rat_1 | rVH5-K1 | 5 | 100 | 70 |
| mGM-CSF_rat_2 | rVH5-K1 | 7 | 99 | 55 |
| mGM-CSF_rat_3 | rVH5-K1 | 15.5 | 100 | 72 |
| mGM-CSF_rat_4 | rVH5-K1 | 12 | 100 | 71.5 |
| mGM-CSF_rat_5 | rVH5-K1 | 9.5 | 100 | 68.5 |

Figure 41:
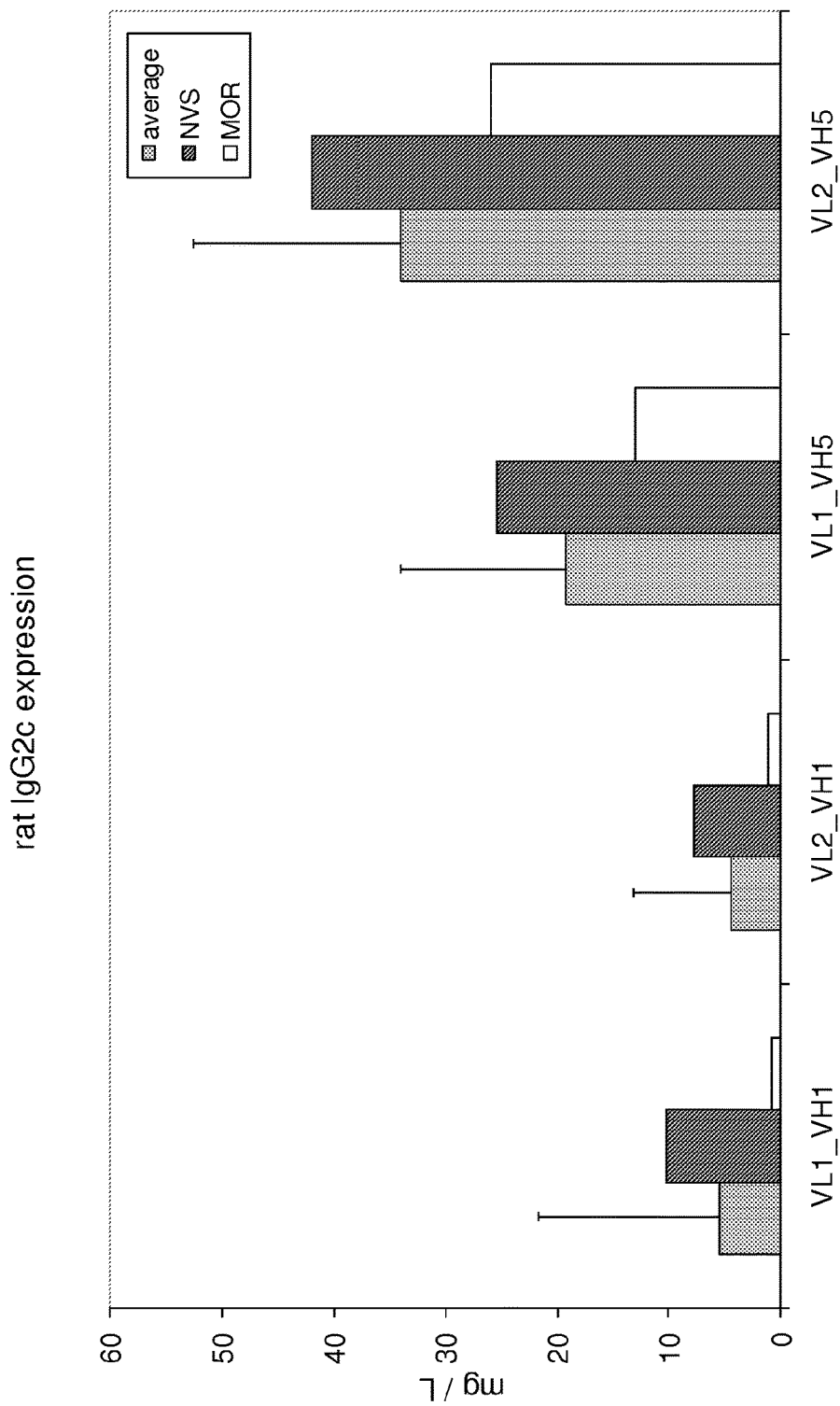
FIG. 41 shows the expression of rat IgG2c. Best expression is observed with the rVH5-combinations.

The specificity of four of the rat Fab fragments for GM-CSF was demonstrated in a specificity ELISA (see FIG. 41). All four rat antibodies gave a highly specific signal on directly immobilized GM-CSF on Maxisorp plates, but no signal with the unrelated antigen Estradiol-BSA.

This examples highlights the fact that both, the framework as well as the diversified CDRs contribute to the overall stability of an antibody molecule. By careful selection of highly stable antibody frameworks and sophisticated analysis and re-synthesis of CDR, antibody libraries can be synthetically build up which show superior behavior regarding expression and bio-physical characteristics and well defined binding specificities.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A synthetic rodent antibody or antibody fragment library of variable heavy (VH) and variable light (VL) chain combinations, wherein the VH-VL combinations consist of
   a) VH1/Vk3,
   b) VH2/Vk1, and
   c) VH5/Vk3,
   wherein a variable heavy chain or variable light chain comprises an amino acid sequence modification as compared to amino acid sequences encoded by germline genes, wherein said amino acid sequence modification results from modifying nucleic acids encoding the variable heavy chain or variable light chain to include a restriction site.

2. The library of claim 1, wherein said rodent is selected from mouse and rat.

3. The library of claim 1, wherein said library has a diversity of at least $1.0*10^8$ in the H-CDR3 region.

4. The library of claim 1, wherein said library is an unbiased library.

5. The library of claim 1, wherein essentially all VH-VL combinations of said library are efficiently displayed as measured by sandwich phage ELISA.

6. The library of claim 1, wherein essentially all VH-VL combinations comprise a thermal stability Tm of more than 62° C.

7. The library of claim 1, wherein the nucleic acid sequences encoding the H-CDR3 regions of essentially all members of the library are flanked by nucleic acid sequences having unique restriction sites.

8. The library of claim 2, wherein said mouse is selected from the laboratory strains Balb/c and C57BL/6.

9. The library of claim 1,
   a) wherein VH1 is IGHV1-72*01 (SEQ ID NO: 179),
   b) wherein VH2 is IGHV2-2*01 (SEQ ID NO: 181), and
   c) wherein VH5 is IGHV5-9*04 (SEQ ID NO: 183).

10. The library of claim 1,
    a) wherein Vk1 is IGKV1-117*01 (SEQ ID NO: 163), and
    b) wherein Vk3 is selected from the group consisting of IGKV3-12*01 (SEQ ID NO: 164), and germline gene IGKV3-4*01 (SEQ ID NO: 166).

11. The library of claim 1, wherein said library consists of the VH-VL combinations of
    a) IGHV1-72*01 (SEQ ID NO: 179)/IGKV3-12*01 (SEQ ID NO: 164),
    b) IGHV1-72*01 (SEQ ID NO: 179)/IGKV3-4*01 (SEQ ID NO: 166),
    c) IGHV2-2*01 (SEQ ID NO: 181)/IGKV1-117*01 (SEQ ID NO: 163),
    d) IGHV5-9*04 (SEQ ID NO: 183)/IGKV3-12*01 (SEQ ID NO: 164), and
    e) IGHV5-9*04 (SEQ ID NO: 183)/IGKV3-4*01 (SEQ ID NO: 166).

12. The library of claim 1, wherein said library comprises H-CDR3s of the length of 7-12 amino acids.

13. The library of claim 12, wherein said library has a H-CDR3 design as shown in FIG. 5 or FIG. 6.

14. The library of claim 1, where the L-CDR3 of essentially all members of the library is of the length of 8 amino acids.

15. The library of claim 14, wherein said library has a L-CDR3 design as shown in FIG. 7 or FIG. 8.

16. The library of claim 1, wherein said library has a diversity of at least $1.0*10^4$ in the L-CDR3 region.

17. The library of claim 1, wherein said library is a mouse library and at least one of amino acid residues 52, 52a, 54, 56 and 58 (Kabat numbering) of the H-CDR2 is diversified.

18. The library of claim 17, wherein said library has a H-CDR2 design as shown in FIG. 10 or FIG. 11.

19. The library of claim 1, wherein said library has a diversity of at least $1.0*10^5$ in the H-CDR2 region.

20. The library of claim 1, wherein essentially all VH-VL combinations are expressed in E. coli in Fab format at levels of more than 5 mg/L.

21. The library of claim 1, wherein essentially all VH-VL combinations are expressed in a mammalian system in IgG format at levels of more than 5 mg/L.

22. The library of claim 1, wherein the nucleic acid sequences encoding the L-CDR3 regions of essentially all members of the library are flanked by nucleic acid sequences having unique restriction sites.

23. The library of claim 1, wherein the nucleic acid sequences encoding the H-CDR2 regions of essentially all members of the library are flanked by nucleic acid sequences having unique restriction sites.

24. The library of claim 1, wherein said modifications are selected from the group consisting of IGHV1-7201 with a Q1E mutation (SEQ ID NO: 179), IGHV 1-72*01 with a Q1E, a K67R and a A68V mutation (SEQ ID NO: 180), IGHV2-2*01 with a Q1E mutation (SEQ ID NO: 181), and IGHV5-9*04 with a K3Q mutation (SEQ ID NO: 183).

* * * * *